(12) United States Patent
Zhang et al.

(10) Patent No.: US 10,808,005 B2
(45) Date of Patent: Oct. 20, 2020

(54) LIGAND FOR ORPHAN NUCLEAR RECEPTOR NUR77 AND USES THEREOF

(71) Applicant: IXMEDICINE (XIAMEN) BIOLOGICAL TECHNOLOGY COMPANY LIMITED, Fujian (CN)

(72) Inventors: Xiaokun Zhang, Xiamen (CN); Xiangzhi Lin, Xiamen (CN); Ying Su, Xiamen (CN); Zhiping Zeng, Xiamen (CN); Mengjie Hu, Xiamen (CN); Qiang Luo, Xiamen (CN); Yi Zhu, Xiamen (CN); Alitongbieke Gulimiran, Xiamen (CN)

(73) Assignee: IXMEDICINE (XIAMEN) BIOLOGICAL TECHNOLOGY COMPANY LIMITED, Fujian (CN)

( * ) Notice: Subject to any disclaimer, the term of this patent is extended or adjusted under 35 U.S.C. 154(b) by 0 days.

(21) Appl. No.: 16/315,099

(22) PCT Filed: Jul. 4, 2017

(86) PCT No.: PCT/CN2017/091726
§ 371 (c)(1),
(2) Date: Jan. 3, 2019

(87) PCT Pub. No.: WO2018/006804
PCT Pub. Date: Jan. 11, 2018

(65) Prior Publication Data
US 2019/0330261 A1  Oct. 31, 2019

(30) Foreign Application Priority Data
Jul. 4, 2016 (CN) .......................... 2016 1 0520308

(51) Int. Cl.
*C07J 63/00* (2006.01)
*A61P 35/00* (2006.01)

(52) U.S. Cl.
CPC .............. *C07J 63/00* (2013.01); *A61P 35/00* (2018.01)

(58) Field of Classification Search
CPC ....... A61K 31/19; A61K 31/56; A61K 31/352
See application file for complete search history.

(56) References Cited

U.S. PATENT DOCUMENTS

2004/0220267 A1* 11/2004 Devlin ............... A61K 31/56
514/559

FOREIGN PATENT DOCUMENTS

| CN | 101351211 A | 1/2009 |
| CN | 101805390 B | 7/2012 |
| CN | 103642887 B | 6/2016 |
| CN | 105985401 A | 10/2016 |
| EP | 2213679 A1 | 8/2010 |
| WO | 2007077203 A2 | 7/2007 |
| WO | 2015148802 A1 | 10/2015 |

OTHER PUBLICATIONS

Hu, Mengji et al., "Celastrol-Induced Nur77 Interaction with TRAF2 Alleviates Inflammation by Promoting Mitochondrial Ubiquitination and Autophagy," Molecular Cell, vol. 66, Apr. 6, 2017, pp. 141-153.
Klaic, Lada et al., "Remarkable Stereospecific Conjugate Additions to the Hsp90 Inhibitor Celastrol," National Institute of Health, J Am Chem Soc., edition 133, vol. 49, Dec. 14, 2011, pp. 19634-19637.
Lu, Zhongzheng et al., "Pristimerin Induces Apoptosis in Imatinib-Resistant Chronic Myelogenous Leukemia Cells Harboring T315I Mutation by Blocking NF-$_κ$B Signaling and Depleting Bcr-Abl," Molecular Cancer, May 19, 2010, pp. 1-17.
Lee, Jin Sun et al., "Anticancer Activity of Pristimerin in Epidermal Growth Factor Receptor 2-Positive SKBR3 Human Breast Cancer Cells," Biol. Parm. Bull, vol. 36 No. 2, Feb. 2013, pp. 316-325.
Ding, Hai-peng et al., "Research Progress in Pharmacologic Molecular Targets of Celastrol," Chin K Pharmacol Toxicol, vol. 26, No. 4, Aug. 2012, pp. 570-576. (English Abstract Only).
Pei, Liming et al., "Regulation of Macrophage Inflammatory Gene Expression by the Orphan Nuclear Receptor Nur77," Molecular Endocrinology, vol. 20, No. 4, Dec. 2005, pp. 786-794.

(Continued)

*Primary Examiner* — Pancham Bakshi
(74) *Attorney, Agent, or Firm* — Heslin Rothenberg Farley & Mesiti P.C.

(57) ABSTRACT

Provided are use of a compound of Formula I as a ligand of orphan nulear receptor Nur77, and in the prevention or treatment of a orphan nulear receptor Nur77 associated disease,

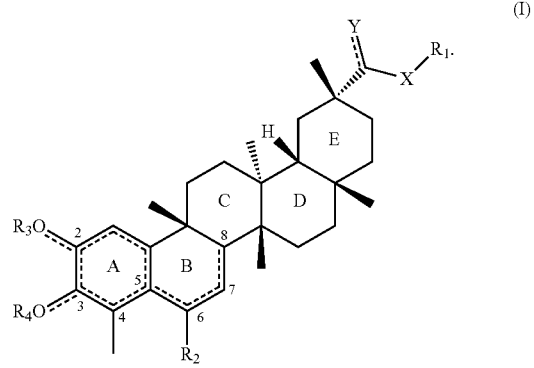

(I)

11 Claims, 13 Drawing Sheets

(56) References Cited

OTHER PUBLICATIONS

Figure 1:
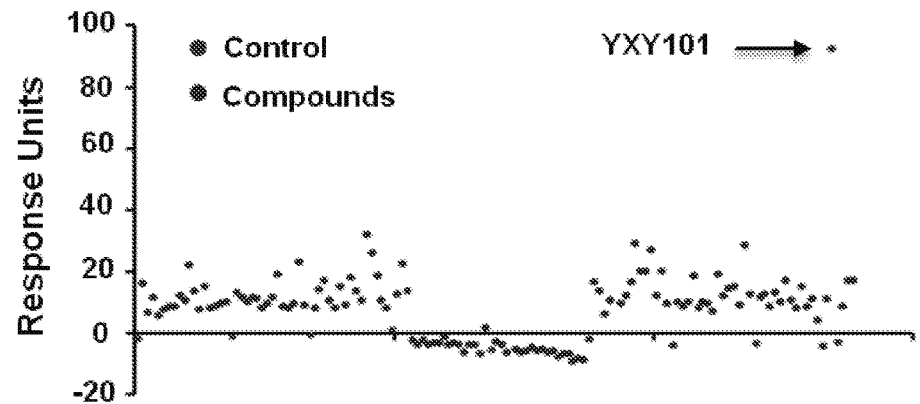

Zhang, Xiao-kun, "Targeting Nur77 Translocation," Oncology, Endocrine & Metabolic, Expert Opinion Ther. Targets, 2007, pp. 69-79.
Woronicz, John D. et al., "Requirement for the Orphan Steroid Receptor Nur77 in Apoptosis of T-cell Hybridomas," Letters to Nature, vol. 367, Jan. 20, 1994, pp. 227-281.
Liu, Zheng-Gang et al., "Apoptotic Signals Delivered through the T-cell Receptor of a T-cell Hybrid Require the Immediate-Early Gene Nur77," Letters to Nature, vol. 367, Jan. 20, 1994, pp. 281-284.
Li, Yin et al., "Molecular Determinants of AHPN (CD437)-Induced Growth Arrest and Apoptosis in Human Lung Cancer Cell Lines," Molecular and Cellular Biology, vol. 18, Aug. 1998, pp. 4719-4731.
Li, Hui et al., "Cytochrome C Release and Apoptosis Induced by Mitochondrial Targeting of Nuclear Orphan Receptor TR3," Science, vol. 289, Aug. 18, 2000, pp. 1159-1164.
Lin, Bingzhen et al., "Conversion of Bcl-2 from Protector to Killer by Interaction with Nuclear Orphan Receptor Nur77/TR3," Cell Press, vol. 116, Feb. 20, 2004, pp. 527-540.
Chang, Chawnshang et al., "Isolation and Characterization of Human TR3 Receptor: A Member of Steroid Receptor Superfamily," Proceedings of the 9$^{th}$ International Symposium of the Journal of Steroid Biochemistry, *Recent Advances in Steroid Biochemistry*, Las Palmas, Canary Islands, Spain, May 28-31, 1989, Vol. 34, Nos. 1-6, 1989 pp. 391-395.
Maxwell, Megan A. et al., "The NR4A Subgroup: Immediate Early Response Genes with Pleiotropic Physiological Roles," Nuclear Receptor Signaling, vol. 4, 2005, pp. 1-8.
International Search Report (and English translation) of the International Searching Authority for PCT/CN2017/091726 dated Sep. 27, 2017.
Tang, Kaiyong et al., "Design, Synthesis and Biological Evaluation of C(6)-Modified Celastrol Derivatives as Potential Antitumor Agents," Molecules 2014, 19, pp. 10177-10188.
Tang, Kaiyong et al., "Design, Synthesis and Biological Evaluation of C(6)-Indole Celastrol Derivatives as Potential Antitumor Agents," RSC Advances, 2015, 5, pp. 19620-19623.
Furbacher, Todd R. et al., "Catalytic Inhibition of Topoisomerase IIα by Demethylzeylasterone, a 6-Oxophenolic Triterpenoid from Kokoona Zeylanica," J. Nat. Prod., 2001, 64, pp. 1294-1296.
Ren, Hua-Yan et al., "Cytoplasmic TRAF4 Contributes to the Activation of p70s6k Signaling Pathway in Breast Cancer," Impact Journals, Oncotarget, vol. 6, No. 6, Jan. 9, 2015, pp. 4080-4096.
Xie, Lei et al., "Honokiol Sensitizes Breast Cancer Cells to TNF-α Induction of Apoptosis by Inhibiting Nur77 Expression," British Journal of Pharmacology, 2016, 173, pp. 344-356.
Shan, Wei-Guang et al., "Synthesis of 3- and 29-substituted Celastrol Derivatives and Structure-Activity Relationship Studies of their Cytotoxic Activities," Bioorganic & Medicinal Chemistry Letters, 27, 2017, pp. 3450-3453.
Bergstresser, Paul R. et al., Journal of Investigative Dermatology, 2010, vol. 130 (Suppl. 1) pp. S1-S149.

\* cited by examiner

US 10,808,005 B2

LIGAND FOR ORPHAN NUCLEAR RECEPTOR NUR77 AND USES THEREOF

CROSS REFERENCE TO RELATED APPLICATIONS

This application is a national stage filing under section 371 of International Application No. PCT/CN2017/091726, filed on Jul. 4, 2017, and published on Jan. 11, 2018 as WO 2018/006804, which claims priority to Chinese Application No. 201610520308.8, filed on Jul. 4, 2016. The entire contents of WO 2018/006804 are hereby incorporated herein by reference.

TECHNICAL FIELD

The present application relates to the field of medicine and biology, particularly, relates to a novel ligand of orphan nuclear receptor Nur77 and uses thereof. The present application also relates to use of a compound of Formula I to Formula V as a ligand of orphan nuclear receptor Nur77. The present application also relates to use of a compound of Formula I to Formula V for preventing or treating a disease associated with orphan nuclear receptor Nur77. The present application also relates to a method for screening a drug having anti-cancer (especially triple-negative breast cancer) activity. The present application also relates to a method for evaluating the diagnosis and treatment effects of triple-negative breast cancer and the like using the nuclear receptor Nur77 as a test index.

BACKGROUND ART

Orphan nuclear receptor Nur77, also called NGFIB (nerve growth factor IB) or orphan nuclear receptor TR3, is a critical regulator in the development of cancer, metabolism and inflammatory diseases. As an immediate early response gene, Nur77 plays an pivotal role in a number of cellular processes, including survival, apoptosis, inflammation, and autophagy, induced by different stimuli such as cytokinins, hormones, stress, metabolism, and apoptotic signals. (Pei L, et al., (2006), "Regulation of macrophage inflammatory gene expression by the orphan nuclear receptor Nur77", Mol. Endocrinol. 20 (4): 786-94; Zhang X K (2007), "Targeting Nur77 translocation", Expert Opin. Ther. Targets 11 (1): 69-79). The effect of Nur77 in apoptosis was first discovered in 1994, in which T cell receptor signaling induces Nur77 expression, and Nur77 expression increases during T cell receptor-mediated apoptosis. (Woronicz J D, Calnan B, et al. Requirement for the Orphan Steroid-Receptor Nur77 in Apoptosis of T-Cell Hybridomas. Nature, 367:277-81, 1994; Liu Z G, Smith S W, et al. Apoptotic Signals Delivered through the T-Cell Receptor of a T-Cell Hybrid Require the Immediate-Early Gene Nur77. Nature, 367:281-4, 1994). In the study of retinoid compound AHPN (also known as CD437), we discovered the role of Nur77 in tumor cell apoptosis. Studies have shown that Nur77 migrates from the nucleus to cytoplasm and locates to mitochondria by the stimulation of a variety of apoptotic signals, and the mitochondrial location of Nur77 is associated with the release of cytochrome c (Cytochrome c, Cyt c) and apoptosis. Nur77 lacking the DNA-binding domain can be constitutively located on mitochondria, allowing a large amount of cytochrome c to be released from mitochondria to induce apoptosis (Li Y, Lin B Z, et al. Molecular determinants of AHPN (CD437)-induced growth arrest and apoptosis in human lung cancer cell lines. *Mol Cell Biol,* 1998, 18(8); 4719-4731; Li H, Kolluri S K, et al. Cytochrome c release and apoptosis induced by mitochondrial targeting of nuclear orphan receptor TR3, Science, 2000, 289(5482); 1159-1164; Lin B, Kolluri S K, et al. Conversion of Bcl-2 from protector to killer by interaction with nuclear orphan receptor Nur77/TR3, Cell, 2004, 16; 527-540). Migration of Nur77 to cytoplasm and translocation to mitochondria is an essential condition for its apoptosis promotion effect. Therefore, many drugs induce apoptosis of cells of tumors and other major disease through Nur77 translocation to mitochondrial, and Nur77 mitochondria translocation will be an effective target for the development of new drugs.

Breast cancer is the "Number one killer" of women's health. According to the latest survey data, one woman in the world is diagnosed with breast cancer in every 3 minutes. In China, breast cancer shows a year-by-year increasing incidence and mortality rate in women, and ranks the highest incidence of female malignant tumors. The reason why breast cancer ranks the first in female malignant tumor mortality is its high metastasis, especially negative triple-negative breast cancer (TNBC), of which estrogen receptor (ER), progesterone receptor (PR) and proto-oncogene Her-2 are all negative, and which typical features are high metastasis, poor prognosis, insensitivity to endocrine therapy, and no effective drug in treatment so far. Previous studies have found that Nur77, as an early response gene, regulates many key life processes such as cell proliferation, apoptosis, embryonic development and angiogenesis, and its expression or dysfunction may lead to a series of diseases including tumors. Nur77 is generally not expressed or expressed in a low level in normal tissues, but can be massively induced during the development and treatment of tumor. Its induced expression can mediate the dual effects of cell proliferation and apoptosis, determing life or death of cells, and these two opposite phenomena depend on different stimuli and different location of Nur77 in the cell. Recent studies have shown that Nur77 can specifically bind to its ligand under the stimulation of inflammatory factors such as TNFα, and exerts anti-inflammatory activity by regulating functions of mitochondrion through cytoplasmic translocation.

In the previous study, we found that the development of breast cancer, especially triple-negative breast cancer, is also accompanied by inflammatory response and high activation of mTOR signaling pathway. Chronic inflammation is also an important basis for the development of breast cancer, and many non-steroidal anti-inflammatory drugs effective to other tumors are also used in the prevention and treatment of breast cancer. Therefore, based on Nur77, which is easily regulated by inflammatory factors and plays a key role in the regulation of breast cancer, an effective ligand that specifically binds to Nur77 is sought so as to develop a drug for the treatment of triple-negative breast cancer, which also has an important practical significance. Therefore, the present application establishes a novel method for screening an anticancer drug, that is, Nur77 is used as a target to find an effective ligand that specifically binds to Nur77 so as to develop a new compound molecule for treating cancer (such as triple negative breast cancer); and establishes a method for evaluation and diagnosis of the development of cancer (such as triple-negative breast cancer) by using Nur77 as a test indicator.

Since the marine ecological environment is quite different from the land, the biosynthesis pathways of small molecule metabolites of marine organisms are also very different. Therefore, marine natural products contain a large number of structurally unique compounds having multiple biological activities. For example, steroids and steroidal compounds have good antitumor and immunomodulatory activities, etc. The inventors of the present application have discovered a new class of pentacyclic triterpenoids YXY101 and its derivatives through extensive experimental research. The compounds are capable of binding to Nur77, inhibiting the mTOR signaling pathway and thereby inhibiting tumorigenesis. Therefore, the present application provides promising compounds, and it is particularly advantageous for the compounds of the present invention to act on cells expressing Nur77, and regulate the mTOR signaling pathway mediated by Nur77 which is newly discovered by the inventors can be used for the treatment of triple-negative breast cancer and other cancers (e.g., liver cancer, cervical cancer, lung cancer, triple positive breast cancer, colorectal cancer or prostate cancer).

Contents of the Invention

In the present invention, unless otherwise indicated, the scientific and technical terms used herein have the meanings commonly understood by those skilled in the art. Also, the procedures of cell culture, molecular genetics, nucleic acid chemistry, immunology laboratory operation used herein are all conventional and widely used in the corresponding fields. Meanwhile, for the purpose of better understanding of the present invention, the definitions and explanations of related terms are provided below.

As used herein, the term "tautomer" refers to a functional isomer formed by the rapid movement between two positions of an atom in a molecule. A typical example of such tautomer is keto-enol tautomers. The compounds described herein may exist in tautomeric forms and thus encompass all possible tautomers, and any combination or any mixture thereof.

As used herein, the term "stereoisomer" refers to an isomer of a molecule which has the same order of atoms or atom groups, but differs in spatial arrangement. In the present application, "stereoisomerism" of a compound is divided into conformational isomerism and configurational isomerism, wherein the conformational isomerism is further divided into cis-trans isomerism and optical isomerism. Therefore, in the present application, "stereoisomers" include all possible optical isomers and diastereoisomers, and any combinations thereof, for example, racemate (racemic mixtures), single enantiomer, mixture of diastereomers, single diastereomer. For example, when the compound of the invention contains an carbon-carbon double bond, it includes its cis isomer and the trans isomer, and any combination thereof, unless otherwise specified.

As used herein, the term "pharmaceutically acceptable salt" refers to (1) a salt formed with an acidic functional group (e.g., —COOH, —OH, —SO$_3$H, etc.) in the compound of the present invention and a suitable inorganic or organic cation (alkali), for example, a salt formed with a compound of the invention and an alkali metal or alkaline earth metal, an ammonium salt of a compound of the invention, and a salt formed with a compound of the invention and a nitrogen-containing organic base; and (2) a salt formed with a compound of the present invention and a basic functional group (e.g., —NH$_2$, etc.) with a suitable inorganic or organic anion (acid), such as a salt formed with a compound of the invention and an inorganic or organic carboxylic acid.

Thus, the "pharmaceutically acceptable salts" of the compounds of the invention include, but are not limited to, alkali metal salts such as sodium salts, potassium salts, lithium salts, and the like; alkaline earth metal salts such as calcium salts, magnesium salts, and the like; other metal salts, such as aluminum salts, iron salts, zinc salts, copper salts, nickel salts, cobalt salts, and the like; inorganic alkali salts, such as ammonium salts etc.; organic base salts, such as t-octylamine salts, dibenzylamine salts, morpholine salts, glucamine salts, phenylglycine alkyl ester salts, ethylenediamine salts, N-methylglucamine salts, guanidine salts, diethylamine salts, triethylamine salts, dicyclohexylamine salts, N, N'-dibenzylethylenediamine salts, chloroprocaine salts, procaine salts, diethanolamine salts, N-benzyl-phenethylamine salts, piperazine salts, tetramethylamine salts, tri(hydroxyl) aminomethane salts; hydrohalide salts such as hydrofluoride salts, hydrochloride salts, hydrobromide salts, and hydroiodide salts etc.; salts of mineral acids such as nitrates, perchlorates, sulfates, and phosphates etc.; lower alkyl sulfonates, such as mesylates, triflates, and ethanesulfonates etc.; aryl sulfonates, such as besylates, and p-benzenesulfonates etc.; salts of organic acids, such as acetates, malates, fumarates, succinates, citrates, tartrates, oxalates, and maleates etc.; and salts of amino acids such as glycinates, trimethylglycinates, arginine salts, ornithine salts, glutamates, and aspartates etc.

As used herein, the term "pharmaceutically acceptable ester" refers to an ester which is formed by an esterification reaction of a comound of the present invention and an alcohol when the compound contains a carboxyl group, or an ester which formed by an esterification reaction of a compound of the present invention with an organic acid, an inorganic acid or a salt of organic acid etc. when the compound contains a hydroxyl group. The ester may be hydrolyzed to form a corresponding acid or alcohol in the presence of an acid or a base.

As used herein, the term "$C_{1-6}$alkyl" refers to a straight or branched alkyl having 1 to 6 carbon atoms, such as methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, and the like. Preferable examples of the $C_{1-6}$alkyl include a $C_{1-5}$alkyl, a $C_{1-4}$alkyl, and a $C_{1-3}$alkyl. The "$C_{1-4}$alkyl" as used in the present invention refers to a straight or branched alkyl having 1 to 4 carbon atoms, which includes, but is not limited to, the specific examples within the above examples having 1 to 4 carbon atoms.

As used herein, the term "alkenyl" refers to a straight or branched hydrocarbonyl group containing at least one carbon-carbon double bond, and a typical example of which is a $C_{2-10}$alkenyl group, such as a $C_{2-6}$alkenyl group or a $C_{2-4}$alkenyl group. Specific examples include, but are not limited to, vinyl, propenyl, 2-propenyl, butenyl, 2-butenyl, butadienyl, pentenyl, 2-methyl-butenyl, 3-methyl-butenyl, 1,3-pentadienyl, 1,4-pentadienyl, hexenyl, 2-ethyl-butenyl, 3-methyl-pentenyl, 4-methyl-pentenyl, 1,3-hexadienyl, 1,4-hexadienyl, 1,5-hexadienyl, and the like.

As used herein, the term "alkynyl" refers to a straight or branched chain hydrocarbonyl group containing at least one carbon-carbon triple bond, and a typical example of which is a $C_{2-10}$alkynyl group, such as a $C_{2-6}$alkynyl group or a $C_{2-4}$alkynyl. Specific examples include, but are not limited to, ethynyl, propynyl, 2-propynyl, butynyl, 2-butynyl, 2-methyl-propynyl, butadiynyl, pentynyl, 2-methyl-butynyl, 3-methyl-butynyl, 1,3-pentadiynyl, 1,4-pentadiynyl, hexynyl, 2-ethyl-butynyl, 3-methyl-pentynyl, 4-methyl-pentynyl, 1,3-hexadiynyl, 1,4-hexadiynyl, 1,5-hexadiynyl, and the like.

As used herein, the term "cycloalkyl" refers to a monocyclic saturated alkyl, a typical example of which is 3- to 8-membered cycloalkyl, such as 3-, 4-, 5-, 6-, 7- or 8-membered cycloalkyl. As used herein, the term "3- to 8-membered cycloalkyl" refers to a cycloalkyl containing from 3 to 8 carbon atoms. Specific examples include, but are not limited to, cyclopropyl, cyclobutyl, cyclopentyl, cyclohexyl, cycloheptyl, cyclooctyl, and the like.

As used herein, the term "heterocycloalkyl" refers to a cycloalkyl containing at least 1 up to 4 (e.g., 1, 2, 3 or 4) heteroatoms selected from N, O and S, wherein the definition of "cycloalkyl" is as described above, and a typical example of which is 3- to 8-membered heterocycloalkyl, such as 3-, 4-, 5-, 6-, 7- or 8-membered heterocycloalkyl. As used herein, the term "3- to 8-membered heterocycloalkyl" refers to a heterocycloalkyl containing from 3 to 8 carbon atoms. As used herein, the "3- to 8-membered oxo-cycloalkyl" refers to 3- to 8-membered heterocycloalkyl as defined above wherein the heteroatom is O, and specific examples thereof include, but are not limited to, epoxyethyl, oxocyclobutyl, pyrrolidinyl, tetrahydrofuranyl, piperidinyl, piperazinyl, morpholinyl, thiomorpholinyl and the like.

As used herein, the term "aryl" refers to an aromatic group, a typical example of which is 6- to 14-membered aryl group, such as 6- to 10-membered aryl group. As used herein, the term "6- to 14-membered aryl" refers to a monocyclic, bicyclic or polycyclic aromatic group containing from 6 to 14 carbon atoms, including, for example, 6- to 8-membered aryl and 8- to 14-mebered fused aryl groups. The 6- to 8-membered aryl group means an aryl group having 6 to 8 carbon atoms, such as a phenyl group. The 8- to 14-membered fused ring aryl refers to an unsaturated, aromatic, fused ring group containing 8-14 ring forming carbon atoms formed by two or more cyclic structures sharing two adjacent carbon atoms, and specific examples thereof include, but are not limited to, naphthalene, anthracene, phenanthrene, and the like. The term "6- to 10-membered aryl" means an aromatic group having 6 to 10 carbon atoms, which includes, but is not limited to, the aromatic groups having 6 to 10 ring atoms within the above examples.

As used herein, the term "aryl-$C_{1-6}$alkyl" refers to a group in form of aryl-$C_{1-6}$alkyl-, wherein the"aryl" and the "$C_{1-6}$alkyl" are as defined above.

As used herein, the term "$C_{1-6}$alkoxy" refers to a group in form of $C_{1-6}$alkyl-O-form, wherein the "$C_{1-6}$alkyl" is as defined above.

As used herein, the term "$C_{1-6}$alkylamino" refers to a group in form of $C_{1-6}$alkyl-NH—, wherein the "$C_{1-6}$alkyl" is as defined above.

As used herein, the term "$C_{1-6}$alkylthio" refers to a group in form of $C_{1-6}$alkyl-S—, wherein the "$C_{1-6}$alkyl" is as defined above.

As used herein, the term "$C_{1-6}$alkanoyl" refers to a group in form of $C_{1-5}$alkyl-C(O)—, wherein the "$C_{1-5}$ alkyl" is as defined above.

As used herein, the term "$C_{1-6}$alkoxycarbonyl" refers to a group in form of $C_{1-6}$alkyl-OC(O)—, wherein the "$C_{1-6}$alkyl" is as defined above.

As used herein, the term "$C_{1-6}$alkoxycarbonyl-$C_{1-6}$alkyl" refers to a group in form of $C_{1-6}$alkyl-OC(O)—$C_{1-6}$alkyl-, wherein the "$C_{1-6}$alkyl" is as defined above.

As used herein, the term "3- to 8-membered cycloalkyl-aminoacyl" refers to a group in form of 3- to 8-membered cycloalkyl-NHC(O)—, wherein the "3- to 8-membered cycloalkyl" is as defined above.

As used herein, the term "halogen" includes, for example, fluorine atom, chlorine atom, bromine atom, and iodine atom.

As used herein, the term "6- to 15-membered heteroaryl group" refers to an aromatic group containing from 6 to 15 ring atoms and at least one of which is a hetero atom. The 6- to 15-membered heteroaryl group includes a "5- to 8-membered heteroaryl group" such as "5- to 7-membered heteroaryl group", "5- to 6-membered heteroaryl group" and the like. Specific examples of "5- to 8-membered heteroaryl" include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-hydroxy-pyridyl, 4-hydroxy-pyridyl, pyrimidinyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetraazinyl, azacycloheptatrienyl, 1,3-diazacycloheptatrienyl, azacyclooctatetraenyl, and the like. The 6- to 15-membered heteroaryl group also includes a "9- to 15-membered fused heteroaryl group" (for example, 9- to 15-membered benzoheteroaryl group), and specific examples thereof include, but are not limited to, benzofuranyl, benzoisofuranyl, benzothienyl, indolyl, isoindolyl, benzoxazolyl, benzimidazolyl, indazolyl, benzotriazolyl, quinolyl, 2-hydroxy-quinolyl, 4-hydroxy-quinolyl, 1-hydroxy-isoquinolyl, isoquinolyl, acridinyl, phenanthridinyl, benzopyridazinyl, phthalazinyl, quinazolinyl, quinoxalinyl, phenolzinyl, pteridinyl, purinyl, naphthyridinyl, phenazinyl, phenothiazinyl, and the like.

As used herein, the term "cell" particularly preferably refers to a cell that expresses Nur77. The compounds of the present invention are capable of specifically binding to Nur77 and functioning as a ligand thereof. Therefore, it is particularly advantageous for the compounds of the present invention to act on cells expressing Nur77, and regulate the newly discovered Nur77-mediated inflammation and mTOR signaling pathways. In a preferred embodiment, the cell are a cell of triple negative breast cancer or other cancers (e.g., a liver cancer cell, a cervical cancer cell, a lung cancer cell, a triple positive breast cancer cell, a colorectal cancer cell, or a prostate cancer cell).

As used herein, the term "orphan nuclear receptor Nur77" or "Nur77" refers to nerve growth factor IB (NGFIB), which is encoded by the NR4A1 gene (Chang C et al. (1989), "Isolation and characterization of human TR3 receptor: a member of steroid receptor superfamily", J. Steroid Biochem. 34(1-6): 391-5). Nur77 is involved in processes such as cell cycle, inflammation, and apoptosis, and its subcellular location is associated with cell survival and death (Pei L et al. (2006), "Regulation of macrophage inflammatory gene expression by orphan nuclear receptor Nur77", Mol. Endocrinol. 20(4): 786-94; Zhang X K (2007), "Targeting Nur77 translocation", Expert Opin. Ther. Targets 11(1): 69-79).

As used herein, the term "a Nur77-associated disease" refers to a disease, occurrence and/or progression of which is associated with the Nur77 signaling pathway. Studies have shown that, Nur77 is involved in processes such as cell cycle, inflammation, and apoptosis, and its subcellular location is associated with cell survival and death (ibid.). In addition, it has been reported that Nur77 can be induced by a variety of stimuli, including physiological stimuli, such as fatty acids, prostaglandins, growth factors, inflammatory cytokines, peptide hormones, etc.; as well as physical stimuli, such as magnetic fields, mechanical agitation (shearing force), membrane depolarization, etc. (Maxwell M A, Muscat G E (2006), "The NR4A subgroup: immediate early response genes with pleiotropic physiological roles", Nucl Recept Signal 4: e002). In addition, it is shown that, Nur77 also involved in the metastasis of some solid tumors (Ramaswamy S, Ross K N, Lander E S, Golub T R (2003), "A molecular signature of metastasis in primary solid tumors", Nat. Genet. 33(1): 49-54). In addition, it is shown that, Nur77 is abnormally expressed in synovial tissue of patient with inflammatory disease, cancer cells, psoriasis patients, atherosclerotic patients, and multiple sclerosis patients. Thus, the term "a Nur77-associated disease" includes, but is not limited to, inflammation (e.g., inflammation associated with atherosclerosis, inflammation associated with obesity, inflammation associated with diabetes, hepatitis, pneumonia, arthritis, and inflammatory bowel diseases), atherosclerosis, obesity, diabetes, psoriasis, multiple sclerosis, and cancers (e.g., triple-negative breast cancer).

As used herein, the term "subject" refers to an animal, particularly a mammal, preferably a human.

As used herein, the term "high fat diet" refers to a diet for daily intake of an animal (e.g., a mammal, such as a human) in which the fat content exceeds the amount of fat required for normal physiological activity of the animal.

As used herein, the term "effective amount" refers to an amount sufficient to achieve or at least partially achieve a desired effect. For example, a prophylactically effective amount refers to an amount sufficient to prevent, arrest, or delay the onset of a disease; a therapeutically effective amount refers to an amount sufficient to cure or at least partially arrest the disease and its complications in a patient already suffering from the disease. Determination of such an effective amount is well within the capabilities of those skilled in the art. For example, the amount effective for therapeutic use will depend on the severity of the disease to be treated, the general state of the patient's immune system, the general condition of the patient such as age, weight and sex, the mode of administration of the drug, other treatments administered simultaneously, and so on.

In the present application, through intensive research, the inventors have found that, a compound represented by Formula I to Formula V (for example, Compound YXY101) can target orphan nuclear receptor Nur77 and function as a ligand thereof. For example, such compound can be used for inhibiting mTOR activity by binding to orphan nuclear receptor Nur77 so as to treat a cancer associated with orphan nuclear receptor Nur77 (e.g., triple negative breast cancer).

Accordingly, in a first aspect, the present application relates to use of a compound of Formula I, a tautomer, a stereoisomer or a pharmaceutically acceptable salt or ester thereof, which is used as a ligand of orphan nuclear receptor Nur77, or used in the manufacture of a medicament used as a ligand of orphan nuclear receptor Nur77:

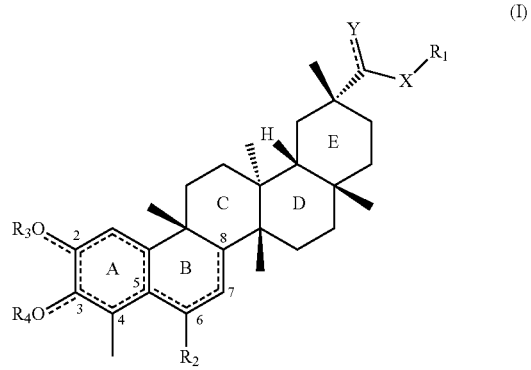

(I)

wherein,

X represents —NH—, —N(R)—, —O—, —CH$_2$— or halogen; wherein, when X is halogen, R$_1$ is absent;

when the bond between Y and the carbon atom attached thereto is a single bond, Y represents H, halogen, —OR, —SR or —NRR'; when the bond between Y and the carbon atom attached thereto is a double bond, Y represents O, S or NR;

R$_1$ is absent or represents H, —PO(OR)$_2$, C$_{1-6}$alkyl, glycosyl, C$_{1-6}$alkoxycarbonyl-C$_{1-6}$alkyl, 3- to 8-membered cycloalkyl-aminoacyl, aryl-C$_{1-6}$alkyl or aryl, wherein the C$_{1-6}$alkyl, glycosyl, C$_{1-6}$alkoxycarbonyl-C$_{1-6}$alkyl, 3- to 8-membered cycloalkyl-aminoacyl, aryl-C$_{1-6}$alkyl and aryl are unsubstituted or substituted with one or more (for example, 1, 2, 3 or 4) substituents selected from the group consisting of halogen, hydroxy, amino, C$_{1-6}$alkyl, C$_{1-6}$alkoxy, C$_{1-6}$alkylamino and C$_{1-6}$alkanoyl; preferably, the aryl is 6- to 14-membered aryl, such as 6- to 10-membered aryl; more preferably phenyl or naphthyl;

R$_2$ represents H, D, —PO(OR)$_2$, —CONH$_2$, —NH$_2$, —NHR, —NRR', —NHCOR, —NRCOR, —NHCOOR, —NHCONHR, —NHCONRR', —NRCONHR, —NRCONRR', —OH, —OR, —OCONHR, —OCONRR', —SH, —SR, —SOR, —SOOR, —SO$_2$NHR", nitro, halogen, glycosyl, cyano, trifluoromethyl, C$_{1-6}$alkyl, 3- to 8-membered cycloalkyl, 3- to 8-membered heterocycloalkyl, aryl, C$_{1-6}$alkyl-substituted aryl, 6- to 15-membered heteroaryl, alkenyl, alkynyl, sulfinyl, sulfonic acid group or sulfonate group; wherein the C$_{1-6}$alkyl, 3- to 8-membered cycloalkyl, 3- to 8-membered heterocycloalkyl, aryl, C$_{1-6}$alkyl-substituted aryl, 6- to 15-membered heteroaryl, alkenyl and alkynyl are unsubstituted or substituted with one or more (for example 1, 2, 3 or 4) substituents selected from the group consisting of amino, halogen, hydroxy, oxy, C$_{1-6}$alkyl, C$_{1-6}$alkoxy, C$_{1-6}$alkylthio, C$_{1-6}$alkanoyl, 3- to 8-membered cycloalkyl (e.g., cyclopropyl), 3- to 8-membered oxocycloalkyl (e.g., oxocyclobutyl), cyano, trifluoromethyl, C$_{1-6}$alkoxycarbonyl, C$_{1-6}$alkylamido, ureido group, carbamate, carboxyl and aryl;

R$_3$ and R$_4$ each independently is absent or represents H, C$_{1-6}$alkyl, C$_{1-6}$alkanoyl, C$_{1-6}$alkoxycarbonyl, glycosyl, aryl-C$_{1-6}$alkyl or aryl, wherein the C$_{1-6}$alkyl, C$_{1-6}$alkanoyl, C$_{1-6}$alkoxycarbonyl, glycosyl, aryl-C$_{1-6}$alkyl and aryl are unsubstituted or substituted with one or more (e.g., 1, 2, 3 or 4) substituents selected from the group consisting of halogen, hydroxy, amino, C$_{1-6}$alkyl, C$_{1-6}$alkoxy, C$_{1-6}$alkylamino and C$_{1-6}$alkanoyl; preferably, the aryl is 6- to 14-membered aryl, such as 6- to 10-membered aryl; more preferably phenyl or naphthyl;

R and R' each independently is selected from H, C$_{1-6}$alkyl, 3- to 8-membered cycloalkyl, aryl-C$_{1-6}$alkyl or aryl, wherein the C$_{1-6}$alkyl, 3- to 8-membered cycloalkyl, aryl-C$_{1-6}$alkyl and aryl are unsubstituted or substituted with one or more (e.g., 1, 2, 3 or 4) substituents selected from the group consisting of halogen, hydroxy, amino, C$_{1-6}$alkyl, C$_{1-6}$alkoxy, and C$_{1-6}$alkylamino;

R" represents C$_{1-6}$alkyl or aryl (e.g., 6- to 10-membered aryl group, preferably phenyl);

" ----- " in Formula (I) represents single bond or double bond; preferably, ring A contains 0, 1, 2 or 3 carbon-carbon double bonds; ring B contains 0, 1 or 2 carbon-carbon doubles bonds.

In a preferred embodiment, X represents —NH—, —N(R)—, —O—, —CH$_2$— or halogen; wherein, when X is halogen, R$_1$ is absent;

when the bond between Y and the carbon atom attached thereto is a single bond, Y represents H, halogen, —OR, —SR or —NRR'; when the bond between Y and the carbon atom attached thereto is a double bond, Y represents O, S or NR;

$R_1$ is absent or represents H, —PO(OR)$_2$, $C_{1-6}$alkyl, glycosyl, $C_{1-6}$alkoxycarbonyl-$C_{1-6}$alkyl, 3- to 8-membered cycloalkyl-aminoacyl, aryl-$C_{1-6}$alkyl or aryl, wherein the $C_{1-6}$alkyl, glycosyl, $C_{1-6}$alkoxycarbonyl-$C_{1-6}$alkyl, 3- to 8-membered cycloalkyl-aminoacyl, aryl-$C_{1-6}$alkyl and aryl are unsubstituted or substituted with one or more (for example, 1, 2, 3 or 4) substituents selected from the group consisting of halogen, hydroxy, amino, $C_{1-6}$alkyl, $C_{1-6}$alkoxy, $C_{1-6}$alkylamino and $C_{1-6}$alkanoyl; preferably, the aryl is 6- to 14-membered aryl, such as 6- to 10-membered aryl; more preferably phenyl or naphthyl;

$R_2$ represents H, D, —PO(OR)$_2$, —CONH$_2$, —NH$_2$, —NHR, —NRR', —NHCOR, —NRCOR, —NHCOOR, —NHCONHR, —NHCONRR', —NRCONHR, —NRCONRR', —OH, —OR, —OCONHR, —OCONRR', —SH, —SR, —SOR, —SOOR, —SO$_2$NHR", nitro, halogen, glycosyl, cyano, trifluoromethyl, $C_{1-6}$alkyl, 3- to 8-membered cycloalkyl, 3- to 8-membered heterocycloalkyl, aryl, $C_{1-6}$alkyl-substituted aryl, 6- to 15-membered heteroaryl, alkenyl, alkynyl, sulfinyl, sulfonic acid group or sulfonate group; wherein the $C_{1-6}$alkyl, 3- to 8-membered cycloalkyl, 3- to 8-membered heterocycloalkyl, aryl, $C_{1-6}$alkyl-substituted aryl, 6- to 15-membered heteroaryl, alkenyl and alkynyl are unsubstituted or substituted with one or more (for example 1, 2, 3 or 4) substituents selected from the group consisting of amino, halogen, hydroxy, oxy, $C_{1-6}$alkyl, $C_{1-6}$alkoxy, $C_{1-6}$alkylthio, $C_{1-6}$alkanoyl, 3- to 8-membered cycloalkyl (e.g., cyclopropyl), 3- to 8-membered oxocycloalkyl (e.g., oxocyclobutyl), cyano, trifluoromethyl, $C_{1-6}$alkoxycarbonyl, $C_{1-6}$alkylamido, ureido group, carbamate, carboxyl and aryl;

$R_3$ and $R_4$ each independently is absent or represents H, $C_{1-6}$alkyl, $C_{1-6}$alkanoyl, $C_{1-6}$alkoxycarbonyl, glycosyl, aryl-$C_{1-6}$alkyl or aryl, wherein the $C_{1-6}$alkyl, $C_{1-6}$alkanoyl, $C_{1-6}$alkoxycarbonyl, glycosyl, aryl-$C_{1-6}$alkyl and aryl are unsubstituted or substituted with one or more (e.g., 1, 2, 3 or 4) substituents selected from the group consisting of halogen, hydroxy, amino, $C_{1-6}$alkyl, $C_{1-6}$alkoxy, $C_{1-6}$alkylamino and $C_{1-6}$alkanoyl; preferably, the aryl is 6- to 14-membered aryl, such as 6- to 10-membered aryl; more preferably phenyl or naphthyl;

R and R' each independently is selected from H, $C_{1-6}$alkyl, 3- to 8-membered cycloalkyl, aryl-$C_{1-6}$alkyl or aryl, wherein the $C_{1-6}$alkyl, 3- to 8-membered cycloalkyl, aryl-$C_{1-6}$alkyl and aryl are unsubstituted or substituted with one or more (e.g., 1, 2, 3 or 4) substituents selected from the group consisting of halogen, hydroxy, amino, $C_{1-6}$alkyl, $C_{1-6}$alkoxy, and $C_{1-6}$alkylamino;

R" represents $C_{1-6}$alkyl or aryl (e.g., 6- to 10-membered aryl group, preferably phenyl);

" ------- " in Formula (I) represents single bond or double bond; preferably, ring A contains 0, 1, 2 or 3 carbon-carbon double bonds; ring B contains 0, 1 or 2 carbon-carbon doubles bonds.

In a preferred embodiment of the invention, the sulfonate group is selected from the group consisting of sodium sulfonate, potassium sulfonate, calcium sulfonate, and magnesium sulfonate.

In a preferred embodiment of the invention, the 6- to 15-membered heteroaryl is selected from the group consisting of 9- to 15-membered fused heteroaryl; more preferably, the 6- to 15-membered heteroaryl is selected from 9- to 15-membered benzo-heteroaryl, for example, indolyl, benzofuranyl, benzothienyl, benzimidazolyl or quinolyl.

In a preferred embodiment, the bond between Y and the carbon atom attached thereto is a double bond, and Y represents O.

In a preferred embodiment, X represents NH; the bond between Y and the carbon atom attached thereto is a double bond, and Y represents O; $R_1$ represents an aryl substituted with one or more (e.g., 1, 2, 3 or 4) substituents selected from the group consisting of $C_{1-6}$alkyl and $C_{1-6}$alkoxy; preferably, the aryl group is a phenyl group or a naphthyl group; and $R_2$ represents H.

In a preferred embodiment, X represents O; the bond between Y and the carbon atom attached thereto is a double bond, and Y represents O; $R_1$ represents H; and $R_2$ represents H, sulfonate group or 6- to 15-membered heteroaryl; preferably, the sulfonate group is selected from the group consisting of sodium sulfonate, potassium sulfonate, calcium sulfonate and magnesium sulfonate; preferably, the 6- to 15-membered heteroaryl is selected from the group consisting of 9- to 15-membered fused heteroaryl; more preferably, the 6- to 15-membered heteroaryl is selected from the group consisting of 9- to 15-membered benzo-fused heteroaryl such as indolyl, benzofuranyl, benzothienyl, benzimidazolyl and quinolyl.

In a preferred embodiment, X represents O; the bond between Y and the carbon atom attached thereto is a double bond, Y represents O; $R_1$ represents $C_{1-6}$alkyl or aryl-$C_{1-6}$alkyl (preferably benzyl); $R_2$ represents H.

In a preferred embodiment, $R_3$ is absent and $R_4$ represents H. In a preferred embodiment, $R_3$ represents H and $R_4$ is absent. In a preferred embodiment, both $R_3$ and $R_4$ are H.

In a preferred embodiment, $R_3$ is absent, $R_4$ represents H, and ring A and ring B each have two carbon-carbon double bonds.

In a preferred embodiment, $R_3$ represents H, $R_4$ is absent, and ring A has 0, 1 or 2 carbon-carbon double bonds; further preferably, ring B has 0, 1 or 2 carbon-carbon double bonds.

In a preferred embodiment, $R_3$ and $R_4$ are both H and ring A contains 3 carbon-carbon double bonds (i.e., ring A is a benzene ring); further preferably, ring B contains 0 or 1 carbon-carbon double bond; more preferably, in ring B, Carbon 7 and Carbon 8 is linked with a carbon-carbon double bond.

In a preferred embodiment, neither $R_3$ nor $R_4$ is present. In such embodiments, in ring A, the bond between Carbon 2 and the O atom attached thereto is a carbon-oxygen double bond, and the bond between Carbon 3 and the O atom attached thereto is a carbon-oxygen double bond.

In a preferred embodiment, the bond between Carbon 7 and Carbon 8 is a carbon-carbon double bond. In a preferred embodiment, the bond between Carbon 7 and Carbon 8 is a carbon-carbon single bond.

In a preferred embodiment, the bond between Y and the carbon atom attached thereto is a double bond, and Y represents O.

In a preferred embodiment, X in the compound represents —NH—, —N(R)—, —O—, —CH$_2$— or halogen; R represents $C_{1-6}$alkyl or 3- to 8-membered cycloalkyl (preferably cyclohexyl); wherein, when X is halogen, $R_1$ is absent;

In a preferred embodiment, X represents —NH—, —N(R)—, —O— or halogen; R represents cyclohexyl.

In a preferred embodiment, $R_1$ in the compound is absent or represents hydrogen, $C_{1-4}$alkyl, —PO(OR)$_2$, monoglycosyl, $C_{1-4}$alkoxycarbonyl-$C_{1-4}$alkyl, 3- to 6-membered cycloalkyl-aminoacyl, aryl-$C_{1-4}$alkyl or aryl; wherein the $C_{1-4}$alkyl, monoglycosyl, $C_{1-4}$alkoxycarbonyl-$C_{1-4}$alkyl, 3- to 6-membered cycloalkyl-aminoacyl, aryl-$C_{1-4}$alkyl and aryl are unsubstituted or substituted with one or more (for example 1, 2, 3 or 4) substituents selected from the group consisting of: halogen, hydroxy, amino, $C_{1-4}$alkyl, $C_{1-4}$alkoxy, $C_{1-4}$alkylamino and $C_{1-4}$alkanoyl; preferably, the aryl is 6- to 14-membered aryl, for example 6- to 10-membered aryl; more preferably phenyl or naphthyl; R represents $C_{1-4}$alkyl.

In a preferred embodiment, $R_1$ is absent or represents hydrogen, $C_{1-4}$alkyl, —PO(OR)$_2$, glucosyl, $C_{1-2}$alkoxycarbonyl-$C_{1-2}$alkyl, cyclohexyl-aminoacyl, phenyl-$C_{1-2}$alkyl, naphthyl-$C_{1-2}$alkyl, phenyl or naphthyl; wherein the methyl, ethyl, glucosyl, $C_{1-2}$alkoxycarbonyl-$C_{1-2}$alkyl, cyclohexyl-aminoacyl, phenyl-$C_{1-2}$alkyl, naphthyl-$C_{1-2}$alkyl, phenyl or naphthyl are unsubstituted or substituted with one or more (e.g., 1, 2, 3 or 4) substituents selected from the group consisting of $C_{1-2}$alkyl, $C_{1-2}$alkoxy, and $C_{1-2}$alkanoyl;

R represents $C_{1-4}$alkyl.

In a preferred embodiment, $R_1$ is absent or represents hydrogen, $C_{1-4}$alkyl, —PO(OR)$_2$, phenyl-$C_{1-2}$alkyl, $C_{1-2}$alkoxycarbonyl-$C_{1-2}$alkyl, 3- to 6-membered cycloalkyl-aminoacyl;

R represents $C_{1-3}$alkyl.

In a preferred embodiment, $R_1$ is absent or represents hydrogen, methyl, ethyl, —PO(OMe)$_2$, —PO(OEt)$_2$, —PO(O$^i$Pr)$_2$, 2,3,4,6-tetraacetoxy-α-D-glucopyranosyl, EtO-COCH$_2$—, cyclohexyl-aminoacyl, benzyl, methoxyphenyl or tert-butylphenyl.

In a preferred embodiment, $R_2$ in the compound represents H, D, —OH, —PO(OR)$_2$, $C_{1-6}$alkyl, 9- to 15-membered fused heteroaryl or sulfonate; wherein the $C_{1-6}$alkyl or 6- to 15-membered heteroaryl is unsubstituted or substituted with one or more (for example 1, 2, 3 or 4) substituents selected from the group consisting of amino, halogen, hydroxy, oxy, $C_{1-6}$alkyl, $C_{1-6}$alkoxy, $C_{1-6}$alkanoyl, cyano, trifluoromethyl and carboxyl;

R represents H, $C_{1-6}$alkyl or aryl.

In a preferred embodiment, $R_2$ represents H, D, —PO(OR)$_2$, $C_{1-4}$alkyl, 9- to 15-membered benzo-fused heteroaryl or sulfonate; wherein the $C_{1-4}$alkyl or 9- to 15-membered benzo-fused heteroaryl is unsubstituted or substituted with one or more (e.g., 1, 2, 3 or 4) substituents selected from the group consisting of amino, halogen, hydroxy, oxy, $C_{1-4}$alkyl, $C_{1-4}$alkoxy, $C_{1-4}$alkanoyl, cyano, trifluoromethyl and carboxyl;

R represents H, $C_{1-4}$alkyl or phenyl.

In a preferred embodiment, $R_2$ represents H, D, —PO(OR)$_2$, $C_{1-4}$alkyl, 9- to 15-membered benzo-fused heteroaryl or sulfonate group; wherein the $C_{1-4}$alkyl and 9- to 15-membered benzo-fused heteroaryl are unsubstituted or substituted with one or more (e.g., 1, 2, 3 or 4) substituents selected from the group consisting of amino, halogen, hydroxy, oxy, $C_{1-4}$alkyl, $C_{1-4}$alkoxy, $C_{1-4}$alkanoyl, cyano, trifluoromethyl and carboxyl;

R represents H, $C_{1-4}$alkyl or phenyl.

In a preferred embodiment, $R_2$ represents H, D, —PO(OR)$_2$, 2-oxophenyl, indolyl or sodium sulfonate; wherein the indolyl is unsubstituted or substituted with one or more (e.g., 1, 2, 3 or 4) substituents selected from the group consisting of amino, fluoro, chloro, bromo, hydroxy, methyl, methoxy, formyl, cyano, trifluoromethyl and carboxyl;

R represents H, methyl, ethyl, isopropyl or phenyl.

In a preferred embodiment, the bond between Carbon 7 and Carbon 8 in the compound is a carbon-carbon double bond.

In a preferred embodiment, the bond between Y and the carbon atom attached thereto in the compound is a double bond.

In a preferred embodiment, the bond between Y and the carbon atom attached thereto in the compound is a single bond.

In a preferred embodiment, the compound has the following structure:

Formula (II)

wherein $R_3$ and $R_4$ each independently represents H, $C_{1-6}$alkyl or $C_{1-6}$alkanoyl;

preferably, $R_3$ and $R_4$ each independently represents H, $C_{1-4}$alkyl or $C_{1-4}$alkanoyl;

preferably, $R_3$ and $R_4$ each independently represents H, methyl or butyryl.

In a preferred embodiment, the compound has the structure:

Formula (III)

wherein $R_4$ represents H, $C_{1-6}$alkanoyl, $C_{1-6}$alkoxycarbonyl or monoglycosyl substituted with one or more (for example 1, 2, 3 or 4) $C_{1-6}$alkanoyl groups;

In a preferred embodiment, $R_4$ represents H, $C_{1-4}$alkanoyl, $C_{1-4}$alkoxycarbonyl or monoglycosyl substituted with one or more (e.g., 1, 2, 3 or 4) $C_{1-4}$alkanoyl groups;

In a preferred embodiment, $R_4$ represents H or $C_{1-2}$alkoxycarbonyl;

In a preferred embodiment, $R_4$ represents H, butyryl, ethoxycarbonyl or 2,3,4,6-tetraacetoxy-α-D-glucopyranosyl.

In a preferred embodiment, the compound is selected from the group consisting of:

XS0077
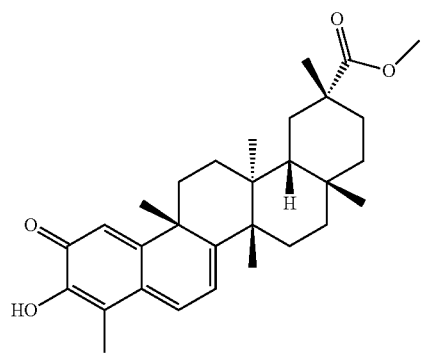
XS0287
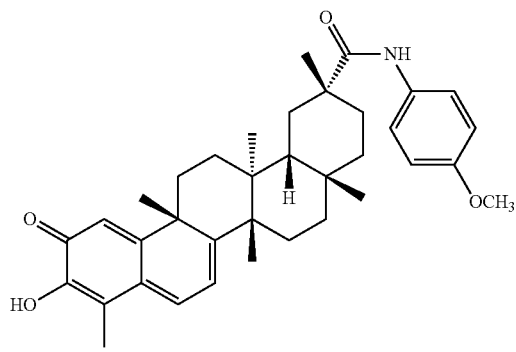
XS0284
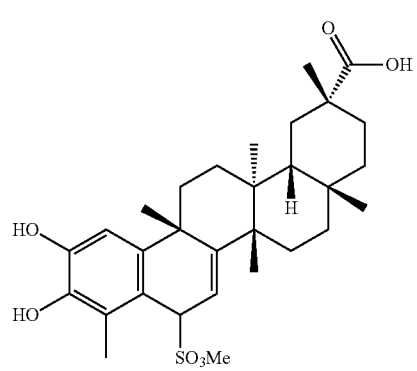
XS0335
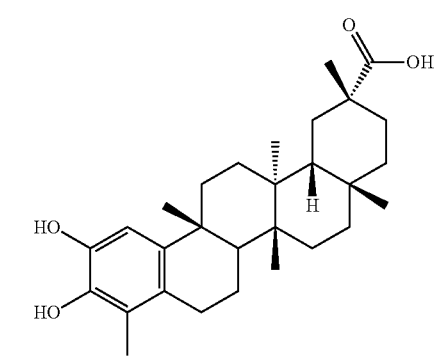
XS0285
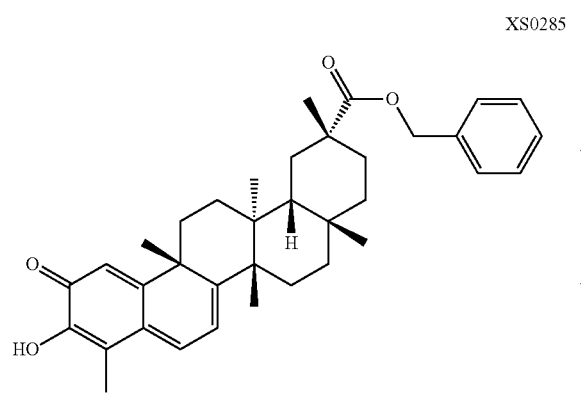
XS0366
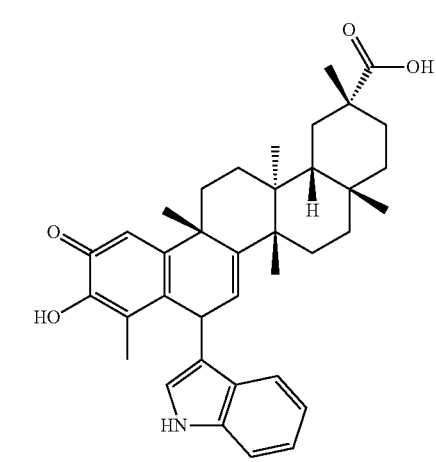
XS0286
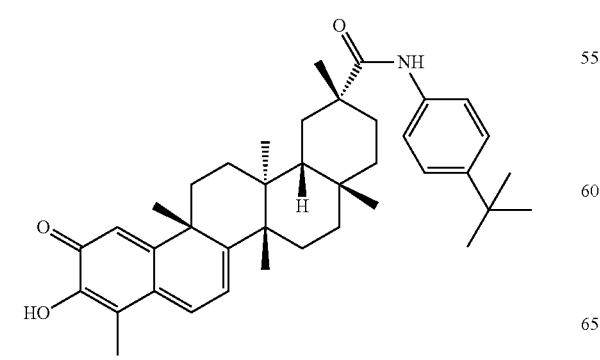
XS0394
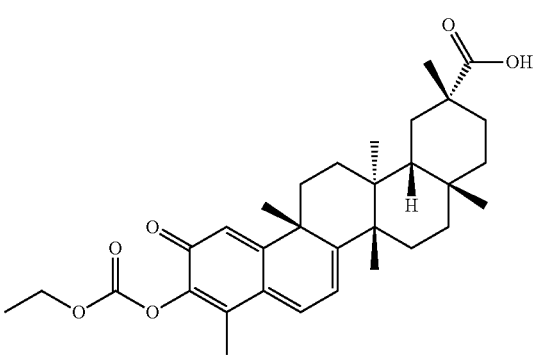

XS0395
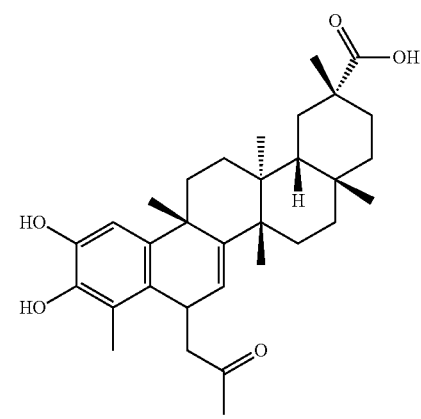
XS0418
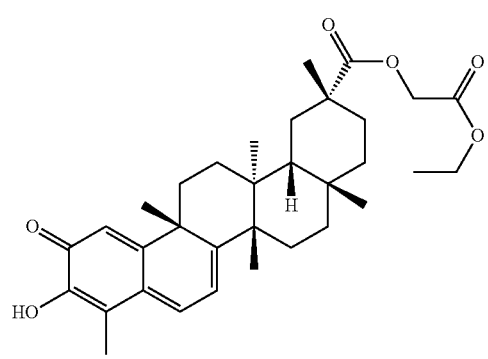
XS0419
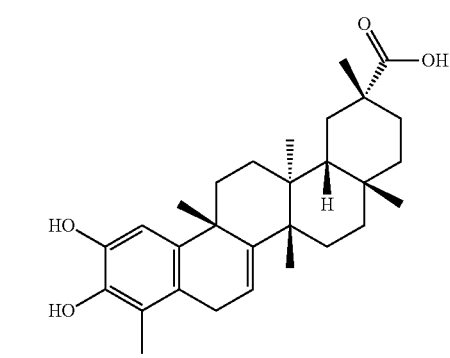
XS0421
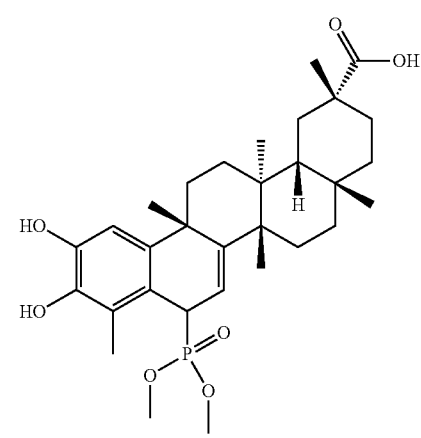
XS0434
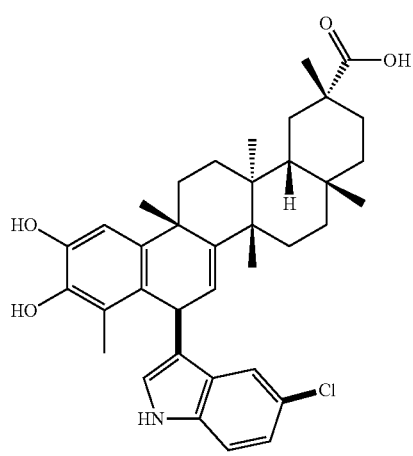
XS0435
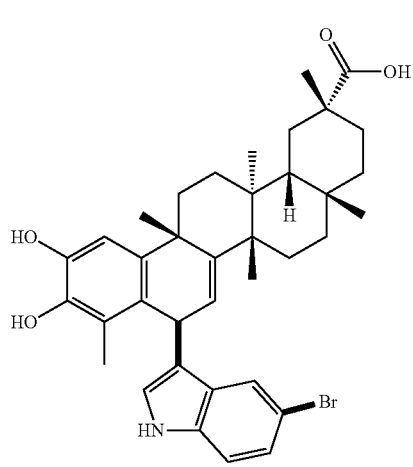
XS0436
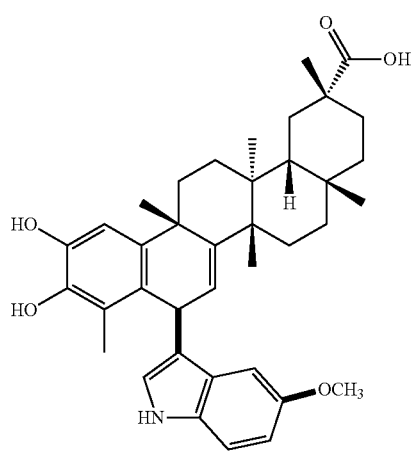

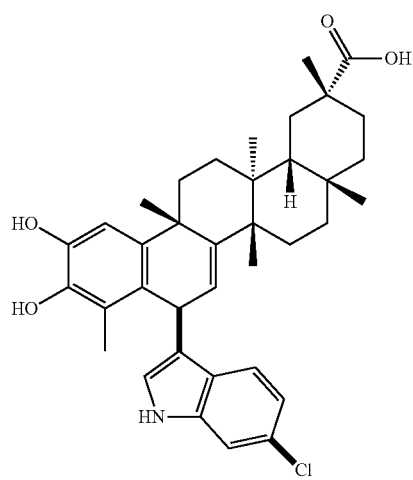
XS0437
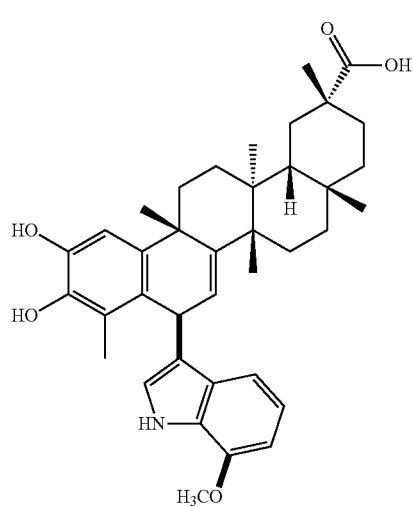
XS0438
XS0439
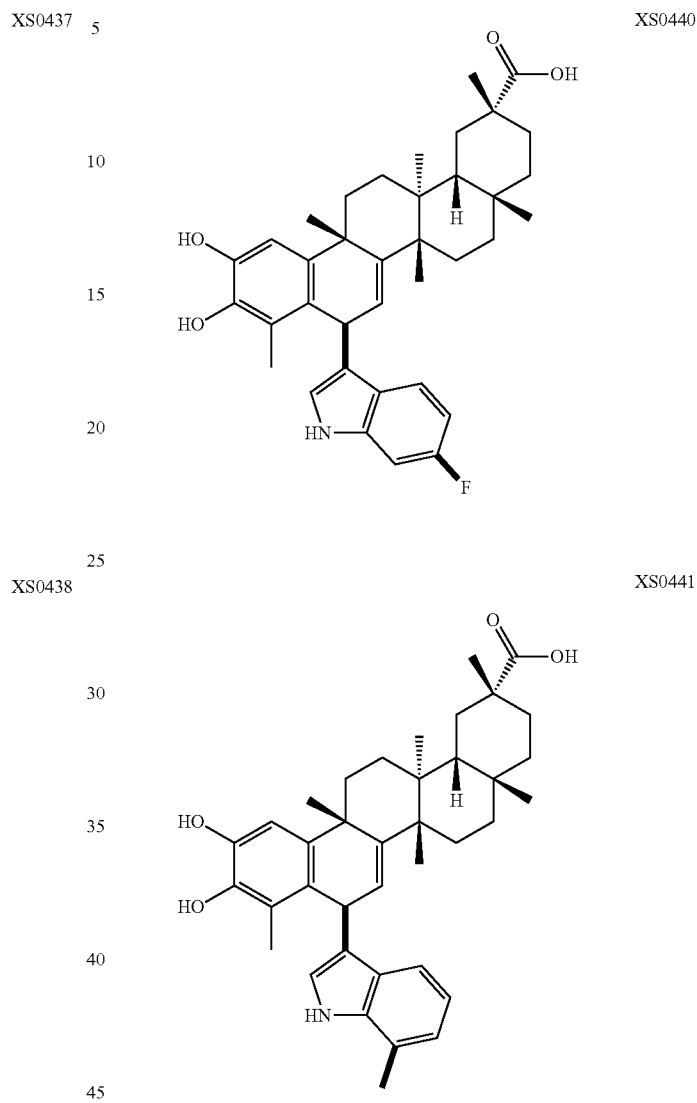
XS0440
XS0441
XS0442

-continued
XS0443
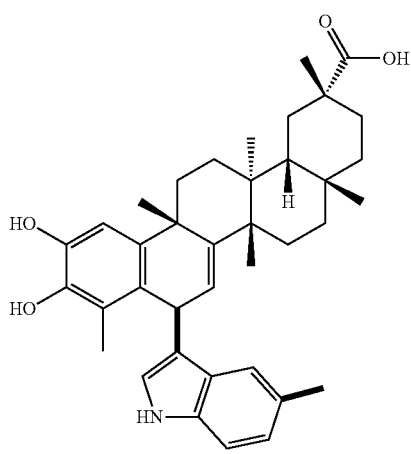
XS0444
XS0445
-continued
XS0446
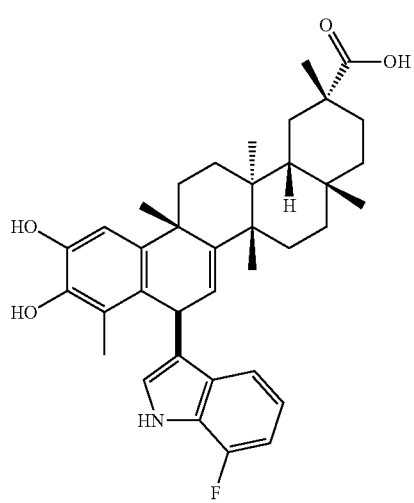
XS0447
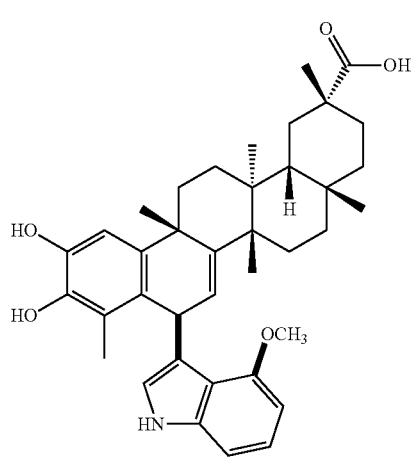
XS0448
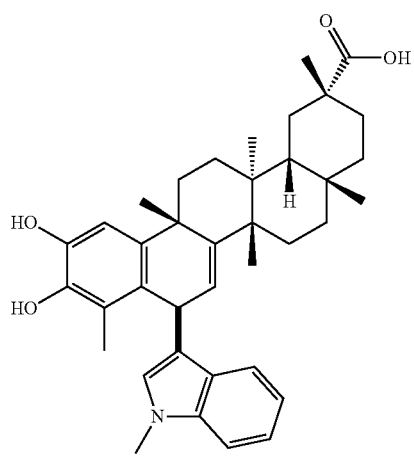

XS0449
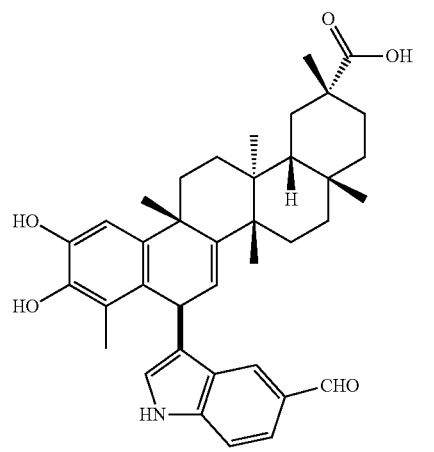
XS0457
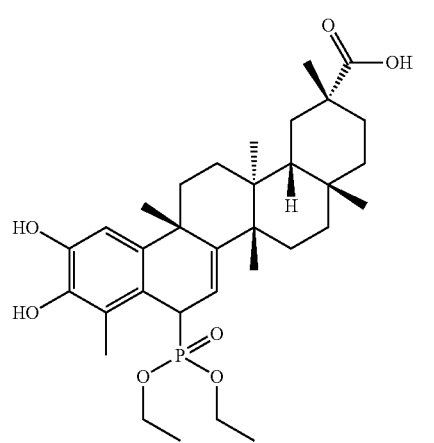
XS0462
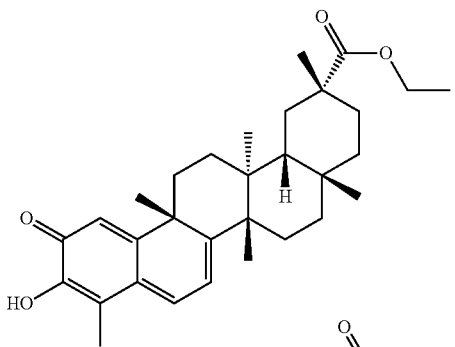
XS0463
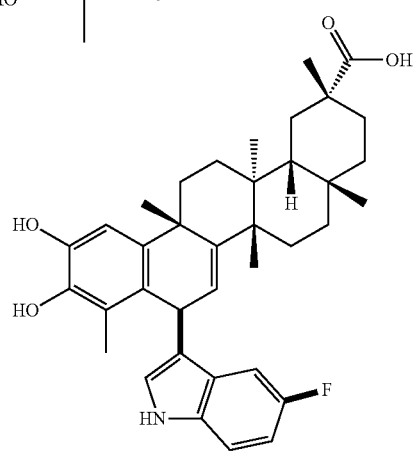
XS0464
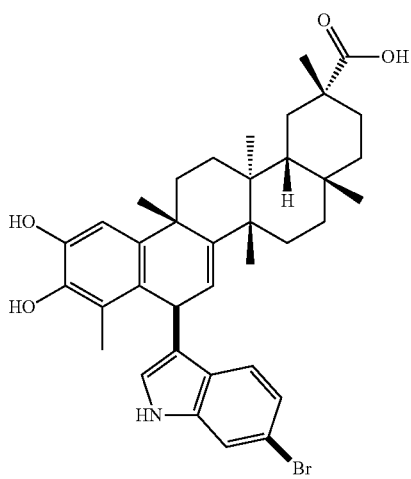
XS0473
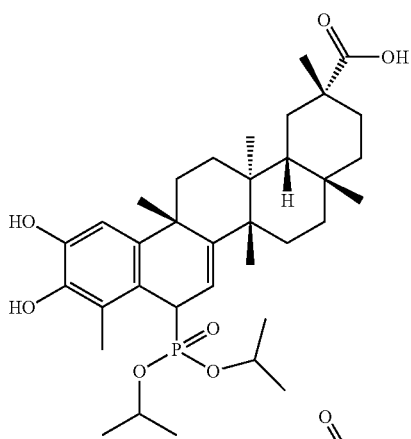
XS0474
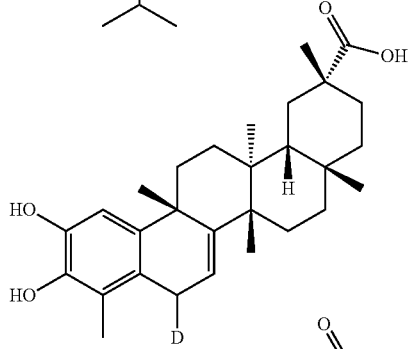
XS0478
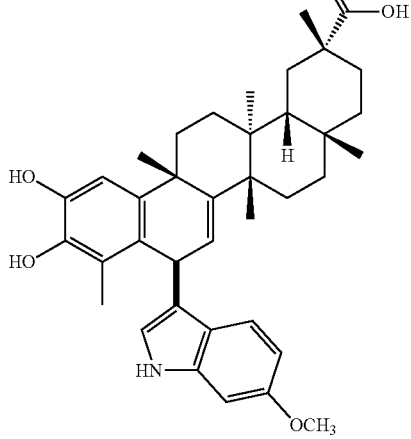

XS0479
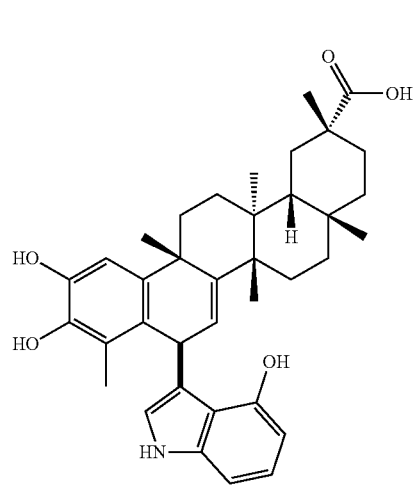
XS0487
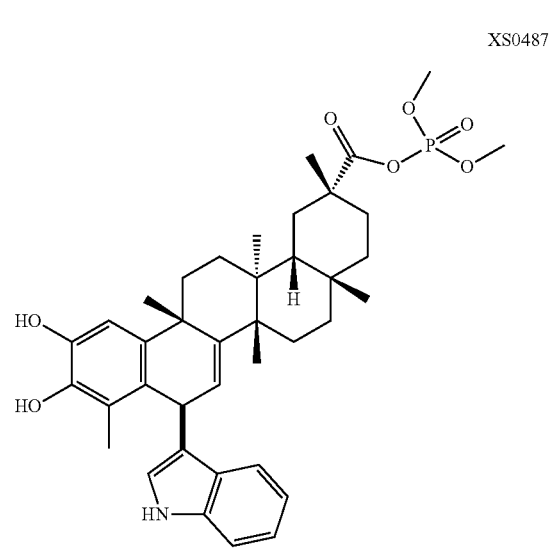
XS0480
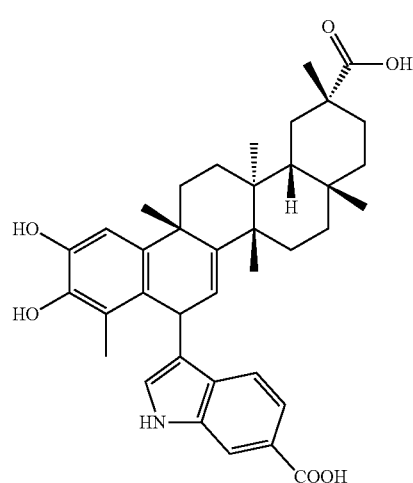
XS0488
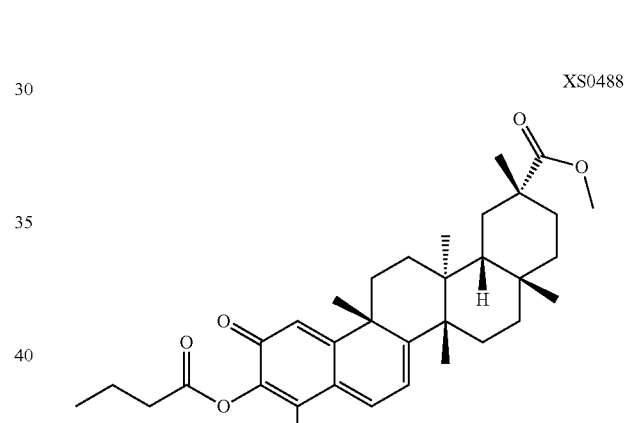
XS0486
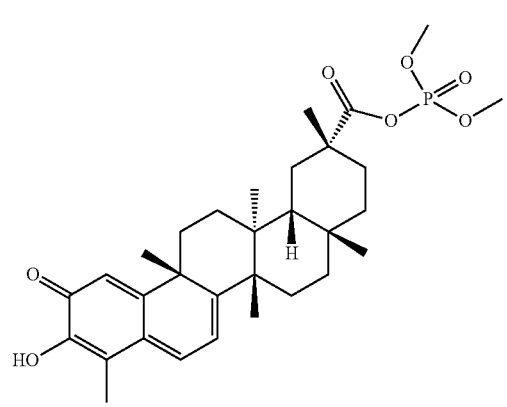
XS0490
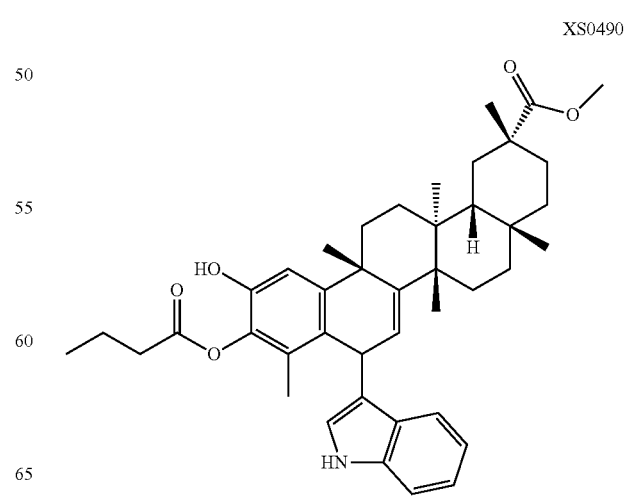

XS0491
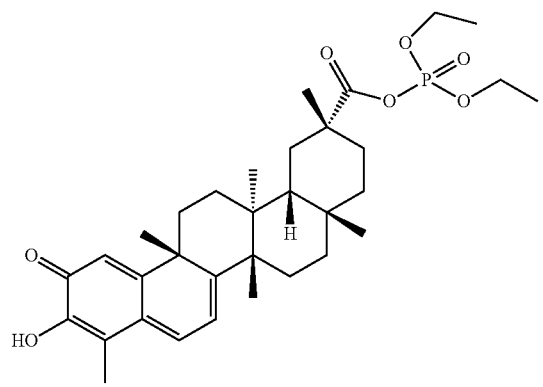
XS0492
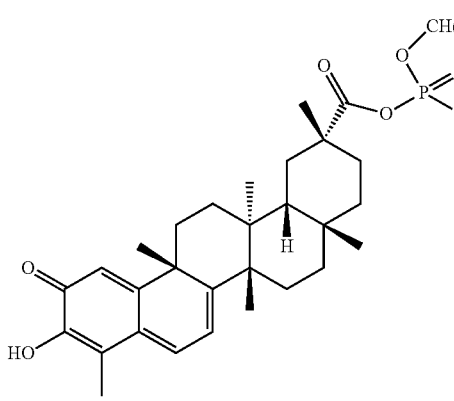
XS0493
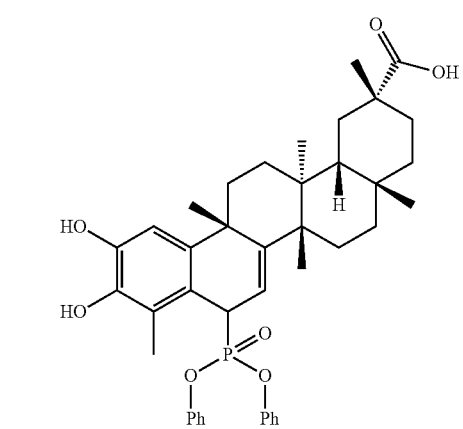
XS0503
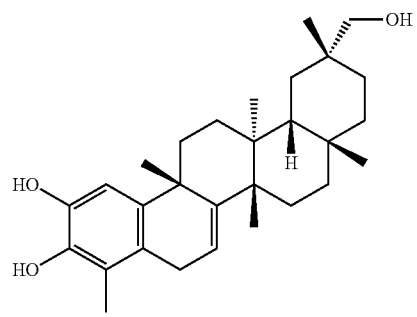
XS0506
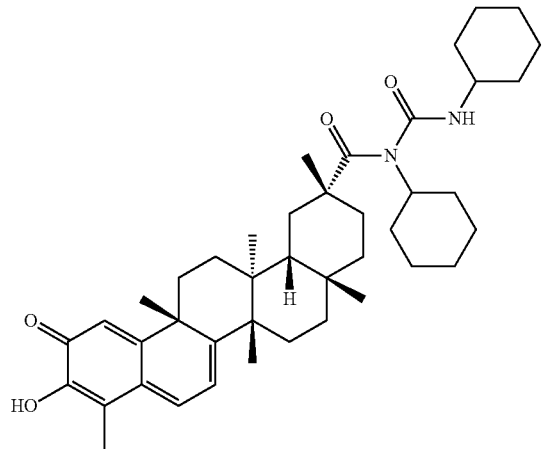
XS0507
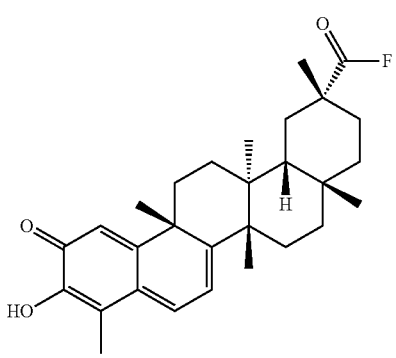
XS0508
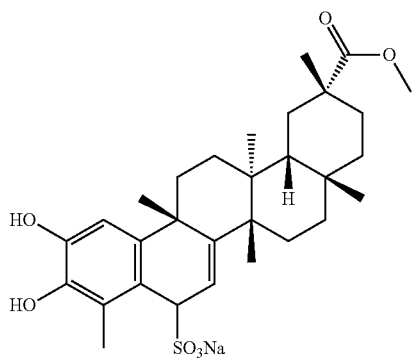
XS0509
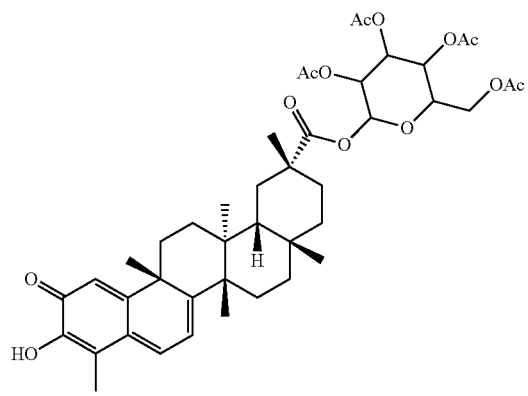

XS0514

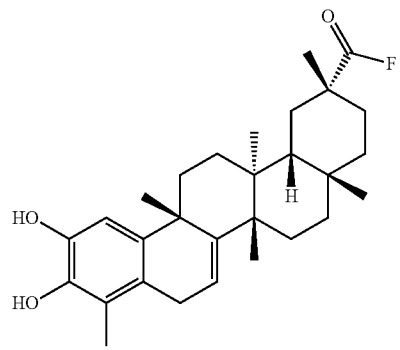

XS0515

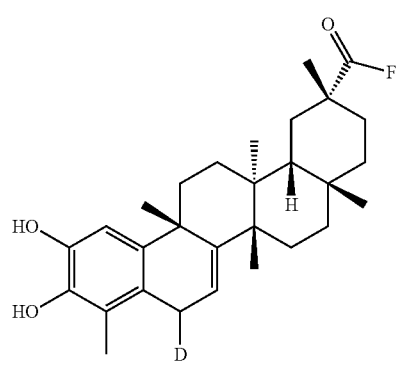

XS0516

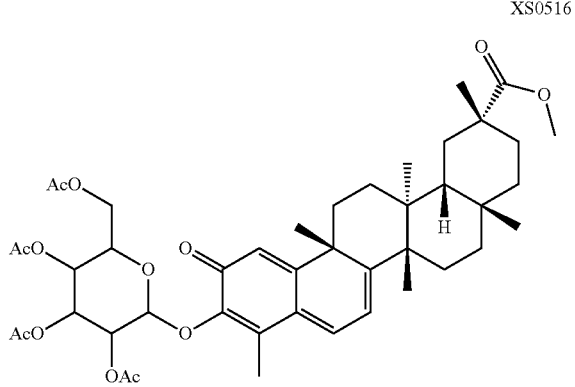

XS0534

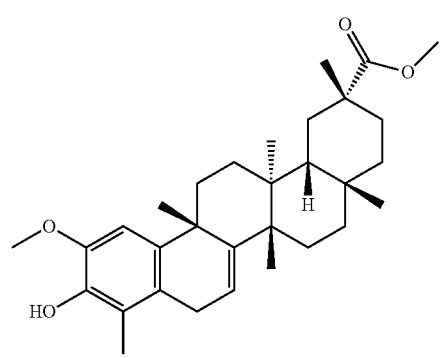

XS0536

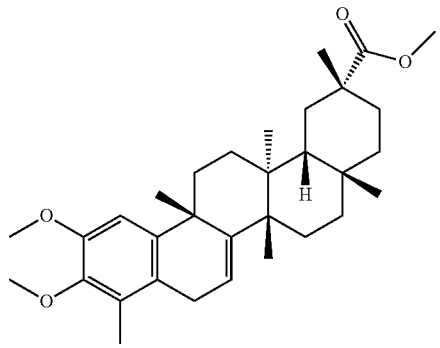

YXY101

In a preferred embodiment, the compound, or the tautomer, stereoisomer or pharmaceutically acceptable salt or ester thereof or the medicament is used as a ligand of orphan nuclear receptor Nur77, for inhibiting the transcriptional activity of Nur77. In a preferred embodiment, the compound, or the tautomer, stereoisomer or pharmaceutically acceptable salt or ester thereof or the medicament is used for inhibiting the transcriptional activity of Nur77 in a cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77, for inhibiting a biological effect of TNFα in a cell. In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77, for inhibiting mTOR pathway in a cell (e.g., down-regulating the activity of P-mTOR, p-P70S6K, and/or p-S6). In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77, for preventing or treating a Nur77-associated disease in a subject in need thereof.

In a preferred embodiment, the Nur77-associated disease is a cancer. For example, the compound, or the tautomer, stereoisomer or pharmaceutically acceptable salt or ester thereof or the medicament is used as a ligand of orphan nuclear receptor Nur77 for preventing or treating a Nur77-associated disease in a subject in need thereof. In a preferred embodiment, the Nur77-associated disease is a cancer (e.g., triple negative breast cancer).

In another aspect, the present application relates to a method for inhibiting the transcriptional activity of orphan nuclear receptor Nur77, comprising a step of contacting Nur77 with a compound of Formula I, or the tautomer, stereoisomer or pharmaceutically acceptable salt or ester thereof:

Formula (I)

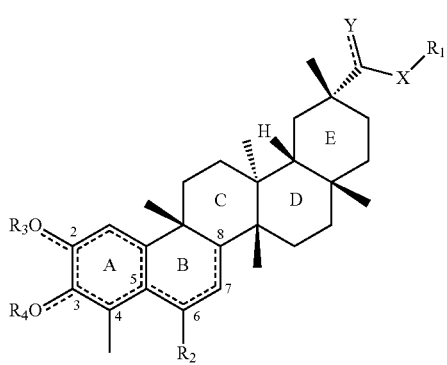

wherein, the atoms and substituents are as defined in the first aspect of the application.

In a preferred embodiment, the method is for inhibiting the transcriptional activity of Nur77 in a cell. In a preferred embodiment, the method comprises administering to a cell in need thereof an effective amount of the compound to inhibit the transcriptional activity of Nur77 in the cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting a biological effect of TNFα in a cell, comprising administering to the cell in need thereof an effective amount of a compound of Formula I, or a tautomer, a stereoisomer or a pharmaceutically acceptable salt or ester thereof:

(I)

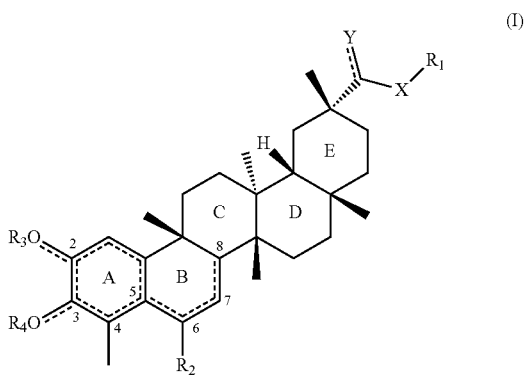

wherein, the atoms and substituents are as defined in the first aspect of the present application.

In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the method is for inhibiting TNFα-induced IκBα degradation. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting mTOR signaling pathway, comprising administering to a cell in need thereof an effective amount of a compound of Formula I, or a tautomer, a stereoisomer, or a pharmaceutically acceptable salt or ester thereof:

(I)

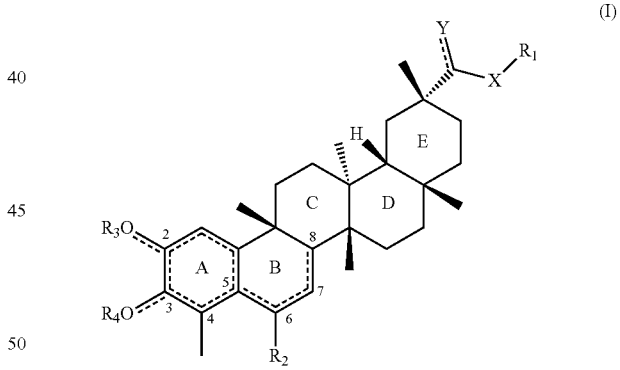

wherein, the atoms and substituents are as defined in the first aspect of the present application.

In a preferred embodiment, the compound, or the tautomer, stereoisomer or pharmaceutically acceptable salt or ester thereof or the medicament is for down-regulating the activity of P-mTOR, p-P70S6K and/or p-S6 in a cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for preventing or treating a Nur77-associated disease, comprising administering to a subject in need thereof an effective amount of a compound of Formula I, or a tautomer, a stereoisomer or a pharmaceutically acceptable salt or ester thereof:

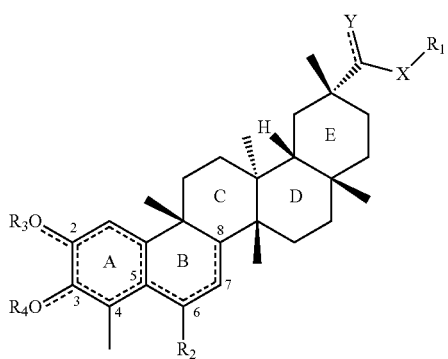

wherein, the atoms and substituents are as defined in the first aspect of the present application.

In a preferred embodiment, the Nur77-associated disease is a cancer (e.g., triple negative breast cancer).

In another aspect, the application relates to use of a compound shown below, or a tautomer, a stereoisomer or a pharmaceutically acceptable salt or ester thereof, which is used as a ligand of orphan nuclear receptor Nur77, or in the manufacture of a medicament as a ligand of orphan nuclear receptor Nur77:

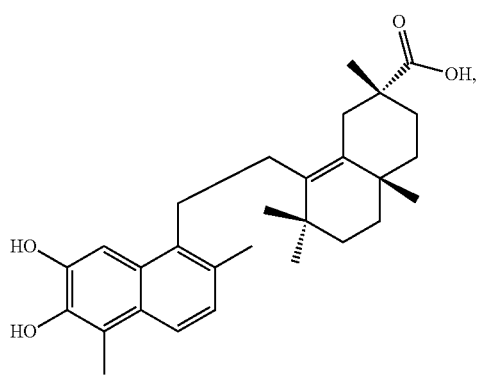

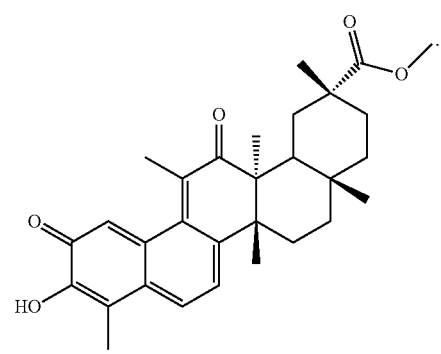

In a preferred embodiment, the compound, or the tautomer, the stereoisomer or the pharmaceutically acceptable salt or ester thereof or the medicament is used as a ligand of orphan nuclear receptor Nur77, for inhibiting the transcriptional activity of Nur77. In a preferred embodiment, the compound, or the tautomer, the stereoisomer or the pharmaceutically acceptable salt or ester thereof or the medicament is used for inhibiting the transcriptional activity of Nur77 in a cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, the stereoisomer or the pharmaceutically acceptable salt or ester thereof or the medicament is used as a ligand of orphan nuclear receptor Nur77, for inhibiting a biological effect of TNFα in a cell. In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77, for inhibiting mTOR pathway in a cell (e.g., down-regulating the activity of P-mTOR, p-P70S6K, and/or p-S6). In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, the stereoisomer or the pharmaceutically acceptable salt or ester thereof or the medicament is used as a ligand of orphan nuclear receptor Nur77, for preventing or treating a Nur77-associated disease in a subject in need thereof. In a preferred embodiment, the Nur77-associated disease is a cancer (e.g., triple negative breast cancer).

In another aspect, the present application relates to a method for inhibiting the transcriptional activity of orphan nuclear receptor Nur77, comprising a step of contacting Nur77 with a compound shown below, or a tautomer, a stereoisomer or a pharmaceutically acceptable salt or ester thereof:

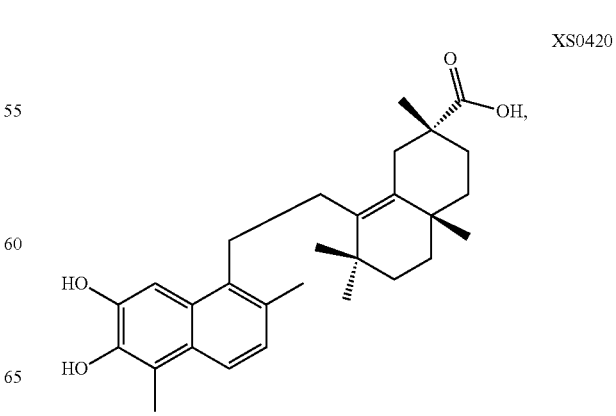

XS0502

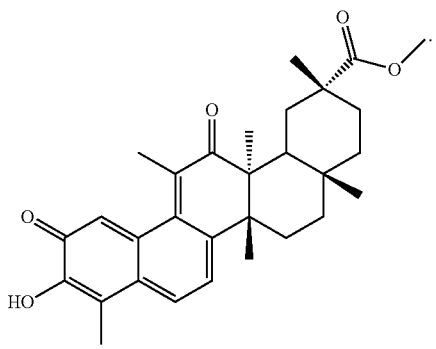

In a preferred embodiment, the method is for inhibiting the transcriptional activity of Nur77 in a cell. In a preferred embodiment, the method comprises administering to a cell in need thereof an effective amount of the compound, thereby inhibiting the transcriptional activity of Nur77 in the cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting a biological effect of TNFα in a cell, comprising administering to the cell in need thereof an effective amount of a compound shown below, or a tautomer, a stereoisomer or a pharmaceutically acceptable salt or ester thereof:

XS0420

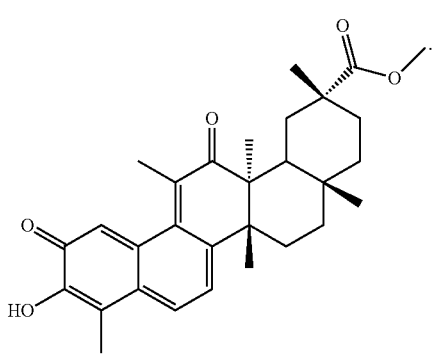

XS0502

In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the method is for inhibiting TNFα-induced IκBα degradation. In a preferred embodiment, the cell expresses Nur77. In a preferred embodiment, the cell is a cancer cell (e.g., a liver cancer cell, a cervical cancer cell, a lung cancer cell, a triple positive breast cancer cell, a colorectal cancer cell, or a prostate cancer cell).

In another aspect, the present application relates to a method for inhibiting mTOR pathway, comprising administering to a cell in need thereof an effective amount of a compound shown below, or a tautomer, a stereoisomer or a pharmaceutically acceptable salt or ester thereof:

XS0420

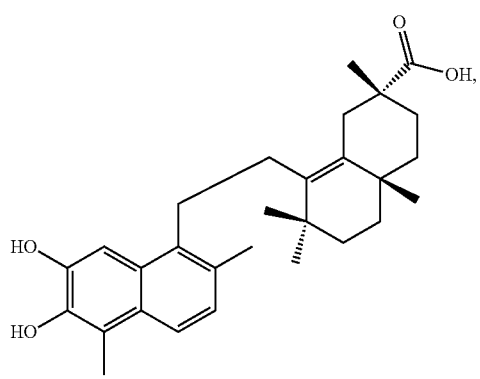

XS0502

In a preferred embodiment, the compound, or the tautomer, the stereoisomer or the pharmaceutically acceptable salt or ester thereof or the medicament is for down-regulating the activity of P-mTOR, p-P70S6K and/or p-S6 in a cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for preventing or treating a Nur77-associated disease, comprising administering to a subject in need thereof an effective amount of a compound shown below, or a tautomer, a stereoisomer or a pharmaceutically acceptable salt or ester thereof:

XS0420

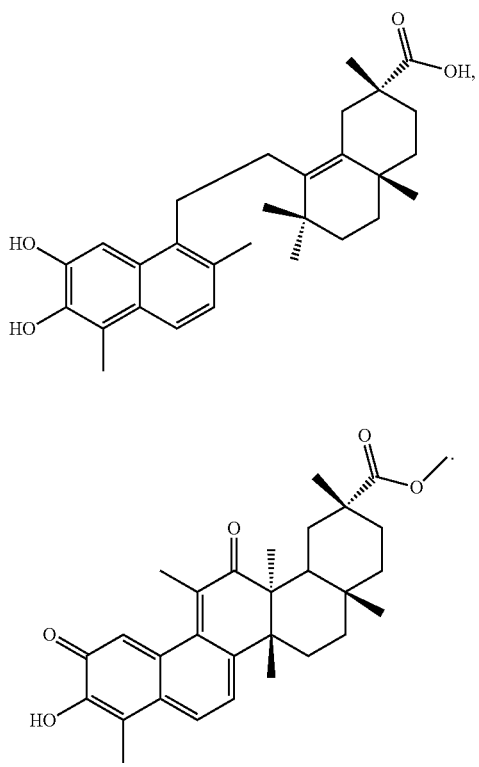

XS0502

In a preferred embodiment, the Nur77-associated disease is a cancer (e.g., triple negative breast cancer).

In another aspect, the application relates to a compound shown below, or a tautomer, a stereoisomer or a pharmaceutically acceptable salt or ester thereof:

Formula V

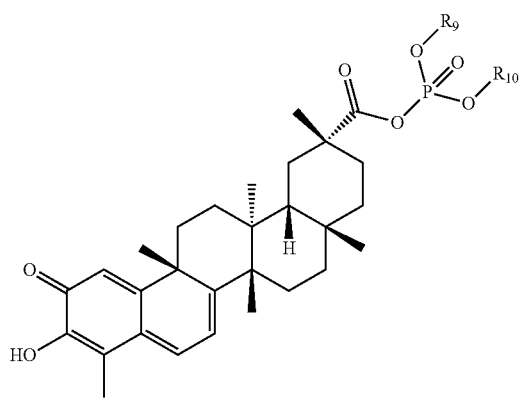

wherein, $R_9$ and $R_{10}$ each independently is selected from the group consisting of hydrogen, $C_{1-6}$alkyl and aryl;

preferably, $R_9$ and $R_{10}$ each independently is selected from the group consisting of hydrogen, $C_{1-4}$alkyl, phenyl and naphthyl;

preferably, $R_9$ and $R_{10}$ each independently is selected from the group consisting of methyl, ethyl and isopropyl.

In a preferred embodiment, the compound is selected from the group consisting of:

XS0486

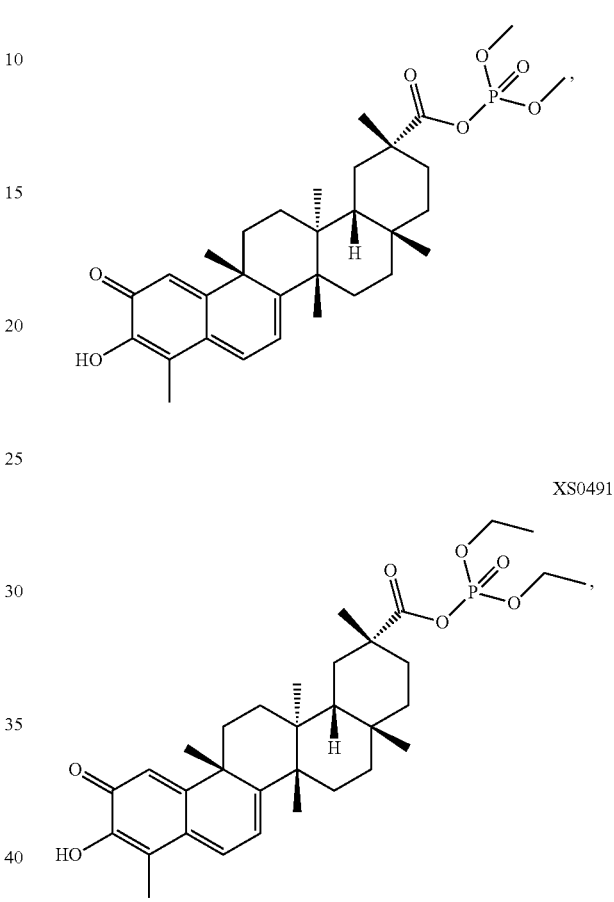

XS0491

XS0492

In another aspect, the application relates to use of a compound of Formula V, or a tautomer, a stereoisomer or a pharmaceutically acceptable salt or ester thereof, as a ligand of orphan nuclear receptor Nur77, or in the manufacture of a medicament as a ligand of orphan nuclear receptor Nur77:

Formula V

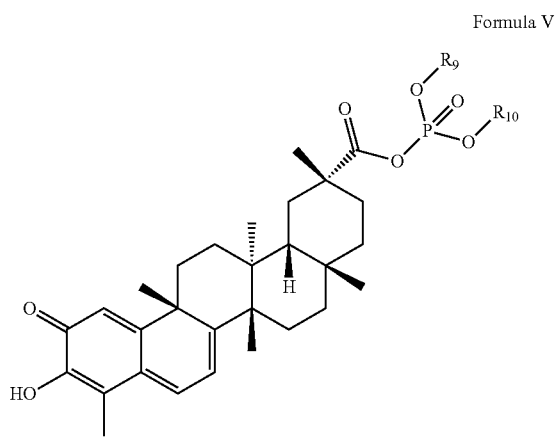

wherein, $R_9$ and $R_{10}$ each independently is selected from the group consisting of hydrogen, $C_{1-6}$alkyl and aryl;

preferably, $R_9$ and $R_{10}$ each independently is selected from the group consisting of hydrogen, $C_{1-4}$alkyl, phenyl and naphthyl;

preferably, $R_9$ and $R_{10}$ each independently is selected from the group consisting of methyl, ethyl and isopropyl.

In a preferred embodiment, the compound is selected from the group consisting of:

XS0486
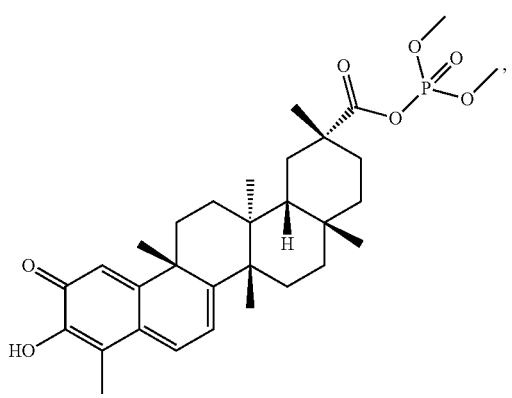

XS0491
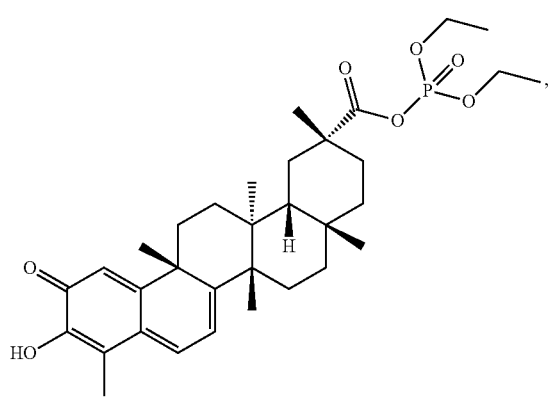

XS0492
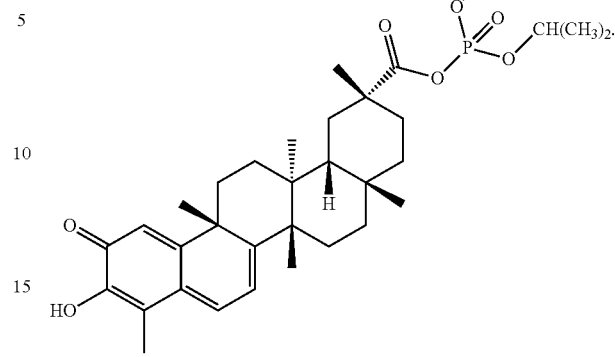

In a preferred embodiment, the compound, or the tautomer, stereoisomer or pharmaceutically acceptable salt or ester thereof or the medicament is used as a ligand of orphan nuclear receptor Nur77, for inhibiting the transcriptional activity of Nur77. In a preferred embodiment, the compound, or the tautomer, stereoisomer or pharmaceutically acceptable salt or ester thereof or the medicament is used for inhibiting the transcriptional activity of Nur77 in vivo, in vitro or ex vivo. In a preferred embodiment, the compound, or the tautomer, stereoisomer or pharmaceutically acceptable salt or ester thereof or the medicament is used for inhibiting the transcriptional activity of Nur77 in a cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77 for inhibiting a biological effect of TNFα in a cell. In a preferred embodiment, the compound, or the tautomer, stereoisomer or pharmaceutically acceptable salt or ester thereof or the medicament is used for inhibiting a biological effect of TNFα in a cell, in vivo, in vitro or ex vivo. In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the compound, or the tautomer, stereoisomer or pharmaceutically acceptable salt or ester thereof or the medicament is used for inhibiting TNFα-induced IκBα degradation. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77 for inhibiting mTOR pathway in a cell (e.g., down-regulating the activity of P-mTOR, p-P70S6 and/or p-S6). In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77, for preventing or treating a Nur77-associated disease in a subject in need thereof.

In a preferred embodiment, the Nur77-associated disease is a cancer. In a preferred embodiment, the compound, or the tautomer, stereoisomer or pharmaceutically acceptable salt or ester thereof or the medicament is used for inhibiting the proliferation and/or metastasis of a cancer cell, and/or for promoting the apoptosis of a cancer cell, in a subject having a cancer. In a preferred embodiment, the cancer is selected from the group consisting of liver cancer, cervical cancer, lung cancer, and breast cancer. In a preferred embodiment, the cancer is triple negative breast cancer (i.e., breast cancer with negative estrogen receptor (ER), progesterone receptor (PR) and proto-oncogene Her-2). In a preferred embodiment, the medicament is used for treating a cancer and comprises the compound, or the tautomer, stereoisomer or pharmaceutically acceptable salt or ester thereof, as well as TNFα.

In another aspect, the present application relates to a method for inhibiting the transcriptional activity of orphan nuclear receptor Nur77, comprising a step of contacting Nur77 with a compound of Formula V, or a tautomer, a stereoisomer or a pharmaceutically acceptable salt or ester thereof:

Formula V

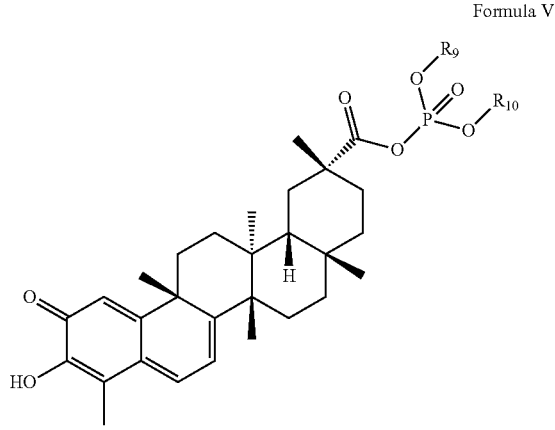

wherein, $R_9$ and $R_{10}$ are each independently selected from the group consisting of hydrogen, $C_{1-6}$alkyl and aryl;

preferably, $R_9$ and $R_{10}$ are each independently selected from the group consisting of hydrogen, $C_{1-4}$alkyl, phenyl and naphthyl;

preferably, $R_9$ and $R_{10}$ are each independently selected from the group consisting of methyl, ethyl and isopropyl.

In a preferred embodiment, the compound is selected from the group consisting of:

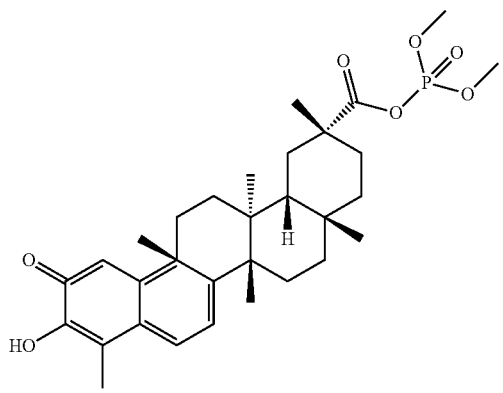

XS0486

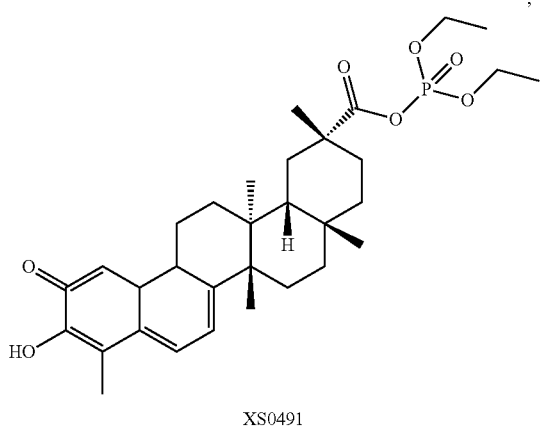

XS0491

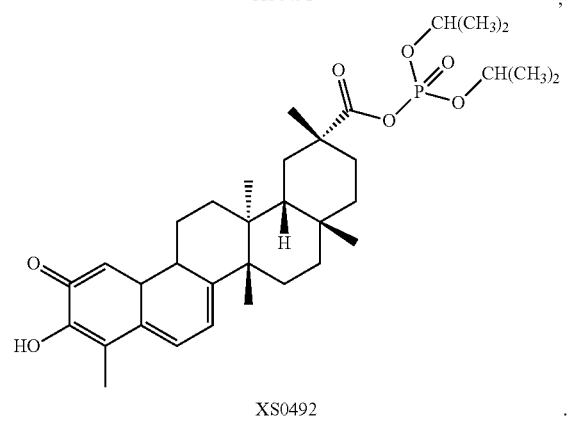

XS0492

In a preferred embodiment, the method is for inhibiting the transcriptional activity of Nur77 in a cell. In a preferred embodiment, the method comprises administering to a cell in need thereof an effective amount of the compound so as to inhibit the transcriptional activity of Nur77 in the cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting a biological effect of TNFα in a cell, comprising administering to the cell in need thereof an effective amount of a compound of Formula V, or a tautomer, a stereoisomer or a pharmaceutically acceptable salt or ester thereof:

Formula V

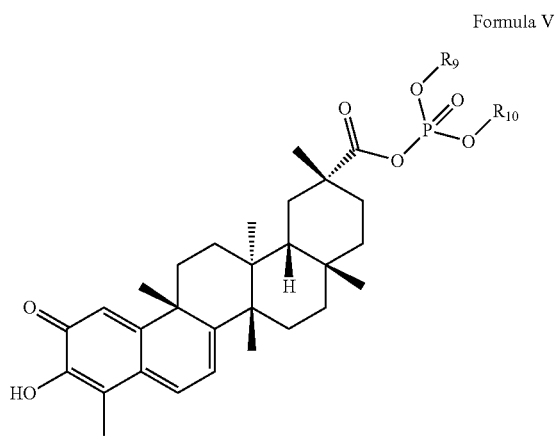

wherein, $R_9$ and $R_{10}$ are each independently selected from the group consisting of hydrogen, $C_{1-6}$alkyl and aryl.

In a preferred embodiment, $R_9$ and $R_{10}$ are each independently selected from the group consisting of hydrogen, $C_{1-4}$alkyl, phenyl, and naphthyl.

In a preferred embodiment, $R_9$ and $R_{10}$ are each independently selected from the group consisting of methyl, ethyl, and isopropyl.

In a preferred embodiment, the compound is selected from the group consisting of:

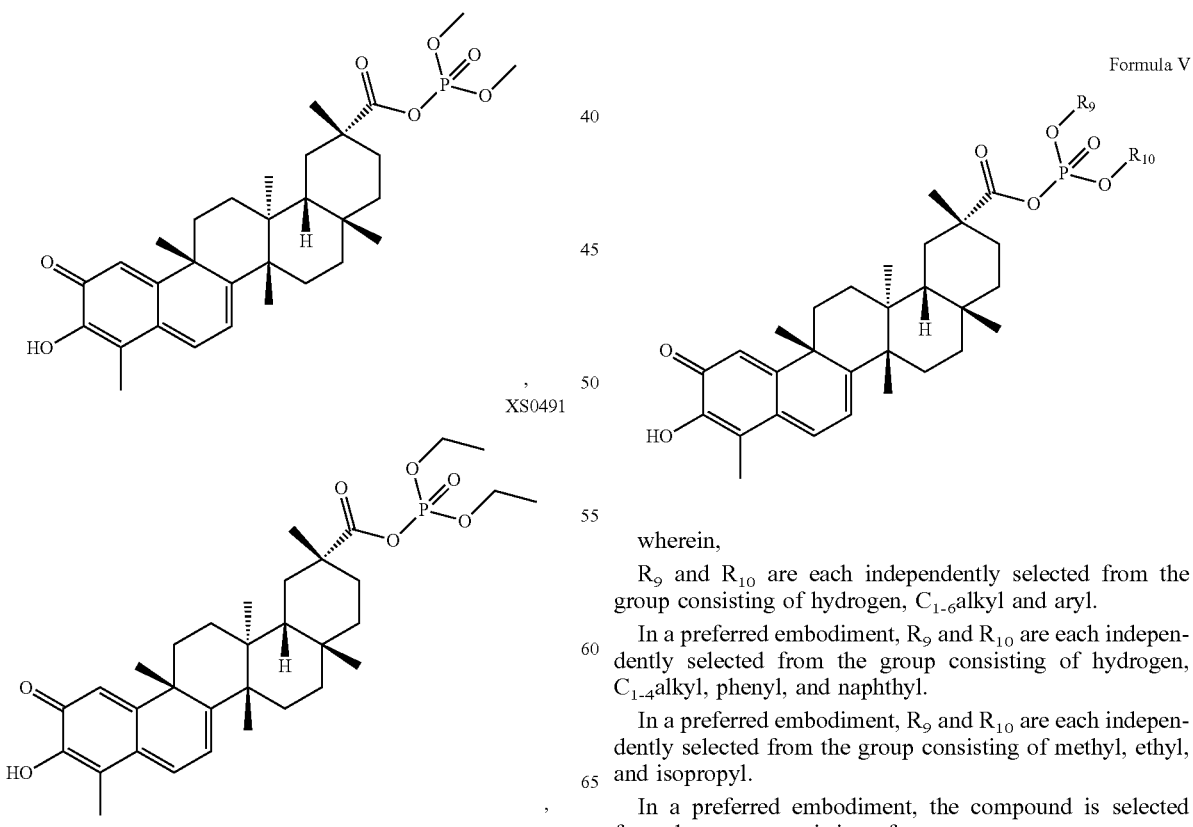

In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the method is for inhibiting TNFα-induced IκBα degradation. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting mTOR pathway, comprising administering to a cell in need thereof an effective amount of a compound of Formula V, or a tautomer, a stereoisomer or a pharmaceutically thereof acceptable salt or ester:

Formula V

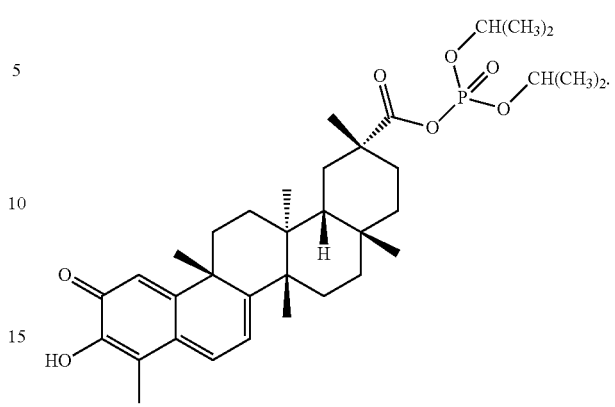

wherein, $R_9$ and $R_{10}$ are each independently selected from the group consisting of hydrogen, $C_{1-6}$alkyl and aryl.

In a preferred embodiment, $R_9$ and $R_{10}$ are each independently selected from the group consisting of hydrogen, $C_{1-4}$alkyl, phenyl, and naphthyl.

In a preferred embodiment, $R_9$ and $R_{10}$ are each independently selected from the group consisting of methyl, ethyl, and isopropyl.

In a preferred embodiment, the compound is selected from the group consisting of:

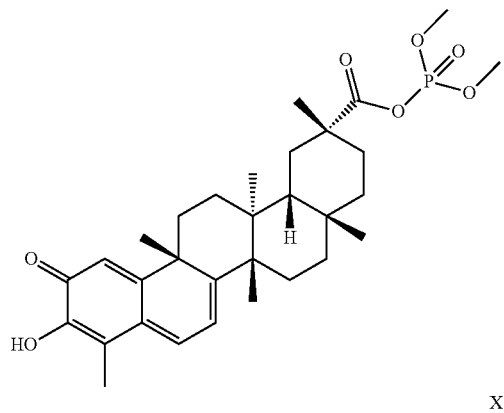

XS0486

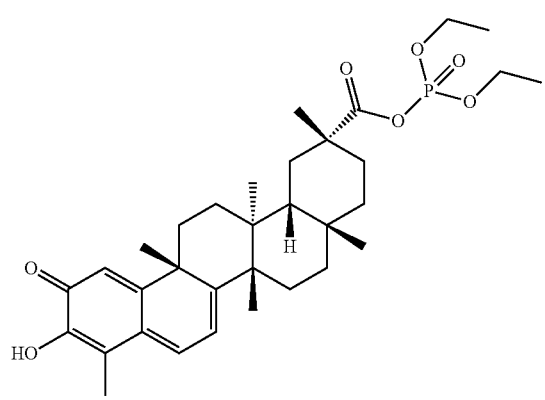

XS0491

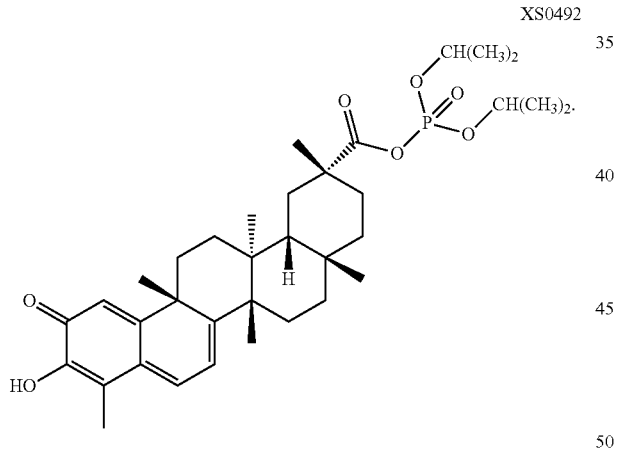

XS0492

In a preferred embodiment, the compound, or the tautomer, stereoisomer or pharmaceutically acceptable salt or ester thereof or the medicament is used for down-regulating the activity of P-mTOR, p-P70S6K and/or p-S6. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for preventing or treating a Nur77-associated disease, comprising: administering to a subject in need thereof an effective amount of a compound of Formula V, or a tautomer, a stereoisomer or a pharmaceutically acceptable salt or ester thereof:

Formula V wherein, $R_9$ and $R_{10}$ are each independently selected from the group consisting of hydrogen, $C_{1-6}$alkyl and aryl.

In a preferred embodiment, $R_9$ and $R_{10}$ are each independently selected from the group consisting of hydrogen, $C_{1-4}$alkyl, phenyl, and naphthyl.

In a preferred embodiment, $R_9$ and $R_{10}$ are each independently selected from the group consisting of methyl, ethyl, and isopropyl.

In a preferred embodiment, the compound is selected from the group consisting of:

XS0486

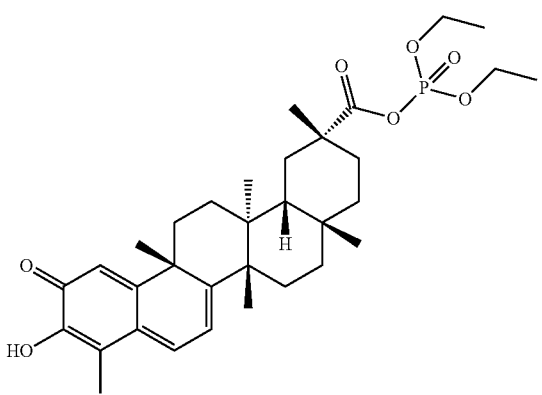

XS0491

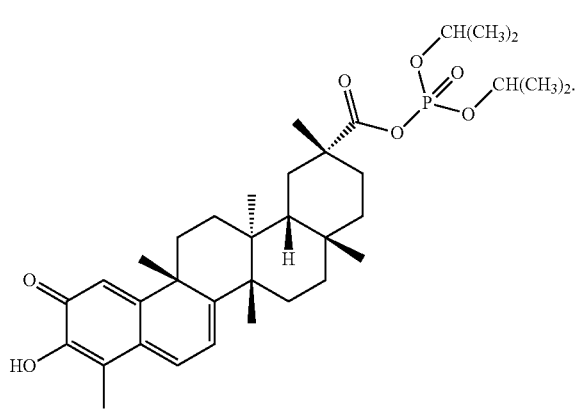

XS0492

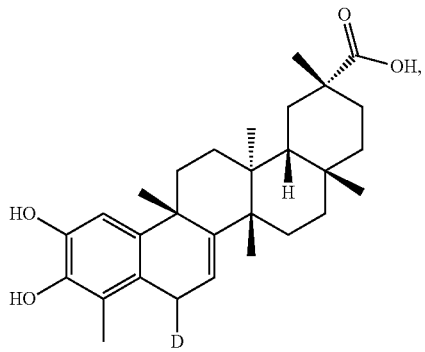

XS0474

In a preferred embodiment, the Nur77-associated disease is a cancer (e.g., triple negative breast cancer).

In another aspect, the application relates to a compound shown below, or a tautomer, a stereoisomer or a pharmaceutically acceptable salt or ester thereof:

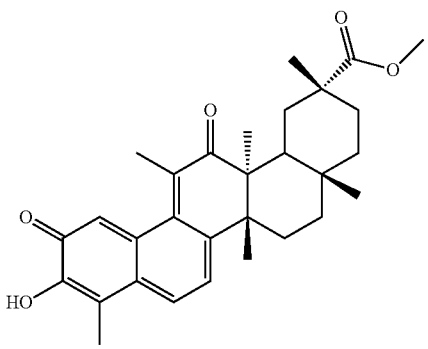

XS0502

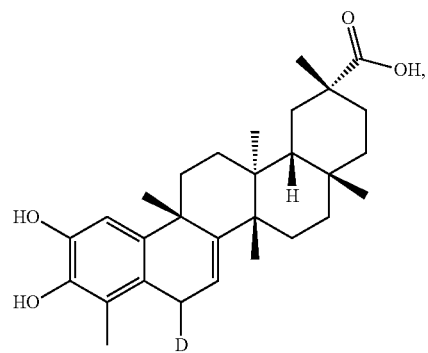

XS0474

In another aspect, the application relates to use of a compound shown below, or a tautomer, a stereoisomer or a pharmaceutically acceptable salt or ester thereof, which is used as a ligand of orphan nuclear receptor Nur77, or in the manufacture of a medicament as a ligand of orphan nuclear receptor Nur77:

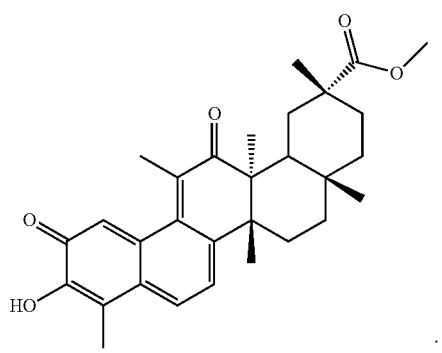

XS0502

In a preferred embodiment, the compound, or the tautomer, stereoisomer or pharmaceutically acceptable salt or ester thereof or the medicament is used as a ligand of orphan nuclear receptor Nur77 for inhibiting the transcriptional activity of Nur77. In a preferred embodiment, the compound, or the tautomer, stereoisomer or pharmaceutically acceptable salt or ester thereof or the medicament is used for inhibiting the transcription activity of Nur77 in vivo, in vitro or ex vivo. In a preferred embodiment, the compound, or the tautomer, stereoisomer or pharmaceutically acceptable salt or ester thereof or the medicament is used for inhibiting the transcriptional activity of Nur77 in a cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77 for inhibiting a biological effect of TNFα in a cell. In a preferred embodiment, the compound, or the tautomer, stereoisomer or pharmaceutically acceptable salt or ester thereof or the medicament is used for inhibiting a biological effect of TNFα in a cell, in vivo, in vitro or ex vivo. In a preferred embodiment, the biological effect of TNFα is phosphorylation of κB inhibitory protein (IκB) kinase α/β (IKKα/β), degradation of IκBα, nuclear import of the p65 subunit of NF-κB, and/or activation of NF-κB. In a preferred embodiment, the compound, or the tautomer, stereoisomer or pharmaceutically acceptable salt or ester thereof or the medicament is used for inhibiting TNFα-induced IκBα degradation. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77 for inhibiting mTOR pathway in a cell (e.g., down-regulating activity of P-mTOR, p-P70S6 and/or p-S6). In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In a preferred embodiment, the compound, or the tautomer, stereoisomer or pharmaceutically acceptable salt or ester thereof or the medicament is used as a ligand of orphan nuclear receptor Nur77, for preventing or treating a Nur77-associated disease in a subject in need thereof. In a preferred embodiment, the Nur77-associated disease is a cancer. In a preferred embodiment, the compound, or the tautomer, stereoisomer or pharmaceutically acceptable salt or ester thereof or the medicament is used for inhibition proliferation and/or metastasis and/or promotion of apoptosis of a cancer cell in a subject having cancer. In a preferred embodiment, the cancer is selected from the group consisting of liver cancer, cervical cancer, lung cancer, and breast cancer. In a preferred embodiment, the cancer is triple negative breast cancer (i.e., breast cancer with negative estrogen receptor (ER), progesterone receptor (PR), and proto-oncogene Her-2). In a preferred embodiment, the medicament is used for treating a cancer and comprises the compound, or the tautomer, stereoisomer or pharmaceutically acceptable salt or ester thereof, as well as TNFα.

In another aspect, the present application relates to a method for inhibiting the transcriptional activity of orphan nuclear receptor Nur77, comprising a step of contacting Nur77 with a compound shown below, or a tautomer, a stereoisomer or a pharmaceutically acceptable salt or ester thereof:

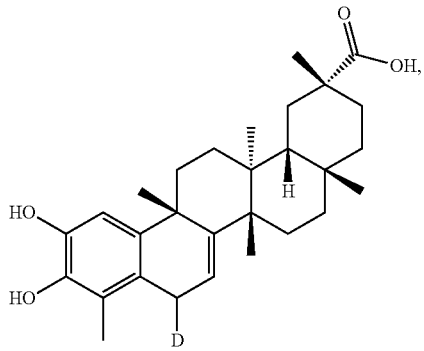
XS0474

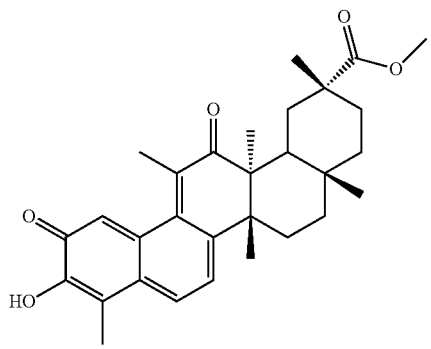
XS0502

In a preferred embodiment, the method is for inhibiting the transcriptional activity of Nur77 in a cell. In a preferred embodiment, the method comprises administering to a cell in need thereof an effective amount of the compound so as to inhibit transcriptional activity of Nur77 in the cell. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting a biological effect of TNFα in a cell, comprising administering to the cell in need thereof an effective amount of a compound shown below, or a tautomer, a stereoisomer or a pharmaceutically acceptable salt or ester thereof:

XS0474

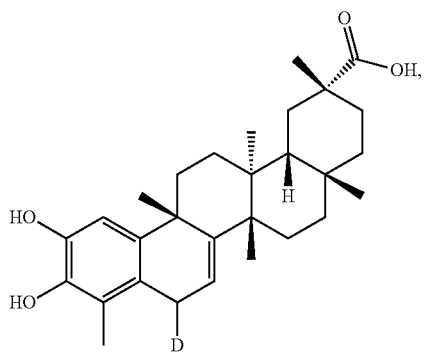
XS0502

In a preferred embodiment, the biological effect of TNFα is phosphorylation of κB inhibitory protein (IκB) kinase α/β

(IKKα/β), degradation of IκBα, nuclear import of the p65 subunit of NF-κB, and/or activation of NF-κB. In a preferred embodiment, the method is for inhibiting TNFα-induced IκBα degradation. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for inhibiting mTOR pathway, comprising administering to a cell in need thereof an effective amount of a compound shown below, or a tautomer, a stereoisomer or a pharmaceutically acceptable salt or ester thereof:

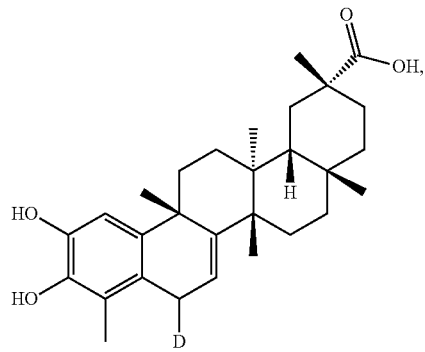
XS0474

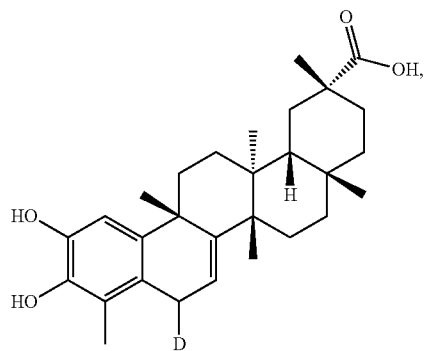
XS0474

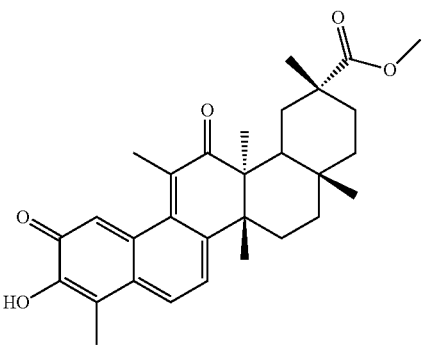
XS0502

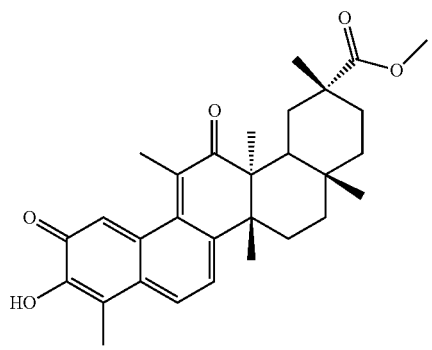
XS0502

In a preferred embodiment, the compound, or the tautomer, stereoisomer or pharmaceutically acceptable salt or ester thereof or the medicament is for down-regulating the activity of P-mTOR, p-P70S6K and/or p-S6. In a preferred embodiment, the cell expresses Nur77. In a preferred embodiment, the cell is selected from a triple negative breast cancer cell and other cancer cells (e.g., a liver cancer cell, a cervical cancer cell, a lung cancer cell, a triple positive breast cancer cell, a colorectal cancer cell, or a prostate cancer cell).

In another aspect, the present application relates to a method for preventing or treating a Nur77-associated disease, comprising administering to a subject in need thereof an effective amount of a compound shown below, or a tautomer, a stereoisomer or a pharmaceutically acceptable salt or ester thereof:

In a preferred embodiment, the Nur77-associated disease is a cancer (e.g., triple negative breast cancer).

In another aspect, the present application relates to a method for screening a drug having anticancer activity, comprising the steps of:

(1) providing a cancer cell expressing orphan nuclear receptor Nur77 (for example, a triple negative breast cancer cell), and setting up a negative control (i.e., not expressing Nur77);

(2) treating the cell with TNFα and a candidate agent;

(3) detecting (e.g., detecting by immunoblotting method) the levels of P-mTOR, p-P70S6K and p-S6 in the treated cell;

(4) comparing the levels of corresponding proteins in the cell and the negative control cell, and determining the candidate agent has anticancer activity if there is a decrease in at least one of the protein levels.

Advantageous Effects of the Invention (1) The present inventors have found for the first time that a compound represented by Formula I to Formula V can target orphan nuclear receptor Nur77 and function as a ligand thereof. For example, such a compound can be used to reduce or inhibit the activity (e.g., transcriptional activity) of orphan nuclear receptor Nur77.

(2) The inhibition of mTOR signaling pathway can be used as an effective indicator for screening anticancer drugs. The present inventors have found that compounds strongly inhibiting the mTOR signaling pathway via Nur77 have potential anticancer activity. Thus, the present application also provides a method for screening a drug having anticancer (especially triple negative breast cancer) activity.

(3) Compounds of the present application can also be used for preventing or treating of a disease associated with orphan nuclear receptor Nur77, such as cancers (e.g., triple negative breast cancer). Thus, the present invention provides a novel and potent ligand which can specifically bind to Nur77, and can be used to develop new therapies for the treatment of cancer, such as triple-negative breast cancer.

SPECIFIC MODELS FOR CARRYING OUT THE INVENTION

The invention will now be described with reference to the following examples, which are intended to illustrate, but not to limit the invention.

Unless otherwise specified, the molecular biology experimental methods and immunoassays applied in the present invention are basically performed by referring to the methods on Molecular Cloning: A Laboratory Manual, 2nd Edition, Cold Spring Harbor Laboratory Press, 1989, by J. Sambrook et al., and Short Protocols in Molecular Biology, 3rd Edition, John Wiley & Sons, Inc., 1995, by F. M. Ausubel et al.; restriction enzymes are used in accordance with the conditions recommended by the product manufacturer. Any reagents or instruments that are not indicated by the manufacturer are commercially available products.

DRAWINGS

FIG. 1 showed the screening of compounds capable of binding to Nur77 using Biacore T200. The results of the binding of YXY101 to Nur77-LBD detected by Biacore T200 were shown, wherein red dots represented compound YXY101; blue dots represented control compounds. The results showed that compound YXY101 was able to bind to Nur77-LBD.

Figure 2:
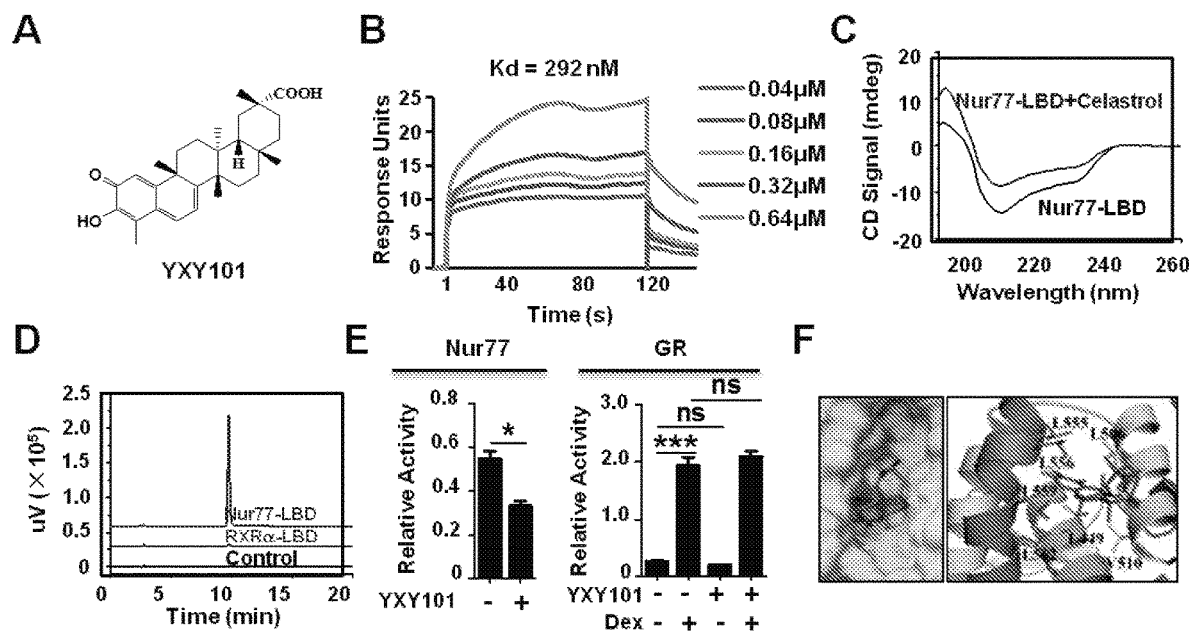

FIG. 2A showed the chemical structure of Celastrol (compound YXY101).

FIG. 2B showed the results of further experiment on the binding of different concentrations of YXY101 (0.04 µM, 0.08 µM, 0.16 µM, 0.32 µM, 0.64 µM) to Nur77-LBD. The results showed that the dissociation constant (Kd) of compound YXY101 to Nur77-LBD was 292 nM;

FIG. 2C showed the results of experiment on the binding of YXY101 to Nur77-LBD detected by circular dichroism spectroscopy, wherein the red curve represents YXY101+Nur77-LBD; the blue curve represents Nur77-LBD. The results showed that compound YXY101 was able to change the CD spectrum of Nur77-LBD. It indicated that compound YXY101 was able to bind to Nur77-LBD.

FIG. 2D showed the results of experiment on the binding of YXY101 to Nur77-LBD detected by HPLC, wherein the red curve represented YXY101+Nur77-LBD; the purple curve represented YXY101+RXRα-LBD. The results showed that compound YXY101 was able to bind to Nur77-LBD to form a complex, but not to RXRα-LBD.

FIG. 2E showed the results of experiment on the binding of YXY101 to Nur77-LBD detected by dual-luciferase reporter assay system. The results showed that compound YXY101 was able to inhibit the transactivation function of Nur77, but had no significant effect on transactivationthat of glucocorticoid receptor (GR). It indicated that compound YXY101 was capable of binding to Nur77-LBD and inhibiting the transcriptional activity of Nur77-LBD; whereas compound YXY101 does not bind to GR.

FIG. 2F showed the molecular docking of YXY101 to Nur77. The results showed that YXY101 binded to known hydrophobic grooves on the surface of Nur77 protein mainly by hydrophobic interaction.

Figure 3:
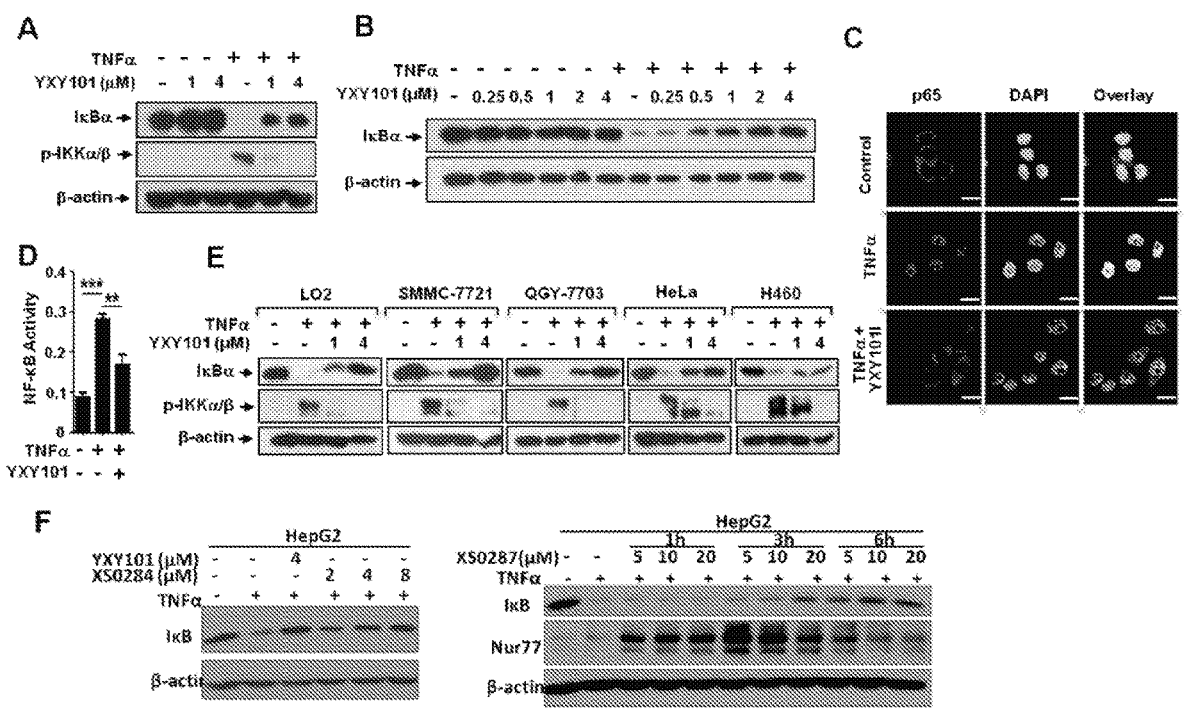

FIGS. 3A-3B showed the results of immunoblotting analysis of IκBα and phosphorylated IKKα/β in cells treated with different concentrations of YXY101 and TNFα.

FIG. 3C showed the immunofluorescence staining results of cells treated with YXY101 and TNFα (Scale bar: 20 µm).

FIG. 3D showed the analysis results of NF-κB activity of cells treated with YXY101 and TNFα, wherein P<0.01, *P<0.001 (T test).

FIG. 3E showed the results of immunoblot analysis of IκBα and phosphorylated IKKα/β in different cancer cell lines treated with different concentrations of YXY101 and TNFα.

FIG. 3F showed the results of immunoblot analysis of IκBα in HepG2 cells stimulated with TNFα and treated with different compounds.

Figure 4:
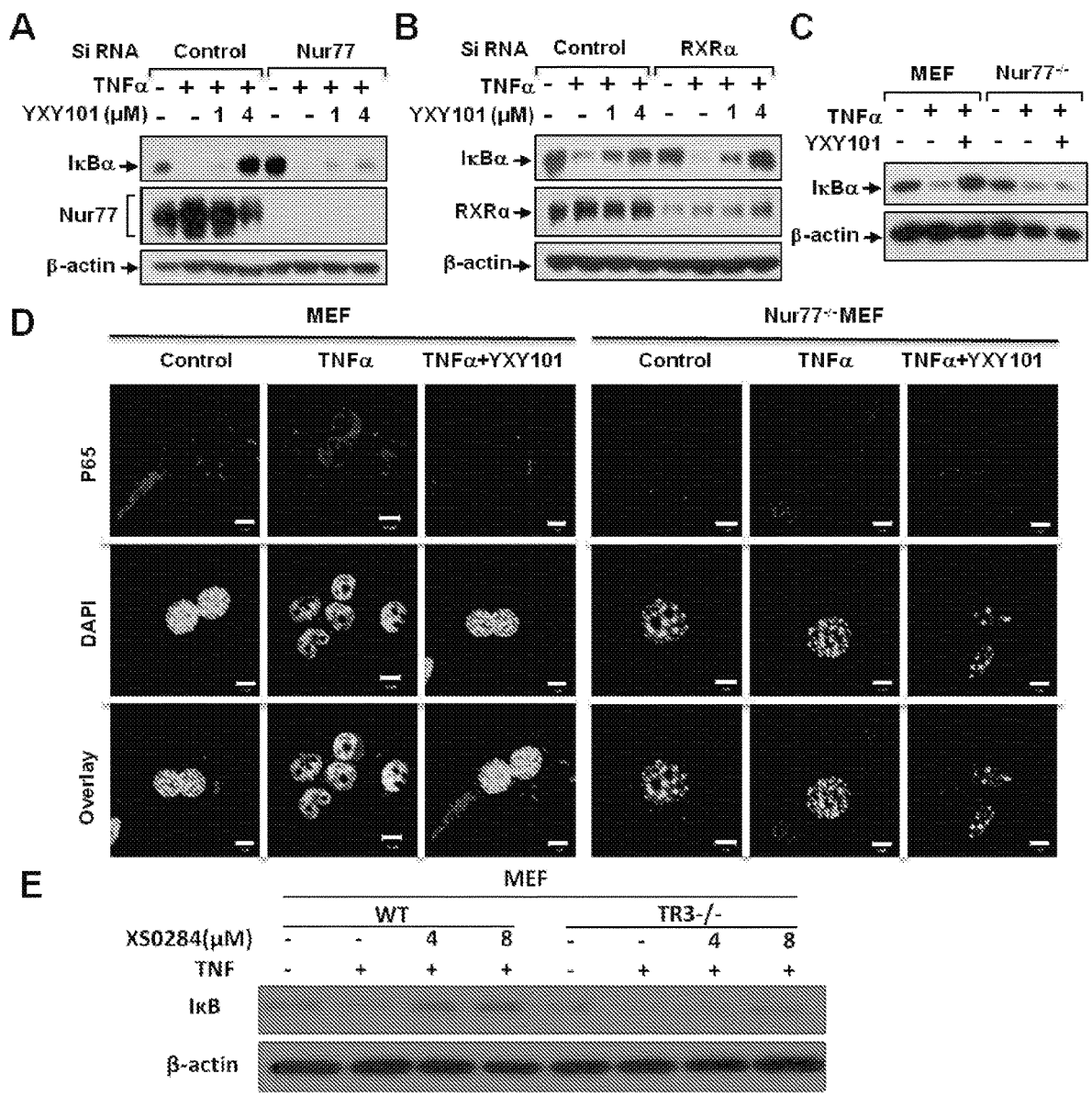

FIGS. 4A-4B showed the results of immunoblot analysis of Nur77, RXRα and IκBα in HepG2 cells transfected with different siRNAs and treated with different concentrations of YXY101 and TNFα.

FIG. 4C showed the results of immunoblot analysis of IκBα in MEF cells and Nur77−/−MEF cells treated with different concentrations of YXY101 and TNFα.

FIG. 4D showed the immunofluorescence staining results of MEF cells and Nur77−/−MEF cells treated with YXY101 and TNFα (Scale bar: 10 µm).

FIG. 4E showed the results of immunoblot analysis of IκBα in MEF cells and Nur77−/−MEF cells treated with different concentrations of XS0284 and TNFα.

Figure 5:
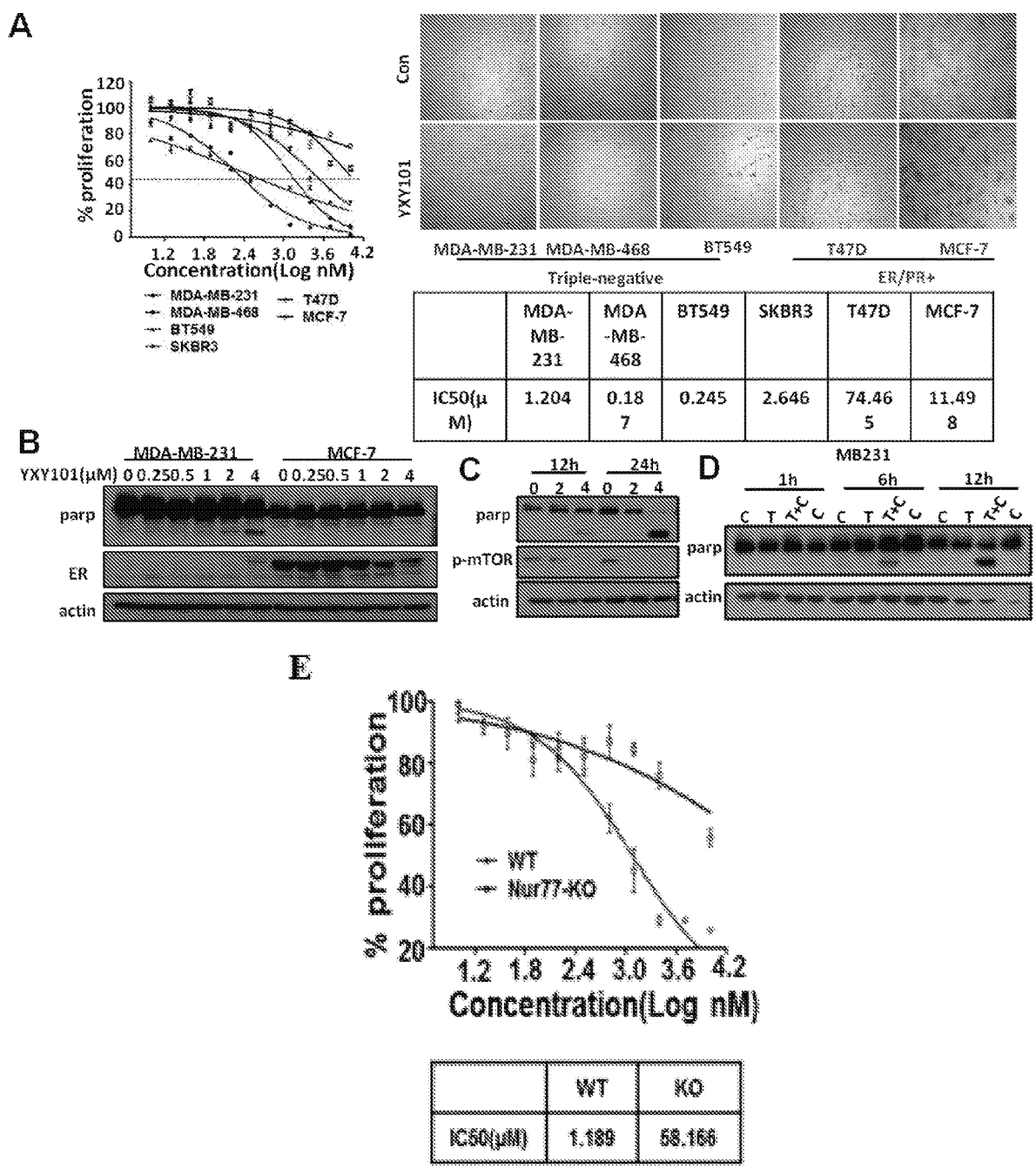

FIG. 5A showed the proliferation ratio of different breast cancer cells (MDA-MB-231; MDA-MB-468; BT549; SKBR3; T47D and MCF-7) in relation to YXY101 concentration, as well as the IC50 of YXY101; wherein MDA-MB-231, MDA-MB-468, BT549 and SKBR3 are triple negative breast cancer cells, indicated by red curves; T47D and MCF-7 are triple positive breast cancer cells, indicated by blue curves.

FIG. 5B showed the results of immunoblot analysis of parp and ER in MDA-MB-231 and MCF-7 cells treated with different concentrations of YXY101 (0 µM, 0.25 µM, 0.5 µM, 1 µM, 2 µM, or 4 µM).

FIG. 5C showed the results of immunoblot analysis of parp and p-mTOR in MDA-MB-231 treated with different concentrations of YXY101 (0 µM, 2 µM, or 4 µM) for 12 h or 24 h.

FIG. 5D showed the results of immunoblot analysis of parp in MDA-MB-231 cells treated with YXY101 in combination with TNFα for different time period (1 h, 6 h or 12 h).

FIG. 5E showed the curves of proliferation ratios of Hela cells in relation to concentrations of YXY101, and the results showed that the IC50 of YXY101 for wild-type Hela cells was 1.189 µM, while the IC50 for Nur77 knock-out Hela cells was 58.166 µM.

FIGS. 6A-B showed results from testing the anti-tumor effect of YXY101 alone or in combination with TNFa on triple-negative breast cancers via nude mice xenograft experiments. In FIG. 6A, the left panel showed the tumors formed in nude mice from each group; the middle panel showed the RTV values of the tumors formed in nude mice from each group; the right panel showed the weight values of the tumors formed in nude mice from each group. FIG. 6B showed the immunohistochemical staining results of tumor tissues of nude mice from each group.

FIG. 7A showed the general state of MMTV-PYVT mice at 2 weeks, 11 weeks, 13 weeks or 17 weeks after intragastric administration of 2 mg/kg of YXY101.

FIG. 7B showed the results of HE staining and immunohistochemical staining of tumor tissues of MMTV-PYVT mice at 2 weeks, 11 weeks, 13 weeks or 17 weeks after intragastric administration of 2 mg/kg of YXY101.

FIG. 7C showed the analysis results of weight, morphology, HE staining and immunohistochemical staining of lung tissues of MMTV-PYVT mice at 2 weeks, 11 weeks, 13 weeks or 17 weeks after intragastric administration of 2 mg/kg of YXY101.

FIG. 8A showed the survival curves within 60 days of wild-type mmtv-PyMT mice, and Nur77-knocked-out mmtv-PyMT mice.

FIG. 8B showed the statistical results of tumor weight comparison at 11 weeks, 13 weeks, and 17 weeks in wild type mmtv-PyMT mice, Nur77 knockout mmtv-PyMT mice.

FIG. 8C showed the comparison results of tumor in appearance and morphological size at 11 weeks, 13 weeks, and 17 weeks in wild type mmtv-PyMT mice and Nur77-knocked-out mmtv-PyMT mice.

FIG. 8D showed the effect of YXY101 on the survival rate of mmtv-PyMT mice detected at the animal level.

Figure 9:
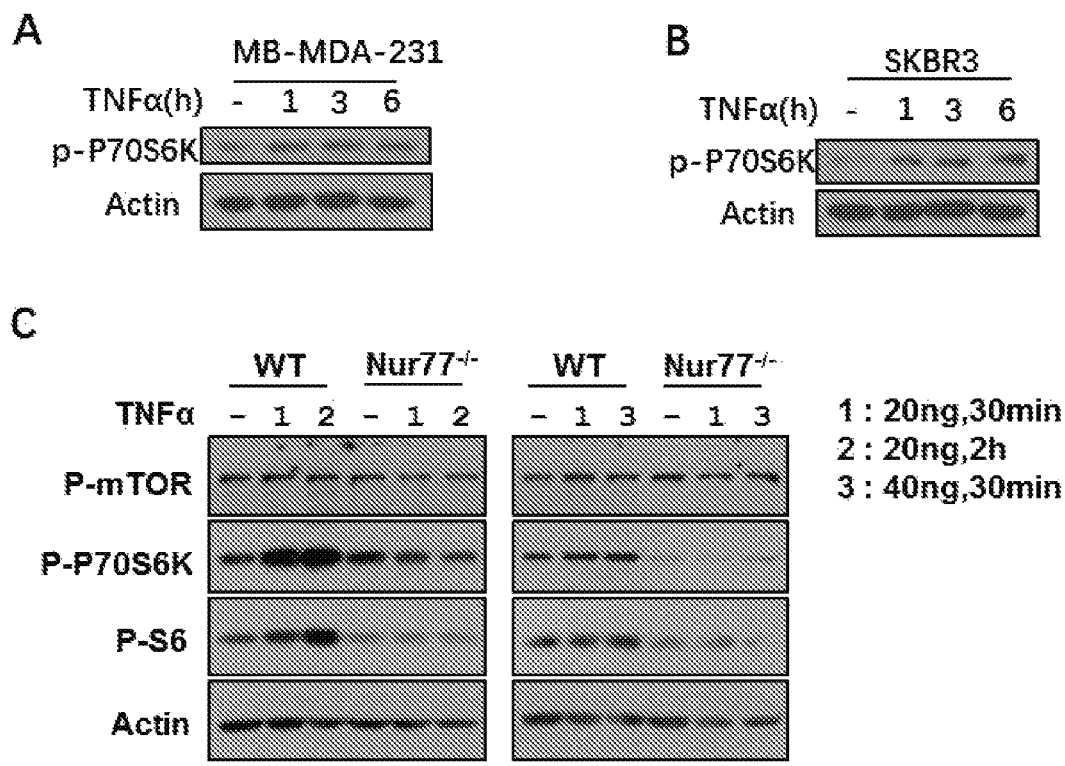

FIG. 9A showed the results of p-P70S6K levels in MB-MDA-231 breast cancer cells treated with TNFα under starvation condition, detected by immunoblotting technology.

FIG. 9B showed the results of p-P70S6K levels in SKBR3 breast cancer cells treated with TNFα under starvation condition, detected by immunoblotting technology.

FIG. 9C showed the results of levels of p-mTOR, p-P70S6K, p-S6 in wild-type and Nur77-knocked-out MEF cells treated with TNFα for different periods of time (30 min, 2 h) or at different concentrations (20 ng/ml/, 40 ng/ml) under starvation conditions, detected by immunoblotting technology.

Figure 10:
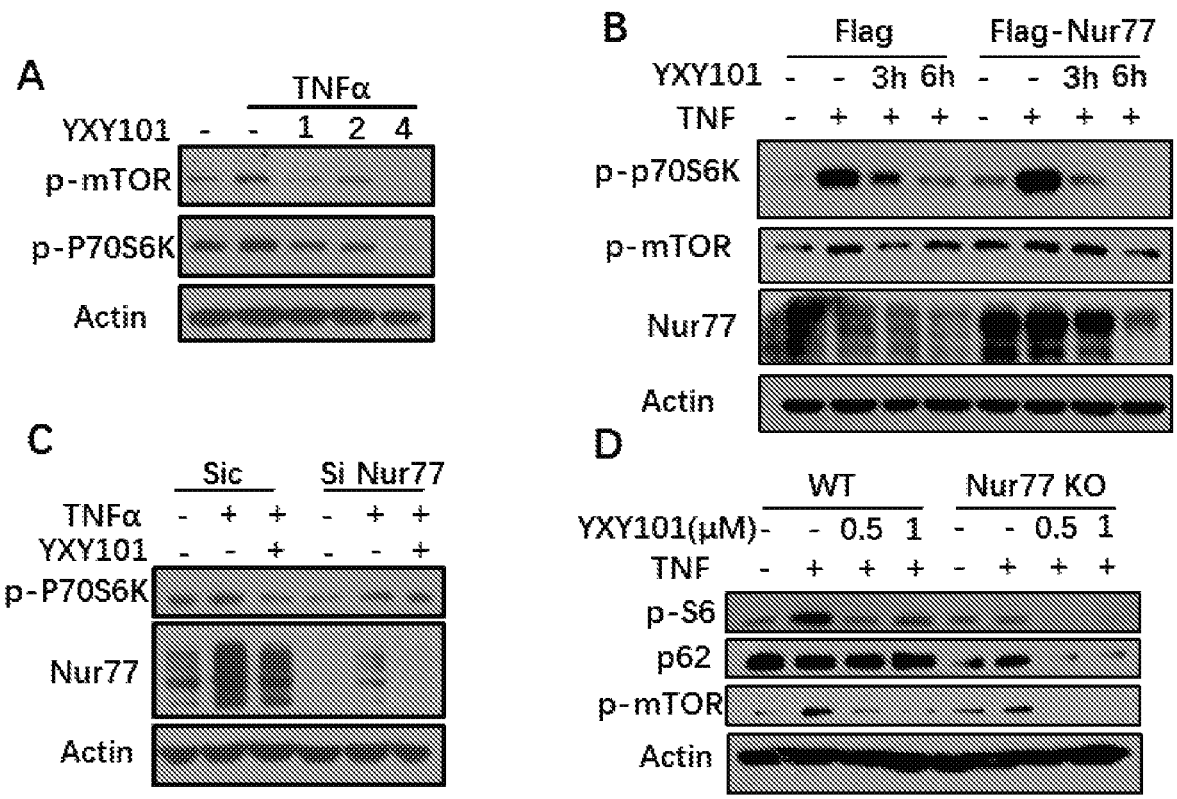

FIG. 10A showed the results of levels of p-mTOR, p-P70S6K in MB-MDA-231 breast cancer cells treated with TNFα (20 ng/ml), YXY101 (1 µM, 2 µM, 4 µM) under starvation condition, detected by immunoblotting technology.

FIG. 10B showed the results of levels of p-mTOR, p-P70S6K, Nur77 in MB-MDA-231 breast cancer cells, which were transfected with Flag empty plasmid or Flag-Nur77 plasmid and treated with TNFα, YXY101 for 3 h, 6 h under starvation condition, detected by immunoblotting technology.

FIG. 10C showed the results of levels of p-P70S6K and Nur77 in MB-MDA-231 cells which were treated to silence Nur77 gene, and then with TNFα, YXY101 under starvation condition, detected by immunoblotting technology.

FIG. 10D showed the results of levels of p-S6, p-mTOR, and p62 in wild-type or Nur77-knocked-out type MEF cells treated with TNFα, YXY101 (0.5 Mm, 1 µM), detected by immunoblotting technology.

Figure 11:
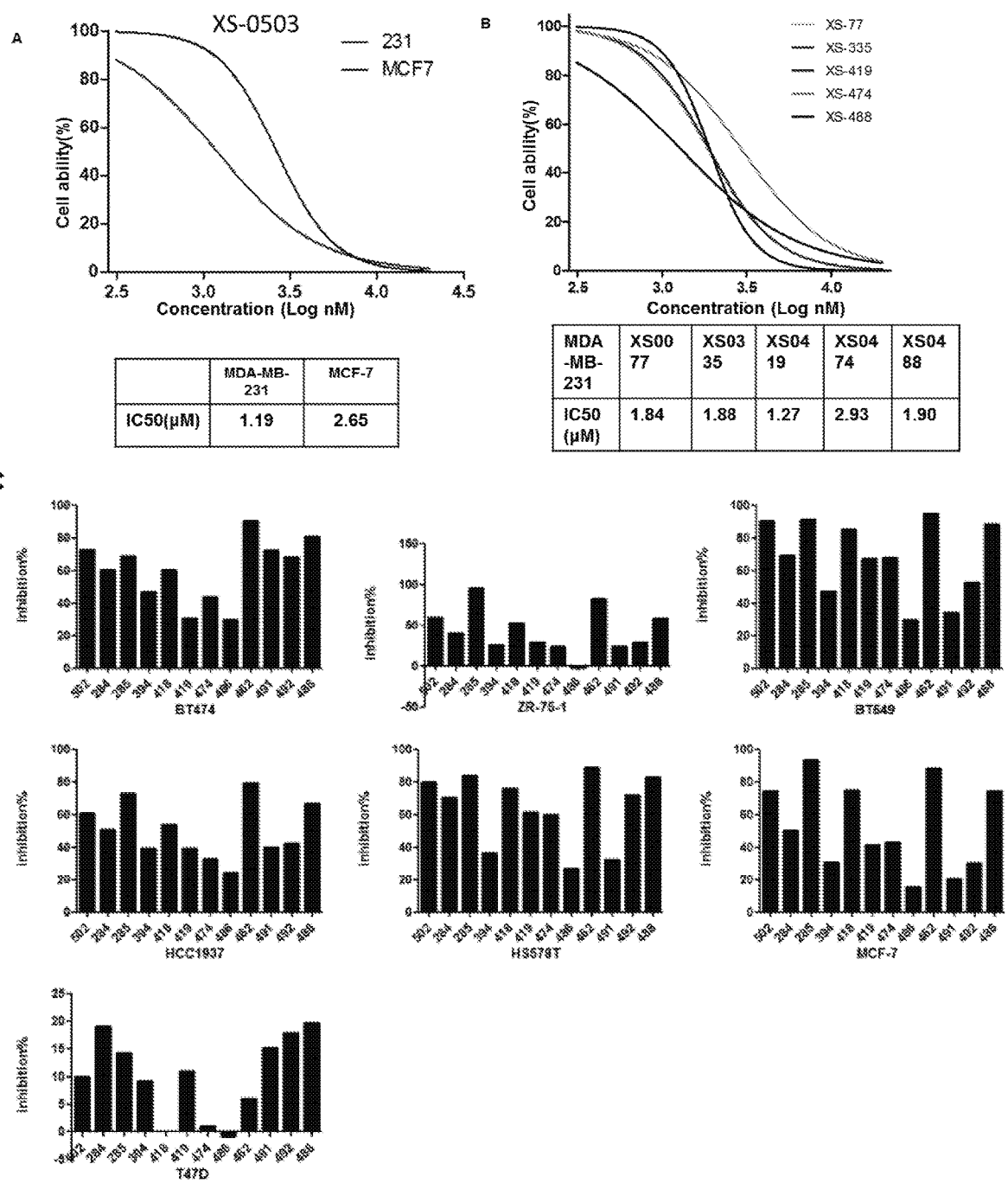

FIG. 11A showed the proliferation ratios of different breast cancer cells (MDA-MB-231 and MCF-7) in relation to concentration of XS0503, as well as the IC50 value of XS0503.

FIG. 11B showed the IC50 analysis results of MDA-MB-231 cells treated with YXY101 derivatives XS0077, XS0335, XS0419, XS0474, or XS0488.

FIG. 11C showed the analysis results of inhibition rate to seven breast cancer cells, BT474, ZR-75-1, BT549, HCC1937, HS578T, MCF-7, and T47D, treated with YXY101 derivatives, XS0284, XS0285, XS0394, XS0418, XS0419, XS0474, XS0486, XS0462, XS0491, XS0492, or XS0488.

Figure 12:
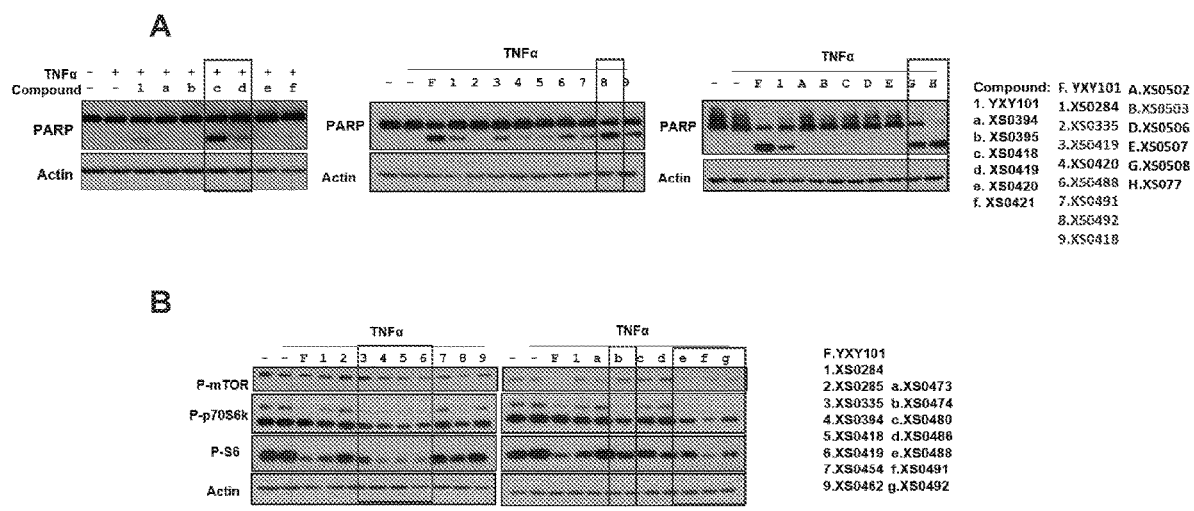

FIG. 12A showed the immunoblotting analysis results of PARP in MDA-MB-231 cells treated with YXY101 (4 µM) or different YXY101 derivatives (4 µM), XS0394, XS0395, XS0419, XS0420, XS0421, XS0284, XS0335, XS0488, XS0491, XS0492, XS0418, XS0502, XS0503, XS0506, XS0507, XS0508, XS0077, as well as TNFα (20 ng/ml).

FIG. 12B showed the immunoblotting analysis results of P-mTOR, P-p70S6K, and P—S6 in MDA-MB-231 cells under starvation treatment with serum-free medium for 10 h, and treated with YXY101 (2 µM) or different YXY101 derivatives (2 µM), XS0284, XS0285, XS0335, XS0394, XS0418, XS0419, XS0454, XS0462, XS0473, XS0474, XS0480, XS0486, XS0488, XS0491, or XS0492, as well as TNFα (20 ng/ml).

Figure 13:
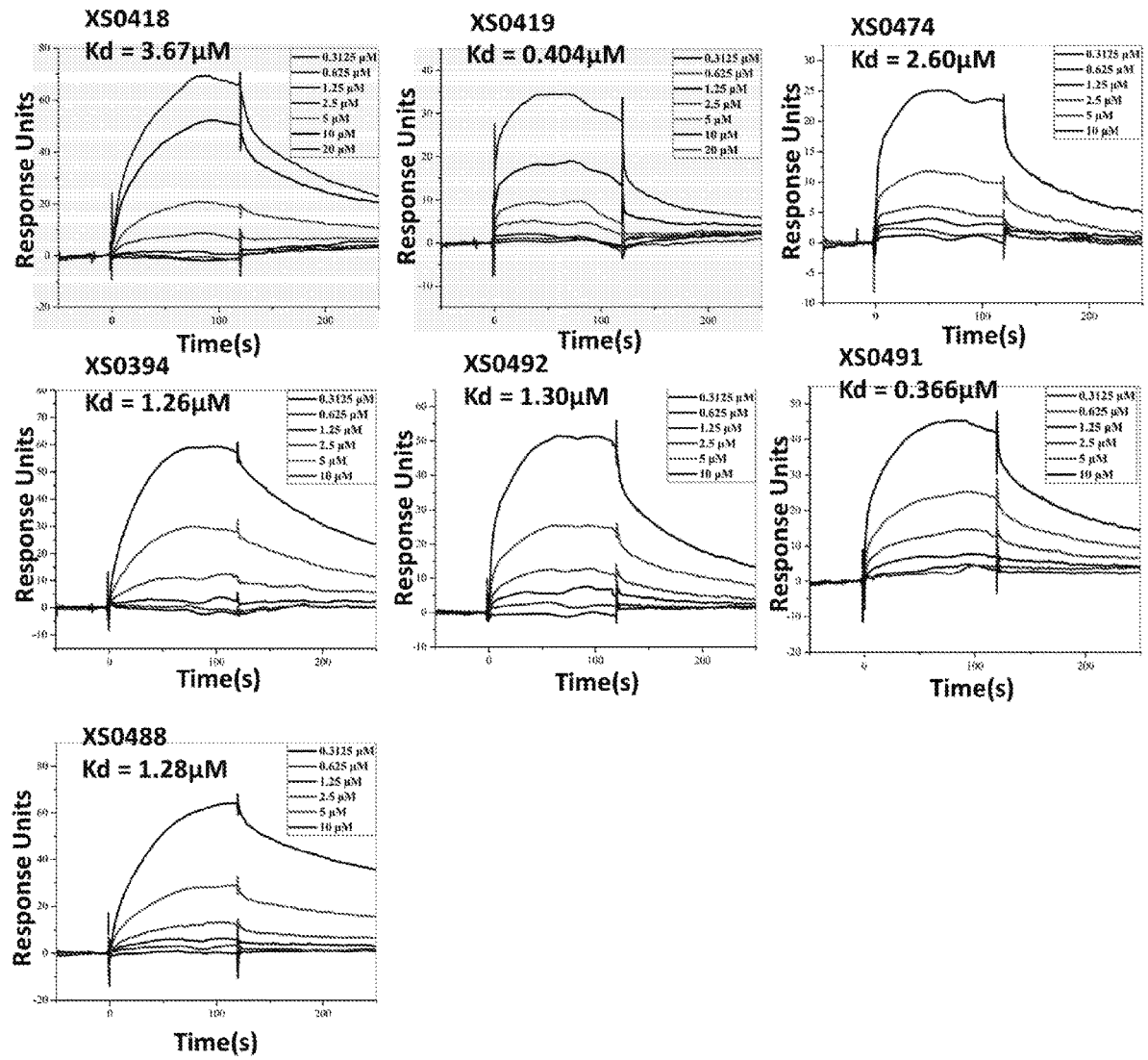

FIG. 13 showed the experimental results for detecting the binding of different compounds (XS0418, XS0419, XS0474, XS0394, XS0492, XS0491, XS0488) to Nur77-LBD by using Biacore T200. The results showed that the dissociation constant (Kd) of the compound XS0418 to Nur77-LBD is 3.67 µM; the dissociation constant (Kd) of the compound XS0419 to Nur77-LBD is 404 nM; the dissociation constant (Kd) of the compound XS0474 to Nur77-LBD is 2.60 µM; the dissociation constant (Kd) of the compound XS0394 to Nur77-LBD is 1.26 µM; the dissociation constant (Kd) of the compound XS0492 to Nur77-LBD is 1.30 µM; the dissociation constant (Kd) of the compound XS0491 to Nur77-LBD is 0.336 µM; the dissociation constant (Kd) of the compound XS0488 to Nur77-LBD is 1.28 µM.

Figure 14:
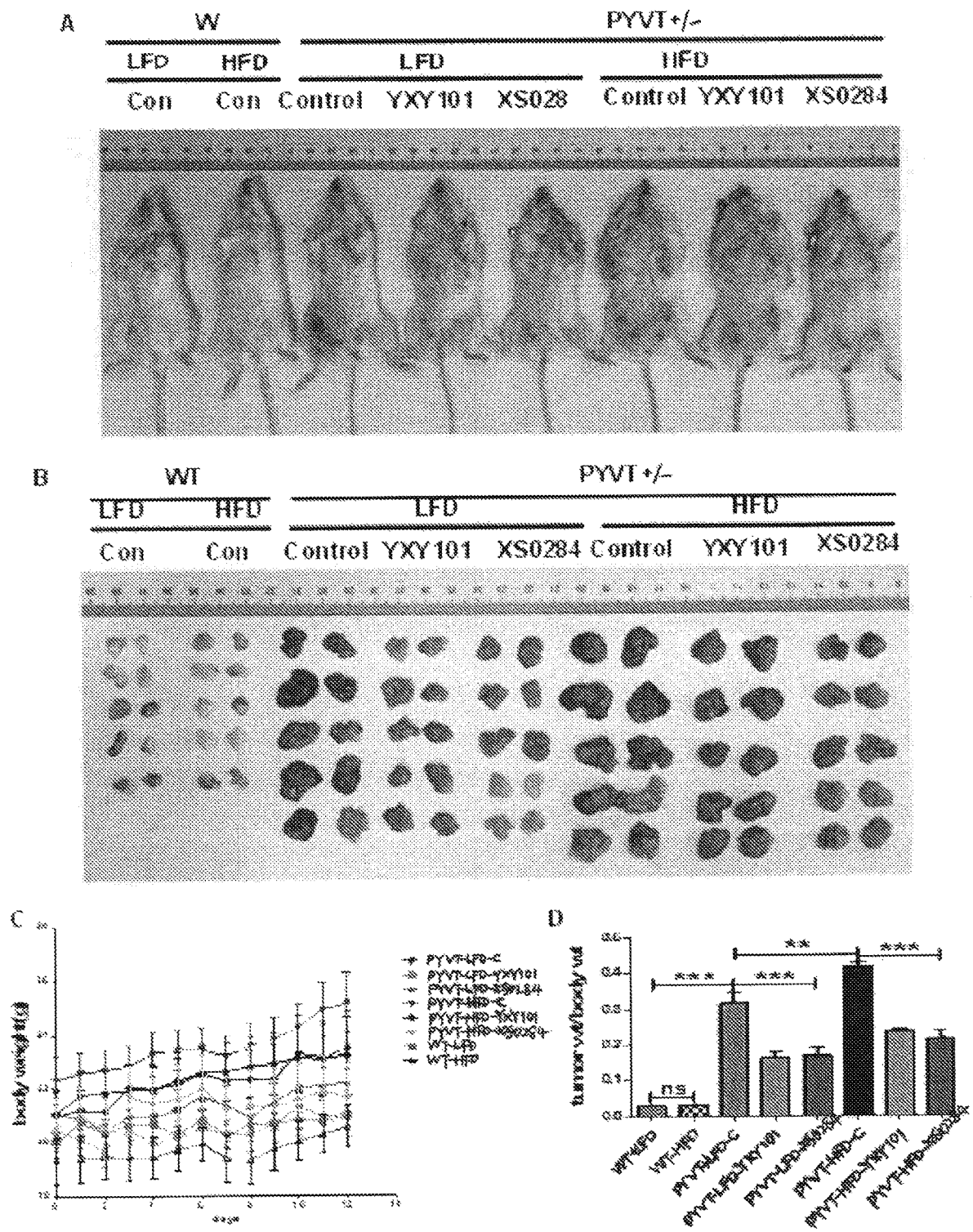

FIG. 14 showed the results of experiment on WT mice and PYVT mice, which were respectively treated with LFD feeding and HFD feeding and intragastric administrated with two compounds, YXY101 and its derivative XS0284. FIG. 14A showed the morphology and appearance of the mice in different experimental groups under different treatment conditions. FIG. 14B showed the comparison of the morphology and size of the tumors of the above mice. FIG. 14C showed the curves of change in body weight of the above mice during the 12-day period of intragastric administration. FIG. 14D showed the statistical significance of the change in body weight of the above mice before and after treatment.

Figure 15:
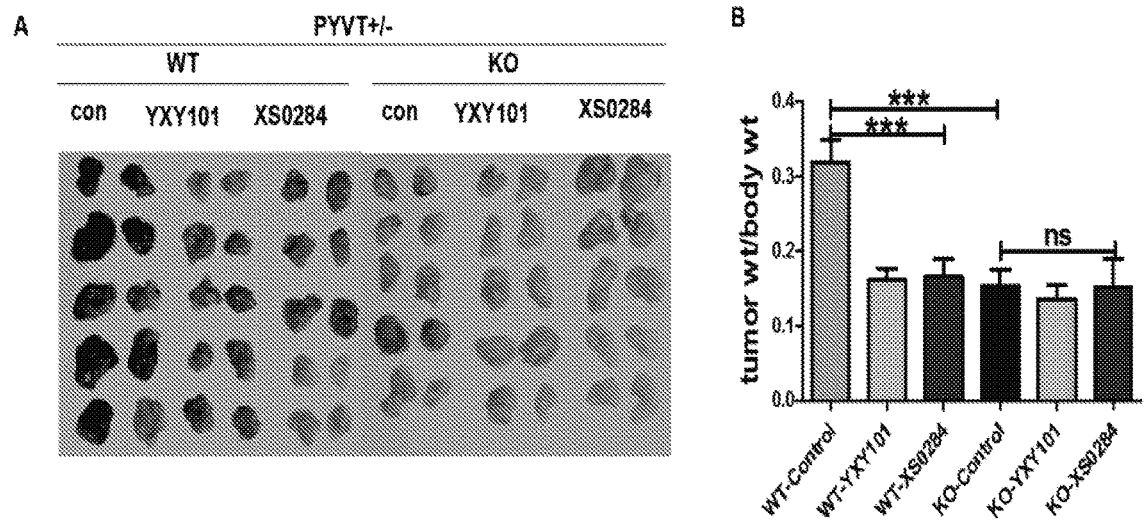

FIG. 15A showed a comparison of morphology and size of tumors after treating with YXY101 or its derivative XS0284 in WT and Nur77-knocked-out mice of PYVT.

FIG. 15B showed the statistical results of tumor tissue weight in the above mice.

Figure 16:
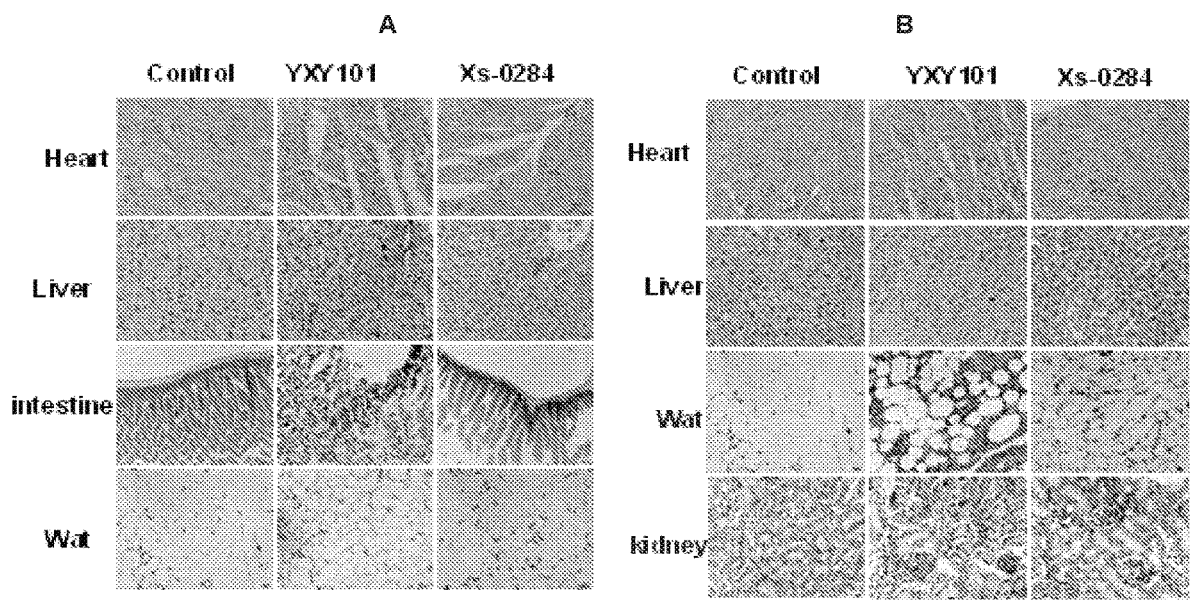

FIG. 16 showed the results of tissue morphology and HE staining of the heart, liver, small intestine, white fat and kidney of mice of each group, which were observed after 12 hours of intragastric administration or intraperitoneal injection of YXY101 or XS0284 (200 mg/kg) in acute toxicity model mice induced by single intragastric administration or intraperitoneal injection of 200 mg/kg of YXY101 or its derivative XS0284.

EXAMPLE 1. CHARACTERIZATION OF COMPOUND YXY101

(1) Surface Plasmon Resonance (SPR)

The binding of YXY101 to Nur77 was tested by surface plasmon resonance. Briefly, 50 µg purified ligand binding domain of Nur77 (Nur77-LBD) protein was coupled to CM5 of Biacore; the binding of YXY101 (20 µm) to Nur77-LBD was subsequently tested by Biacore T200. Unrelated compounds were used as controls. The test results were shown in FIG. 1.

FIG. 1 showed the test results of the binding of YXY101 to Nur77-LBD by Biacore T200, wherein red dots represented the compound YXY101; blue dots represented control compounds. The results showed that the compound YXY101 was able to bind to Nur77-LBD.

(2) Binding Kinetics of YXY101 to Nur77

The dissociation constant (Kd) of YXY101 to Nur77 was tested by surface plasmon resonance. Briefly, Biacore T200 instrument was used to measure the binding of YXY101 in different concentrations (0.04 μM, 0.08 μM, 0.16 μM, 0.32 μM, 0.64 μM) to Nur77-LBD. The test results were shown in FIG. 2B.

The results showed that the dissociation constant (Kd) of the compound YXY101 to Nur77-LBD was 292 nM.

(3) Circular Dichroism Spectroscopy (CD)

The binding of YXY101 to Nur77-LBD was further analyzed by circular dichroism spectroscopy (CD). Briefly, YXY101 (1 ml, 1 mg/ml) was added to the phosphate buffer (10 μm, pH 7.4) of Nur77-LBD protein (1 ml, 1 mg/ml) and incubated at 4° C. for 3 h. 0.7 ml of the incubation buffer was detected with Jasco J-810 spectropolarimeter. The CD spectra was obtained from 190 nm to 260 nm. Nur77-LBD solution (i.e., no YXY101 was added) alone was used as control. The results of the detection were shown in FIG. 2C.

The results showed that the compound YXY101 was able to change the CD spectrum of Nur77-LBD, indicating that the compound YXY101 was able to bind to Nur77-LBD.

(4) High Performance Liquid Chromatography (HPLC) Analysis

The binding of YXY101 to Nur77-LBD was further analyzed by high performance liquid chromatography (HPLC). Briefly, YXY101 (600 uL, 0.1 mg/ml) was incubated with purified Nur77-LBD protein (5 ml, 1 mg/ml). After incubation for 3 h at 4° C., the complex of YXY101 and Nur77-LBD was captured using Ni beads. The complex was then degenerated with chloroform, and YXY101 in the degenerated product was extracted. Then, HPLC spectrometer (Shimadzu L C 20A, Japan) was used to detect YXY101 in the extracted product, wherein ODS column (5 um, 4.6*250 mm) was used, and the mobile phase was 0.2% $H_3PO_4$ acetonitrile. The detection wavelength was 425 nm. In addition, the above experiment was repeated using YXY101 and RXRα-LBD (ligand binding domain of retinoic X receptor α) as control. The results of the detection were shown in FIG. 2D.

The results showed that the compound YXY101 was able to bind to Nur77-LBD to form a complex, but not to RXRα-LBD.

(5) Dual Luciferase Reporter Assay

The binding of YXY101 to Nur77-LBD was further analyzed by dual luciferase reporter assay. In addition, the experiment was repeated using YXY101 and glucocorticoid receptor (GR) as control. The results were shown in FIG. 2E.

The results showed that the compound YXY101 was able to inhibit the transactivation of Nur77, but had no significant effect on the transactivation of glucocorticoid receptor (GR). This indicated that the compound YXY101 was capable of binding to Nur77-LBD and inhibiting its transcriptional activity; but not to GR.

(6) Molecular Simulation

The docking of YXY101 to Nur77 (PDB code: 4JGV) was performed using AutoDock V4.2. The conformation of YXY101 was generated by the Lamarckian genetic algorithm. In the crystal structure of Nur77, grid center was chosen aroud the reported coordinates (−12.08, 18.29, −4.233) of THPN, and the grid size was set to 40*40*40 (X, Y, Z) grid points with a spacing of 0.375 A between grid points.

In the molecular docking, the standard docking protocol was applied: the number of randomly placed individuals was 150; the maximum number of energy evaluation was 2.5 million; the rate of gene mutations was 0.02; the rate of crossover was 0.8; the probability of performing local evaluation was 0.06; the lower bound on rho was 0.01; PyMOL Version 0.99 was used for molecular visualization. The results were shown in FIG. 2F.

The molecular docking studies showed that YXY101 binded to the known hydrophobic grooves on the surface of Nur77 protein mainly by hydrophobic interaction.

EXAMPLE 2. YXY101 INHIBITS THE BIOLOGICAL EFFECT OF TNFα

HepG2 cells were treated with different concentrations of YXY101 (0 μM, 0.25 μM, 0.5 μM, 1 μM, 2 μM or 4 μM) for 1 hour, and then exposed to TNFα (0 ng/mL or 20 ng/mL) for 30 minutes. IκBα and phosphorylated IKKα/β in the cells were then detected by WB. The results were shown in FIGS. 3A-3B.

The results of FIGS. 3A-3B showed that TNFα was capable of inducing phosphorylation of IKKα/β and degradation of IκBα in cells; whereas YXY101 was capable of inhibiting TNFα-induced phosphorylation of IKKα/β and degradation of IκBα.

HepG2 cells were treated with YXY101 (0 or 1 μM) for 1 hour, and then exposed to TNFα (20 ng/mL) for 30 minutes. The p65 subunit of NF-κB in the cells was then detected by immunofluorescence staining method. Untreated cells were used as controls. The results were shown in FIG. 3C.

FIG. 3C showed the immunofluorescence staining results of HepG2 cells treated with YXY101 and TNFα (Scale bar: 20 μm). The results in FIG. 3C showed that TNFα was able to induce nuclear import of the p65 subunit of NF-κB in cells; whereas YXY101 was able to inhibit TNFα-induced p65 nuclear import.

The NF-κB reporter gene was transfected into HEK-293T cells and then treated with YXY101 (0 or 1 μM) and TNFα (20 ng/mL). NF-κB activity in the cells was then analyzed. Untreated cells were used as controls. The results were shown in FIG. 3D.

FIG. 3D showed the analytic results of NF-κB activity of cells treated with YXY101 and TNFα, wherein $P<0.01$, *$P<0.001$ (T test). The results in FIG. 4D showed that TNFα was able to induce transactivation of NF-κB in cells; whereas YXY101 was able to inhibit TNFα-induced NF-κB transactivation.

A variety of cancer cell lines (LO2, SMMC-7721, QGY-7703, HeLa, H460) were treated with different concentrations of YXY101 (0 μM, 1 μM or 4 μM) for 1 hour, and then exposed to TNFα (0 ng/mL or 20 ng/mL) for 30 minutes. IκBα and phosphorylated IKKα/β in the cells were then detected by WB. The results were shown in FIG. 3E.

The results showed that TNFα was able to induce phosphorylation of IKKα/β and degradation of IκBα in various cell lines, whereas YXY101 was able to inhibit TNFα-induced phosphorylation of IKKα/β and degradation of IκBα.

In addition, HepG2 cells were also applied in the experiment. Briefly, HepG2 cells were treated with various compounds (YXY101, XS0284, and XS0287) in specified concentrations for a specified period of time, and then exposed to TNFα (0 ng/mL or 20 ng/mL) for 30 minutes. IκBα in the cells was then detected by WB. The results were shown in FIG. 3F.

FIG. 3F showed that YXY101 and its derivatives XS0284 and XS0287 were capable of inhibiting TNFα-induced degradation of IκBα in HepG2 cells.

The results of FIGS. 3A-3F indicated that YXY101 and its derivatives XS0284 and XS0287 were capable of inhibiting various biological effects of TNFα in cells, including phosphorylation of IKKα/β, degradation of IκBα, nuclear import of the p65 subunit of NF-κB, and transactivation of NF-κB.

EXAMPLE 3. Nur77 MEDIATES THE INHIBITORY EFFECT OF YXY101 ON BIOLOGICAL EFFECTS OF TNFα

SiRNA, Nur77 SiRNA or RXRα SiRNA as controls were transfected into HepG2 cells. Subsequently, the HepG2 cells were treated with different concentrations of YXY101 (0 μM, 1 μM or 4 μM) for 1 hour, and then exposed to TNFα (0 ng/mL or 20 ng/mL) for 30 minutes. Nur77, RXRα and IκBα in the cells were then detected by WB. The results were shown in FIGS. 4A-4B.

FIGS. 4A-4B showed the results of immunoblot analysis of Nur77, RXRα and IκBα in the HepG2 cells transfected with different SiRNAs and treated with different concentrations of YXY101 and TNFα. The results showed that Nur77 SiRNA effectively inhibited/knocked out the expression of Nur77 in the cells; and, RXRα SiRNA effectively inhibited/knocked out the expression of RXRα in the cells; while the control SiRNA did not affect the normal expression of Nur77 and RXRα. Further, the results of FIGS. 5A-5B showed that YXY101 was able to inhibit TNFα-induced degradation of IκBα in the cells expressing Nur77; however, when Nur77 expression was knocked out, YXY101 lost its ability to inhibit IκBα degradation. These results indicated that the inhibitory effect of YXY101 on biological effects of TNFα was mediated by Nur77.

The above results were also confirmed by using MEF cells and Nur77−/−MEF cells (i.e., MEF cells not expressing Nur77). Briefly, MEF cells and Nur77−/−MEF cells were treated with different concentrations of YXY101 (0 μM or 1 μM) for 1 hour, and then exposed to TNFα (0 ng/mL or 20 ng/mL) for 30 minutes. Subsequently, IκBα in the cells was detected by WB. The results were shown in FIG. 4C.

The results showed that YXY101 was able to inhibit TNFα-induced degradation of IκBα in the MEF cells expressing Nur77; however, in Nur77−/−MEF cells, YXY101 lost the ability to inhibit IκBα degradation. These results indicated that the inhibitory effect of YXY101 on the biological effects of TNFα was mediated by Nur77.

In addition, MEF cells and Nur77−/−MEF cells were treated with YXY101 (0 or 1 μM) for 1 hour, and then exposed to TNFα (20 ng/mL) for 30 minutes. Subsequently, the p65 subunit of NF-κB in the cells was detected by immunofluorescence staining. Untreated cells were used as controls. The results were shown in FIG. 4D.

FIG. 4D showed the results of immunofluorescence staining of the MEF cells and the Nur77−/−MEF cells treated with YXY101 and TNFα (Scale bar: 10 μm). The results showed that YXY101 was able to inhibit TNFα-induced p65 nuclear import in the MEF cells expressing Nur77; however, in the Nur77−/−MEF cells, YXY101 lost the ability to inhibit p65 nuclear import. These results indicated that the inhibitory effect of YXY101 on the biological effects of TNFα was mediated by Nur77.

FIG. 4E showed the results of immunoblot analysis of IκBα in MEF cells and Nur77−/−MEF cells treated with different concentrations of XS0284 and TNFα. The results show that XS0284 was able to inhibit TNFα-induced degradation of IκBα in the MEF cells expressing Nur77; however, in the Nur77−/−MEF cells, XS0284 lost the ability to inhibit IκBα degradation. These results indicated that the inhibitory effect of XS0284 on the biological effects of TNFα was mediated by Nur77.

EXAMPLE 4. YXY101 HAS SIGNIFICANT ANTI-TUMOR ACTIVITY, AND IS PARTICULARLY SENSITIVE TO TRIPLE-NEGATIVE BREAST CANCER, THE BIOLOGICAL FUNCTION IS DEPENDENT ON Nur77

Different breast cancer cells (MDA-MB-231; MDA-MB-468; BT549; SKBR3; T47D and MCF-7) were treated with different concentrations of YXY101 (1 μM, 1.3 μM, 1.6 μM, 1.9 μM, 2.2 μM, 2.5 μM, 2.8 μM, 3.1 μM, 3.4 μM, 3.7 μM, 4.0 μM) for 72 h, and the proliferation ratio of the breast cancer cells were determined. Curves of the cancer cell proliferation ratio in relation to the concentrations of YXY101 were plotted, and the IC50 of YXY101 was determined. The results were shown in FIG. 5A.

FIG. 5A showed the proliferation ratio of different breast cancer cells (MDA-MB-231; MDA-MB-468; BT549; SKBR3; T47D and MCF-7) in relation to the concentrations of YXY101, as well as the IC50 of YXY101; wherein MDA-MB-231, MDA-MB-468, BT549 and SKBR3 are triple negative breast cancer cells and the results thereof were indicated by red curves; T47D and MCF-7 are three positive breast cancer cells and the results thereof were indicated by blue curves. The results showed that the inhibitory ability of YXY101 for the proliferation of triple-negative breast cancer cells was significantly stronger than that for triple-positive breast cancer cells; wherein, the IC50 of YXY101 for inhibiting the proliferation of MDA-MB-231, MDA-MB-468, BT549 and SKBR3 were 1.204, 0.187, 0.245 and 2.646 μM respectively, which were far lower than that for T47D and MCF-7 (74.465 μM and 11.498 μM, respectively), suggesting that YXY101 can be used particularly advantageously for the treatment of triple negative breast cancers.

FIG. 5E showed that the IC50 of YXY101 was 1.189 μM in wild-type Hela cells, while 58.166 μM in Nur77 knocked-out Hela cells. The results indicated that the tumor inhibitory effect of YXY101 was dependent on Nur77. Moreover, FIG. 1 and FIG. 2B showed that YXY101 can specifically bind to Nur77, the anti-tumor activity of YXY101 was closely related to Nur77.

Further, MDA-MB-231 and MCF-7 cells were treated with different concentrations of YXY101 (0 μM, 0.25 μM, 0.5 μM, 1 μM, 2 μM, or 4 μM), followed by detection of parp and ER in the cells by WB. The results were shown in FIG. 5B.

FIG. 5B showed the results of immunoblot analysis of parp and ER in the MDA-MB-231 and MCF-7 cells treated with different concentrations of YXY101 (0 μM, 0.25 μM, 0.5 μM, 1 μM, 2 μM, or 4 μM). The results showed that YXY101 can induce parp cleavage, i.e., apoptosis, in the MDA-MB-231.

Further, MDA-MB-231 was treated with different concentrations of YXY101 (0 μM, 2 μM, or 4 μM) for different period of time (12 h or 24 h), followed by detection of parp and p-mTOR in the cells by WB. The results were shown in FIG. 5C.

FIG. 5C showed the results of immunoblot analysis of parp and p-mTOR in the MDA-MB-231 treated with different concentrations of YXY101 (0 μM, 2 μM, or 4 μM) for 12 h or 24 h. The results showed that YXY101 can induce apoptosis in MDA-MB-231 in a time- and concentration-dependent manner.

In addition, MDA-MB-231 cells were also treated with YXY101 in combination with TNFα for different period of time (1 h, 6 h or 12 h), followed by detection of parp in the cells by WB. The results were shown in FIG. 5D.

FIG. 5D showed the results of immunoblot analysis of parp in the MDA-MB-231 cells treated with YXY101 in combination with TNFα for different period of time (1 h, 6 h or 12 h). The results showed that, in MDA-MB-231, YXY101 in combination with TNFα can induce stronger apoptosis.

EXAMPLE 5. INHIBITORY EFFECT OF YXY101 ON THE PROLIFERATION OF BREAST CANCER TUMORS

In this section, we tested the anti-tumor effect of YXY101 alone or in combination with TNFα on triple-negative breast cancers via nude mice xenograft experiments.

1) Laboratory Animals and Reagents

MDA-MB-231 cells; BALB/c (nu/nu) nude mice, weighed 18-20 g, female, raised in SPF animal house, fodder, drinking water, animal cages, litter were all autoclaved, the litter was changed every two days, and strictly aseptic operations were performed. Under sterile conditions, the cells in the logarithmic growth phase for inoculation were collected and washed with serum-free medium, the number of viable cells was counted under inverted microscope and the survival rate >95%, the cell concentration was adjusted to $1\times10^6$/ml, and the tumor cells were re-suspended in PBS to prepare the cell suspension. Each nude mouse was inoculated on right subaxillary with 0.2 ml of the above cell suspension, and the tumor growth condition was observed regularly.

2) Grouping and Administration

The drug-administered groups: when the diameter of the transplanted tumor of nude mice reached about 0.5 cm, the nude mice without hemorrhage, necrosis and infection were selected for experiment. The nude mice were weighed, the tumor diameter of which was measured, and then grouped, 6 nude mice in each group; the mice of the experimental groups were administered with TNFα ($120\times10^4$ U/kg), YXY101 (2 mg/kg), or the combination thereof, and the mice of the control group were given the same amount of normal saline. TNFα was administered by intratumoral injection every other day; YXY101 was administered intragastrically daily. The nude mice were sacrificed 6 hours after the last administration, and the tumor weight was measured.

During the treatment, the food intake and body weight of the nude mice were not significantly reduced, the activity was normal, and no symptoms such as loose hair and diarrhea appeared. At the end of treatment, no death occurred in each group of nude mice. After the nude mice were sacrificed, the autopsy showed tumors had clear boundaries, uneven surface, tough texture, significant local expansion of blood vessels, and necrosis occurred in the central area of some tumors. No metastasis was observed in all groups of nude mice, and no obvious changes in appearance in the heart, liver, spleen, lung, kidney and other organs was observed in the treatment groups of nude mice.

3) Observation Index

Drawing of Tumor Growth Curves:

The formula for calculating the tumor volume (TV) is: $V=\frac{1}{2}\times a\times b\times c$; wherein a, b and c represent length, width and height, respectively. The tumor volume was calculated based on the measurement results, and the tumor growth curve was plotted with time as abscissa and tumor volume as ordinate.

The anti-tumor activity evaluation index was the relative tumor proliferation rate T/C (%): wherein T represents the RTV of the treatment group; C represents the RTV of the negative control group. The therapeutic effect evaluation criteria were: T/C %>40% for ineffective; T/C %≤40% and p<0.05 for effective.

Figure 6:
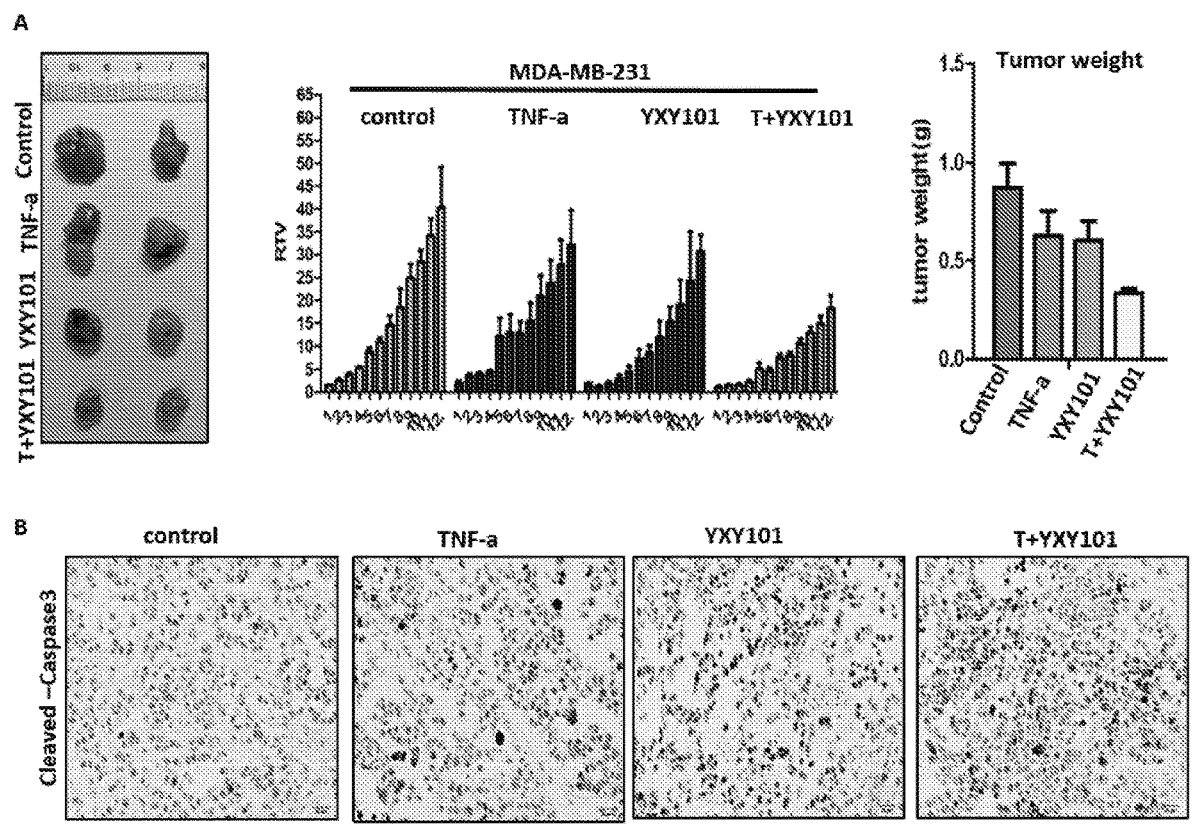

The experimental results were shown in FIG. 6. The left panel of FIG. 6A showed the tumors formed in each group of nude mice; the middle panel showed the RTV of the tumors formed in each group of nude mice; the right panel showed the weight of the tumors formed in each group of nude mice. The results of FIG. 6A showed that tumors were developed in nude mice after inoculation with MDA-MB-231 cells; and, YXY101 had good anti-tumor effect; and the combination of YXY101 and TNFα induced even stronger anti-tumor effect.

FIG. 6B showed the results of immunohistochemical staining of tumor tissues in nude mice of each group. The results of FIG. 6B show that YXY101 can induce caspase3 cleavage in tumor tissues and promote apoptosis of tumor cells; and the combination of YXY101 and TNFα can induce stronger apoptosis of tumor cells.

EXAMPLE 6. INHIBITORY EFFECT OF YXY101 ON PROLIFERATION AND METASTASIS OF BREAST CANCER

1) Laboratory Animals and Reagents

MMTV-PYVT transgenic mice of breast cancer, 9-week-old, female, were raised in SPF animal house, fodder, drinking water, animal cages, litter were all autoclaved, the litter was changed every two days, strictly aseptic operations were performed.

2) Grouping and Administration

Female MMTV-PYVT transgenic mice of breast cancer were housed under the conditions of temperature 23±1° C., humidity: 40-60%, natural light, freely drinking of water, and freely access to chow diet. Thirty-six mice with tumor began to grow in chest were selected and randomly divided into three groups, and each group was subdivided into the control group and the YXY101 group.

The administration was performed as follows:

11 Wk time point

Control group: 9-week-old mice were given normal saline at 7:00 μm every day before the fodder was given;

YXY101 group: 9-week-old mice were intragastrically administered once at a dose of 2 mg/kg at 7:00 μm every day.

13 k time point

Control group: 11-week-old mice were given normal saline at 7:00 μm every day before the fodder was given;

YXY101 group: 11-week-old mice were intragastrically administered once at a dose of 2 mg/kg at 7:00 μm every day.

17 k time point

Control group: 15-week-old mice were given normal saline at 7:00 μm every day before the fodder was given;

YXY101 group: 15-week-old mice were intragastrically administered once at a dose of 2 mg/kg at 7:00 μm every day.

After continuous administration for two weeks according to the above method, each animal was bled from the eye, and the supernatant was taken to determine the serum inflammation index; tumor tissue having clear boundary, uneven surface, and tough texture was routinely treated and embedded for immunostaining.

Figure 7:
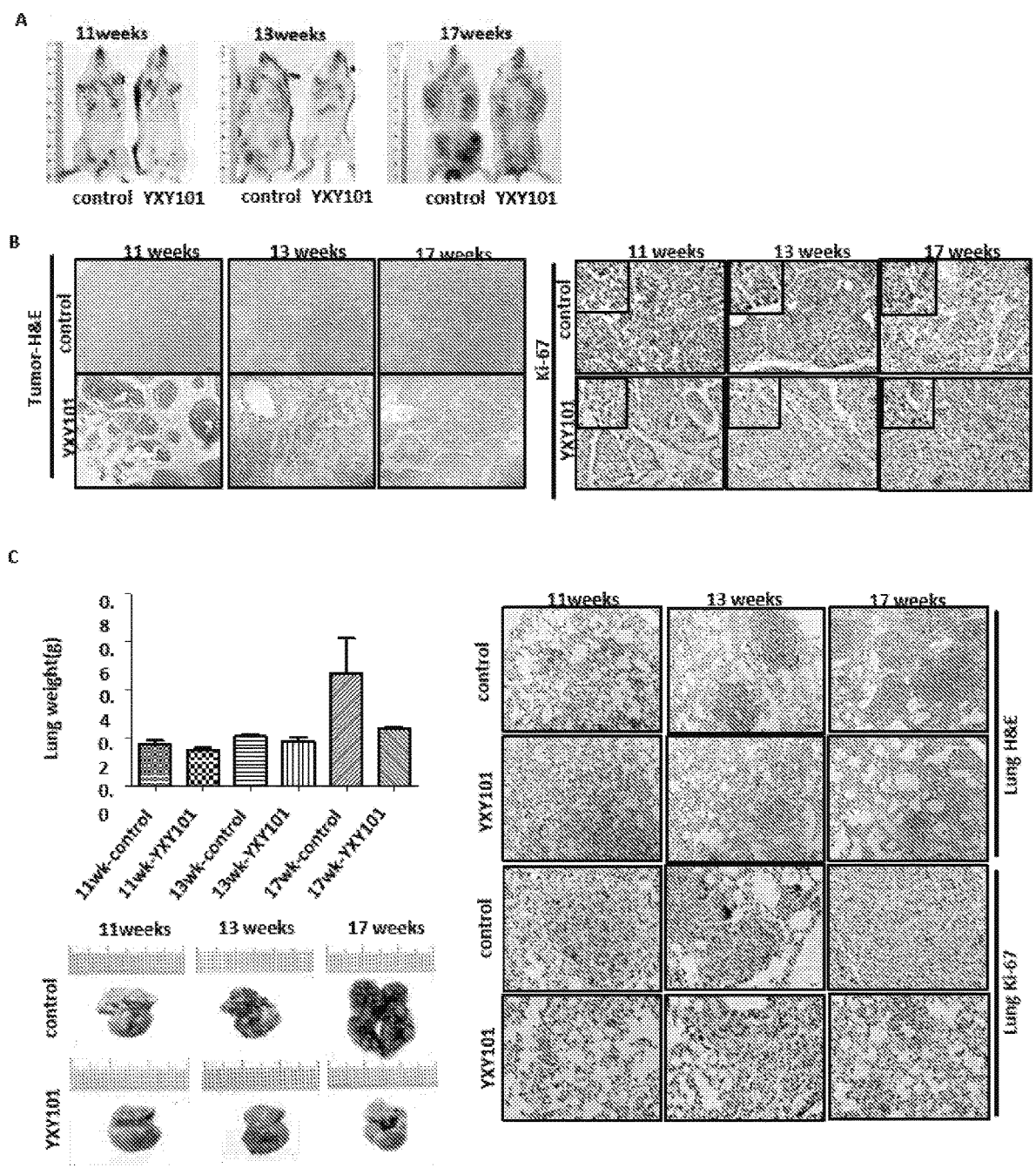
Figure 8:
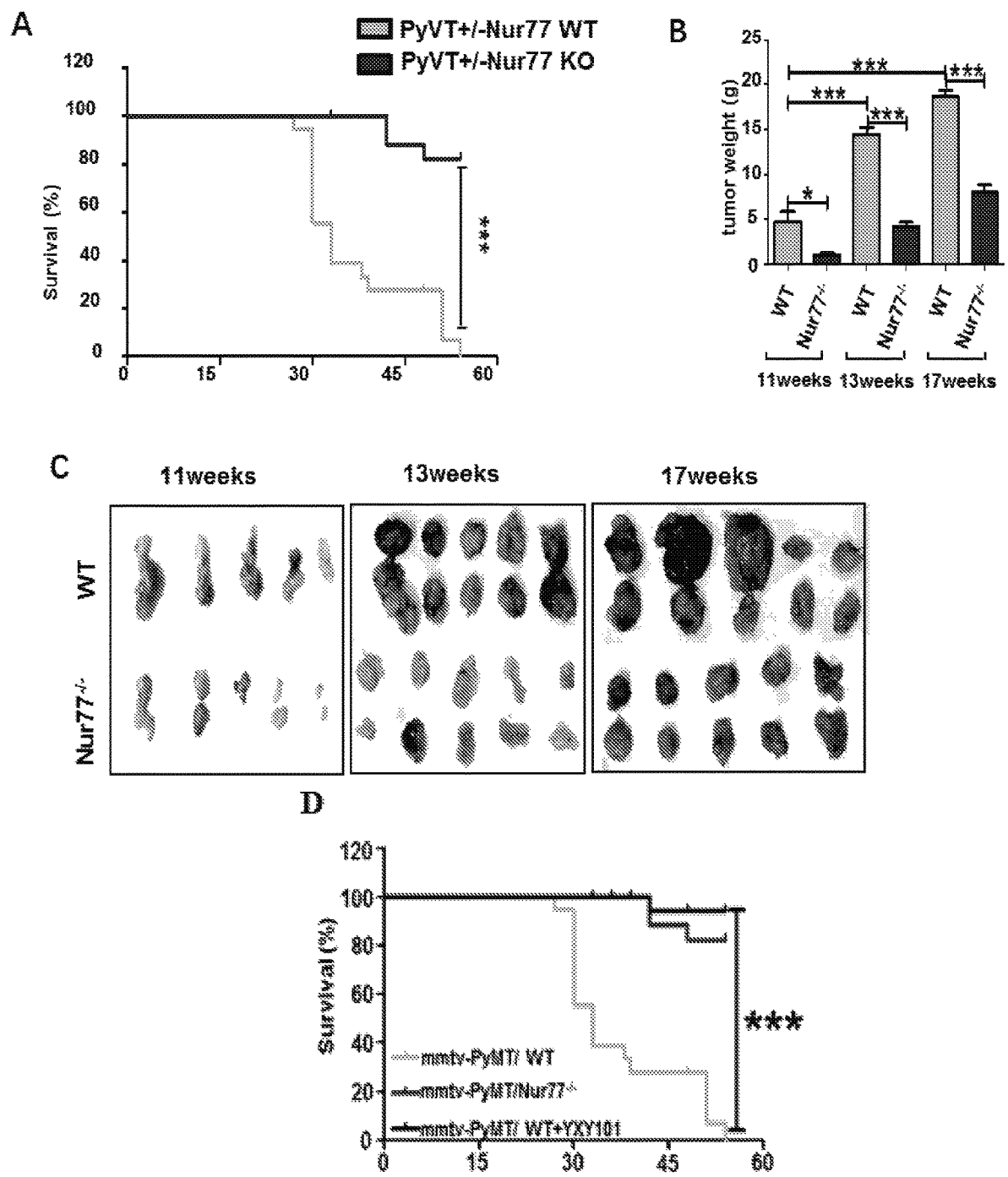

The experimental results were shown in FIG. 7 and FIG. 8. FIG. 7A showed the general state of MMTV-PYVT mice at 2 weeks, 11 weeks, 13 weeks or 17 weeks after intragastric administration of 2 mg/kg of YXY101. The results in FIG. 7A showed that YXY101 inhibits the progression of breast cancer tumors.

FIG. 7B showed the results of HE staining and immunohistochemical staining of tumor tissues of MMTV-PYVT mice at 11 weeks, 13 weeks or 17 weeks after intragastric administration of 2 mg/kg of YXY101 for two weeks. The results of FIG. 7B showed that YXY101 can inhibit the proliferation of breast cancer tumors.

FIG. 7C showed the analytic results of weight, morphology, HE staining and immunohistochemical staining of lung tissue of MMTV-PYVT mice at 11 weeks, 13 weeks or 17 weeks after intragastric administration of 2 mg/kg of YXY101 for two weeks. The results of FIG. 7C showed that YXY101 can inhibit lung metastasis caused by breast cancer.

The experimental results in FIGS. 7A-7C indicated that YXY101 was capable of inhibiting the proliferation and metastasis of breast cancer tumors.

FIG. 8A showed, at the animal level, the survival curves of wild-type mmtv-PyMT mice and Nur77-knocked-out mmtv-PyMT mice within 60 days, and FIG. 8D showed the effect of YXY101 on the survival rate of mmtv-PyMT mice detected at the animal level. The results showed that the survival rate of mice after knockingout of Nur77 was significantly improved, predicting that Nur77 was significantly associated with the development of breast cancer. FIG. 8B showed the statistical results of the tumor tissue weight of the above two kinds of mice, and the results showed that the weight of breast cancer tissue significantly decreased after knocking out of Nur77, and FIG. 8C also showed the comparison in appearance and morphology of these tumor tissues, clearly indicating the Nur77-knocked-out mice had smaller and smoother tumor tissue. The above results indicated that Nur77 played a crucial role in the development of breast cancer.

In summary, we creatively screened drug targeting at Nur77 by using SPR technology, thereby obtaining the drug molecule YXY101 that specifically binds to Nur77, it showed significant anti-tumor activity, especially sensitive to triple-negative breast cancer, and this therapeutic activity for breast cancer was dependent on Nur77. The compound was a very promising active molecule for the treatment of triple negative breast cancer, and the screening method was an effective way to develop drug molecule that specifically binds to Nur77 and for the target treatment of triple negative breast cancer.

EXAMPLE 7. INFLAMMATION CAN INDUCE TUMORIGENESIS TO A CERTAIN EXTENT, AND THIS PROCESS IS Nur77 RELEVANT

In the previous study, we found that the development of breast cancer, especially triple-negative breast cancer, was also accompanied by inflammatory response and high activation of mTOR signaling pathway. Chronic inflammation was also an important basis for the development of breast cancer, and many non-steroidal anti-inflammatory drugs effective to other tumors had also been used for the prevention and treatment of breast cancer.

FIGS. 9A-9B showed p-P70S6K levels of MB-MDA-231 and SKBR3 breast cancer cells treated with TNFα for 1 h, 3 h, and 6 h under starvation conditions, detected by immunoblotting. The results showed that p-P70S6K was up-regulated under the induction of TNFα, and this was time-dependent. The results indicated that the mTOR signaling pathway was activated in an inflammatory environment, which might be closely related to tumorigenesis. FIG. 9C showed levels of p-mTOR, p-P70S6K, and p-S6 in wild-type or Nur77-knocked-out MEF cells treated with TNFα in gradient concentration or gradient time under starvation conditions, detected by immunoblotting. The results showed that the activation of mTOR signaling pathway caused by TNFα can be regulated by time and concentration, and such activation was dependent on Nur77.

In combination with Example 6 and Example 7, Nur77 was not only important for the development of breast cancer, but also can be used as a target for the treatment of breast cancer. Therefore, Nur77 was a valuable biochemical indicator for the detection of development of breast cancer, and can be used to evaluate breast cancer progression and treatment strategies.

EXAMPLE 8. YXY101 WAS ABLE TO SIGNIFICANTLY INHIBIT mTOR ACTIVITY, WHICH IN TURN INHIBITS TUMORS, AND THIS PROCESS RELIES ON Nur77

In this section, the internal environment of tumor was experimentally simulated, that was, TNFα, a cytokine that caused acute inflammation, was used to simulate tumorigenesis. This method could provide an experimental basis for screening drugs inhibiting tumors. By this method, Nur77-dependent compounds that inhibited the mTOR signaling pathway were screened to find a drug effective in the targeting treatment of triple-negative breast cancer.

FIG. 10A showed the test results of p-mTOR, p-P70S6K levels in MB-MDA-231 breast cancer cells treated with TNFα (20 ng/ml), YXY101 (1 μM, 2 μM, 4 μM) under starvation conditions, detected by immunoblotting. The results showed that YXY101 can significantly down-regulate p-mTOR and p-P70S6K activated by TNFα, suggesting that the anti-tumor mechanism of the compound was through its inhibition of mTOR activity. FIG. 10B showed the test results of p-mTOR, p-P70S6K, Nur77 levels in MB-MDA-231 breast cancer cells transfected with Flag empty plasmid or Flag-Nur77 plasmid, and treated with TNFα, YXY101 for 3 h, 6 h under starvation conditions, detected by immunoblotting. FIG. 10C showed the test results of p-P70S6K and Nur77 levels in MB-MDA-231 cells, which were treated to silence Nur77 gene, and then with TNFα, YXY101 under starvation conditions, detected by immunoblotting. FIG. 10D showed the test results of p-S6, p-mTOR, and p62 levels in wild-type or Nur77-knocked-out type MEF cells treated with TNFα, YXY101 (0.5 Mm, 1 μM), detected by immunoblotting. It indicated from the results of FIGS. 10B-10D that, through ways of overexpression and knockout of Nur77, the activity of YXY101 of down-regulating mTOR activity was confirmed as depending on Nur77.

In conclusion, the inhibition of mTOR signaling pathway can be used as an effective indicator for screening anticancer drugs. By this method, compounds screened having potent activity of inhibiting mTOR signaling pathway via Nur77 have potential anticancer activity.

EXAMPLE 9. INDUCTION OF APOPTOSIS OF YXY101 DERIVATIVES ON TRIPLE-NEGATIVE BREAST CANCER CELLS

Different breast cancer cells (MDA-MB-231 and MCF-7) were treated with different concentrations of YXY101 derivative XS0503 (0.16 μM, 0.31 μM, 0.625 μM, 1.25 μM, 2.5 µM, 5 µM, 10.0 µM) for 24 h, and the proliferation ratio of breast cancer cells were measured. Curves of the cancer cell proliferation ratio in relation to the concentrations of XS0503 were plotted, and the IC50 of YXY101 was determined. The results were shown in FIG. 11A.

FIG. 11A showed the curves of the proliferation ratio of different breast cancer cells (MDA-MB-231 and MCF-7) in relation to XS0503 concentrations, as well as the IC50 value of XS0503; wherein MDA-MB-231 was represented by red curves; MCF-7, a three positive breast cancer cell, was represented by blue curves. The results showed that the inhibitory ability of XS0503 on the proliferation of triple-negative breast cancer cells was significantly stronger than that on triple-positive breast cancer cells; wherein, the IC50 of XS0503 for inhibiting the proliferation of MDA-MB-231 was 1.19 µM, which was lower than that for MCF-7 (2.65 µM). This suggested that YXY101 can be used particularly advantageously for the treatment of triple negative breast cancer.

Further, MDA-MB-231 was treated with different YXY101 derivatives, XS0077, XS0335, XS0419, XS0474, or XS0488 (0.16 µM, 0.31 µM, 0.625 µM, 1.25 µM, 2.5 µM, 5 µM, 10.0 µM), followed by measurement of MDA-MB-231 proliferation ratio. The results in FIG. 11B showed that the IC50 for the inhibition of proliferation of MDA-MB-231 treated with XS0077, XS0335, XS0419, XS0474 and XS0488 were 1.84 µM, 1.88 µM, 1.27 µM, 2.93 µM, and 1.90 µM, respectively.

FIG. 11C showed the inhibition rate analysis results of seven breast cancer cells, BT474, ZR-75-1, BT549, HCC1937, HS578T, MCF-7, and T47D, which have been treated with YXY101 derivatives, XS0284, XS0285, XS0394, XS0418, XS0419, XS0474, XS0486, XS0462, XS0491, XS0492, or XS0488. The results showed that the above derivatives had certain inhibitory effects on different breast cancer cells, wherein XS0284, XS0285, XS0418, XS0419, XS0462 and XS0488 had inhibitory effects on the proliferation of various breast cancer cells, which were close or even stronger than that of YXY101.

Further, YXY101 (4 µM) or different YXY101 derivatives (4 µM), XS0394, XS0395, XS0419, XS0420, XS0421, XS0284, XS0335, XS0488, XS0491, XS0492, XS0418, XS0502, XS0503, XS0506, XS0507, XS0508, or XS0077, and TNFα (20 ng/ml) were used to treat MDA-MB-231 cells and PARP in the cells were subjected to immunoblotting analysis. The results FIG. 12A showed that, in comparison with YXY101, the red font-labeled derivatives including XS0418, XS0419, XS0492, XS0508 and XS0077 can more significantly induce PARP cleavage in triple negative breast cancer of MDA-MB-231 cells.

FIG. 12B showed the results of immunoblotting analysis of P-mTOR, P-p70S6K, and P—S6 in MDA-MB-231 cells under starvation treatment with serum-free medium for 10 h, and treated with YXY101 (2 µM) and different YXY101 derivatives (2 µM), XS0284, XS0285, XS0335, XS0394, XS0418, XS0419, XS0454, XS0462, XS0473, XS0474, XS0480, XS0486, XS0488, XS0491, or XS0492, and TNFα (20 ng/ml). In comparison with YXY101, the red font-labeled derivatives including XS0335, XS0394, XS0418, XS0419, XS0474, XS0486, XS0491 and XS0492 can more significantly reduce P-mTOR, P-p70S6K, and P—S6.

EXAMPLE 10. CHARACTERIZATION OF OTHER COMPOUNDS BY SURFACE PLASMON RESONANCE (SPR)

According to the methods described in Examples 1 and 2, the binding of various YXY101 derivatives (XS0418, XS0419, XS0474, XS0394, XS0492, XS0491, XS0488) to Nur77-LBD was detected by SPR using Biacore T200 instrument. The results were shown in FIG. 13.

FIG. 13 showed the results of experiment for detecting the binding of various compounds (XS0418, XS0419, XS0474, XS0394, XS0492, XS0491, XS0488) to Nur77-LBD using Biacore T200 instrument. The results showed that the dissociation constant (Kd) of the compound XS0418 to Nur77-LBD is 3.67 µM; the dissociation constant (Kd) of the compound XS0419 to Nur77-LBD is 404 nM; the dissociation constant (Kd) of the compound XS0474 to Nur77-LBD is 2.60 µM; the dissociation constant (Kd) of the compound XS0394 to Nur77-LBD is 1.26 µM; the dissociation constant (Kd) of the compound XS0492 to Nur77-LBD is 1.30 µM; the dissociation constant (Kd) of the compound XS0491 to Nur77-LBD is 0.336 µM; the dissociation constant (Kd) of the compound XS0488 to Nur77-LBD is 1.28 µM.

EXAMPLE 11. XS0284 IS MORE EFFECTIVE IN TREATING HYPERLIPEMIA INDUCED BREAST CANCER THAN YXY101

In order to prove that YXY101 derivatives can also inhibit breast cancer, we selected XS0284 showing strong inhibitory effect on P-mTOR, P-p70S6K and P—S6 for confirmation. The results of FIGS. 14A-14D showed that both of YXY101 and XS0284 can significantly inhibit the development of breast cancer, whether under low-fat feeding conditions or high-fat feeding conditions. Under low-fat feeding conditions, the inhibitory effect of XS0284 on breast cancer was close to that of YXY101, while under high-fat feeding conditions, the inhibition effect of XS0284 was stronger than that of YXY101. The above conclusions can be reflected in the size of tumor tissue and the change of body weight of mice.

These results indicated that a series of YXY101 derivatives (such as XS0284) can also inhibit tumor development, and they were even superior to YXY101 in term of tumor inhibition.

EXAMPLE 12. THE TUMOR INHIBITION EFFECTS OF YXY101 AND ITS DERIVATIVES IS DEPENDENT ON Nur77

In order to prove the anti-tumor effect of YXY101 and its derivatives is relied on Nur77, we selected YXY101 and its derivative XS0284, which showed significant inhibitory effect on P-mTOR, P-p70S6K and P—S6 for confirmation. FIGS. 15A-15B showed the results of two types of PYVT mice, wild type and Nur77-knocked-out type, which had been intragastrically administered with YXY101 (5 mg/kg) or XS0284 (10 mg/kg) respectively for two weeks. By comparing the tumor tissue size of each experimental group, the results showed that YXY101 and XS0284 were effective in inhibiting tumors in wild-type mice, but neither of the two compounds could exert an inhibitory effect on Nur77-deficient mice.

The above results indicated that YXY101 and its derivatives rely on Nur77 to exert their tumor suppressing effect.

EXAMPLE 13. THE ACUTE TOXIC-SIDE EFFECTS OF XS0284 ARE LOWER THAN YXY101

In this example, acute toxicity model mice were established by single intragastric injection of 200 mg/kg of YXY101 or its derivative XS0284 or by single intraperitoneal injection of 20 mg/kg of YXY101 or its derivative XS0284. In this example, after intragastric administration or intraperitoneal injection of YXY101 or XS0284, the mice were observed for food intake, drinking of water, spontaneous activity, mental state, movement of the limbs, bowel quality, hair gloss, etc., and any possible toxic reactions and time points of oneset as well as offset thereof were recorded in details. The tissue morphologies of the heart, liver, small intestine, white fat and kidney were observed by Histopathological method.

The experimental results were shown in FIG. 16. FIG. 16A showed the intragastric injection group: 1) the cardiomyocytes of the mice from the control group had clear boundaries, with ample and obvious nuclei, the myocardial fibers were arranged neatly and clearly; in the liver tissue, the sinus hepticus was ample and clear, the lobuli hepatis had clear boundary; the intestinal tissue had clear boundaries, the cells were plump, the intestinal villi with obvious boundaries were arranged neatly; the adipose tissue cells had clear boundaries and were arranged neatly. 2) Compared with the control group, the myocardial cells and myocardial fibers of the mice from the YXY101 group were arranged disorderly; the lobuli hepatis boundaries were blurred, the cytoplasm was reduced, and most of the hepatocytes died; the intestinal tissue was swollen apparently, the cell death increases, the inflammatory reaction was obvious, the intestinal villi were arranged disorderly; the adipose tissue cells were arranged disorderly and some of the fibers were broken. 3) Compared with the blank group, the cardiac myocytes of the mice from the XS0284 group had relatively clear boundaries, the myocardial fibers were arranged relatively neatly and had obvious boundaries; the hepatocytes in the liver tissue had obvious boundaries and clear structure; the intestinal tissue had clear boundaries, the cells were plump, the intestinal villi were neatly arranged and had obvious boundaries; the adipose tissue cells had clear boundaries, and were neatly arranged, and the fiber breakage was reduced. It can be concluded that the XS0284 group showed a weaker toxic effect on the liver and small intestine than YXY101.

FIG. 16B showed the intraperitoneal injection group. 1) The cardiomyocytes of the mice from the control group had clear boundaries, with ample and obvious nuclei, the myocardial fibers were arranged neatly and had clear boundaries; in the liver tissue, the sinus hepticus was ample and clear, the lobuli hepatis had clear boundaries; the adipose tissue cells had clear boundaries and were arranged neatly; the glomeruli of the kidney tissue had clear boundaries, the cells were plump and were arranged neatly and had obvious boundaries. 2) Compared with the control group, the myocardial cells and myocardial fibers of the mice from the YXY101 group were arranged disorderly; the lobuli hepatis had substantially obvious boundaries, the hepatocytes were plump and had normal morphology; but the adipose tissue cells were arranged disorderly and had many inflammatory cell infiltration; the kidney tissue had blurred glomerulus boundaries and many inflammatory cell infiltration, and the arrangement was not neat. 3) Compared with the control group, the cardiac cardiomyocytes of the mice from the XS0284 group had relatively clear boundaries, the myocardial fibers were relatively neatly arranged and had obvious boundaries; the hepatocytes in the liver tissue had obvious boundaries and clear structure; the adipose tissue cells had clear boundaries and were arranged neatly, the fiber breakage was reduced; the kidney tissue had clear glomerular boundaries, the cells were full, and there was a small amount of inflammatory cell infiltration. It can be concluded that the XS0284 group of the intraperitoneal injection group showed less toxicity to kidney and adipose than YXY101.

These results indicated that a series of derivatives of YXY101, such as XS0284, had less acute toxicity to animals than YXY101. It further suggested that this series of compounds had stronger targeting and specificity than YXY101, and this series of YXY101 derivatives was possibly to be developed as a safer anticancer drug.

Preparation of Compound XS0077

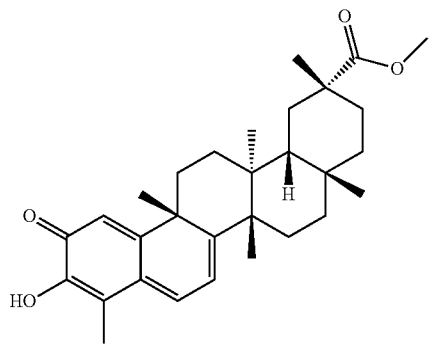

Compound YXY101 (50 mg, 0.11 mmol) was dissolved in 2 mL of DMF with stirring, followed by an addition of sodium hydrogencarbonate (56 mg, 0.66 mmol) and methylene chloride (42 µL, 0.66 mmol), then subjected to an reaction with stirring at room temperature for 12 hours. The reaction was quenched with 1 mol/L HCl (1 mL), then the resulting mixture was added with 9 mL of purified water, and extracted with ethyl acetate three times (5 mL each time). The organic layer was collected, dried over anhydrous sodium sulfate, and then subjected to vacuum evaporation to remove organic solvent ethyl acetate, thereby obtaining an orange-red solid of mixed crude product. The orange-red solid product was obtained by column chromatography, n-hexane and ethyl acetate (hexane/ethyl acetate=10:1) was used as eluent, and the column was packed with 300-400 mesh silica gel.

$^1$H NMR (600 MHz, DMSO-d6) δ ppm 0.44 (s, 3H), 0.91 (d, J=14.31 Hz, 1H), 1.07 (s, 3H), 1.12 (s, 3H), 1.21 (s, 3H), 1.30-1.35 (m, 1H), 1.38 (s, 3H), 1.41-1.46 (m, 1H), 1.50-1.59 (m, 3H), 1.61-1.72 (m, 4H), 1.78-1.86 (m, 1H), 1.95 (td, J=13.98, 3.76 Hz, 1H), 2.06 (d, J=14.12 Hz, 1H), 2.09 (s, 3H), 2.17-2.22 (m, 1H), 2.31 (d), J=15.77 Hz, 1H), 3.48 (s, 3H), 6.35 (d, J=7.15 Hz, 1H), 6.39 (d, J=1.28 Hz, 1H), 7.07 (dd, J=7.15, 1.10 Hz, 1H), 8.72 (s, 1H).

$^{13}$C NMR (151 MHz, DMSO-d6) δ ppm 10.10, 17.96, 21.41, 28.08, 29.19, 29.42, 30.12, 30.34, 31.34, 32.23, 32.91, 34.39, 36.02, 37.83, 38.8, 39.83, 41.99, 43.64, 44.48, 51.44, 117.26, 118.05, 120.18, 126.89, 133.13, 146.42, 162.94, 167.80, 177.93, 177.96.

EXAMPLE 15. PREPARATION OF COMPOUND XS0284

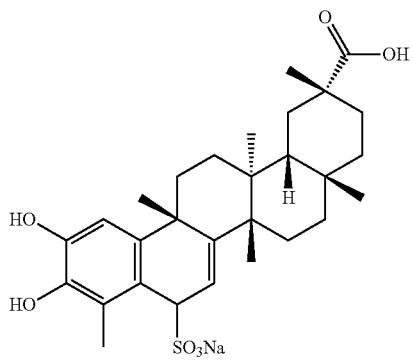

Compound YXY101 (50 mg, 0.11 mmol) was dissolved in methanol (2.5 mL) with stirring under nitrogen atmosphere. Followed by an addition of an aqueous solution of sodium hydrogen sulfite (14 mg, 0.13 mmol, dissolved in 1 mL of water) and allowed to react at room temperature for 3 hours. After the reaction, the reaction system was concentrated by a rotary evaporator to give colorless crystals. The colorless crystals were recrystallized from methanol/water, and the obtained product was dried in vacuo to afford compound XS0284 (56.6 mg) as white solid.

$^1$H NMR (600 MHz, DMSO-d6) δ ppm 0.59 (s, 3H) 0.86 (d, J=12.10 Hz, 1H) 1.05 (s, 3H) 1.09 (s, 3H) 1.18 (s, 3H) 1.43-1.60 (m, 6H) 1.62 (s, 3H) 1.78-1.85 (m, 1H) 1.93-2.04 (m, 3H) 2.21 (s, 3H) 2.32 (d, J=15.22 Hz, 1H) 4.48 (d, J=6.24 Hz, 1H) 5.81 (d, J=6.60 Hz, 1H) 6.58 (s, 1H) 7.61 (br.s., 1H) 8.81 (br.s., 1H).

$^{13}$C NMR (151 MHz, DMSO-d6) δ ppm 13.57, 18.46, 21.64, 29.04, 29.98, 30.47, 30.60, 30.64, 31.94, 32.92, 34.80, 35.11, 36.90, 36.96, 37.90, 38.07, 43.95, 44.39, 60.19, 108.96, 118.87, 123.26, 124.39, 140.89, 141.93, 144.02, 150.07, 180.00.

EXAMPLE 16. PREPARATION OF COMPOUND XS0285

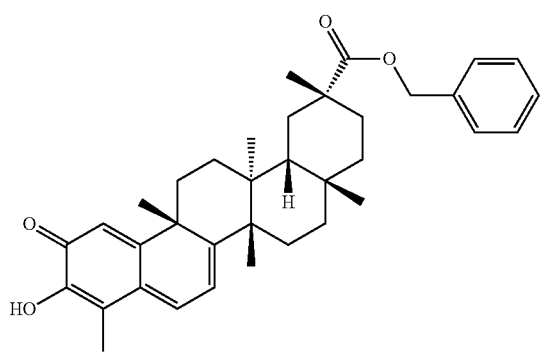

Compound YXY101 (50 mg, 0.11 mmol) was dissolved in N,N-dimethylformamide (2 mL) with stirring. Sodium hydrogencarbonate (50.4 mg, 0.6 mmol) was added, then benzyl bromide (0.17 mg, 20 μL) was added, and the reaction was carried out under stirring at room temperature for 24 hours. The reaction was stopped, and the reaction mixture was added with deionized water (15 mL), and extracted with ethyl acetate for three times. The combined ethyl acetate layer was washed with saturated aqueous solution of NaCl three times, dried over anhydrous Na$_2$SO$_4$, concentrated by a rotary evaporator to give a crude product (dark red-brown oily matter). The crude product was separated and purified by a rapid column chromatography (ethyl acetate:n-hexane) and dried in vacuo to afford compound XS-0285 (44 mg) as red solid.

$^1$H NMR (600 MHz, CHLOROFORM-d) δ ppm 0.50 (s, 3H) 0.97 (d, J=13.75 Hz, 1H) 1.09 (s, 3H) 1.21 (s, 3H) 1.22-1.25 (m, 3H) 1.25-1.28 (m, 1H) 1.41 (s, 3H) 1.47-1.58 (m, 3H) 1.58-1.72 (m, 5H) 1.87 (d, J=6.05 Hz, 1H) 1.99-2.11 (m, 3H) 2.21 (d, J=1.65 Hz, 3H) 2.24 (d, J=14.12 Hz, 1H) 2.44 (d, J=15.77 Hz, 1H) 4.93 (d, J=12.29 Hz, 1H) 5.02 (d, J=12.47 Hz, 1H) 6.32 (d, J=7.15 Hz, 1H) 6.49 (s, 1H) 7.01 (d, J=6.97 Hz, 1H) 7.27-7.30 (m, 2H) 7.30-7.36 (m, 3H).

$^{13}$C NMR (151 MHz, CHLOROFORM-d) δ ppm 10.29, 18.53, 21.58, 28.61, 29.53, 29.90, 30.55, 30.76, 31.57, 32.76, 33.27, 34.69, 36.35, 38.25, 39.43, 40.44, 42.93, 44.25, 45.03, 66.32, 117.36, 118.12, 119.62, 127.38, 128.24, 128.32, 128.64, 134.24, 135.68, 146.06, 164.79, 170.27, 177.95, 178.36.

EXAMPLE 17. PREPARATION OF COMPOUND XS0335

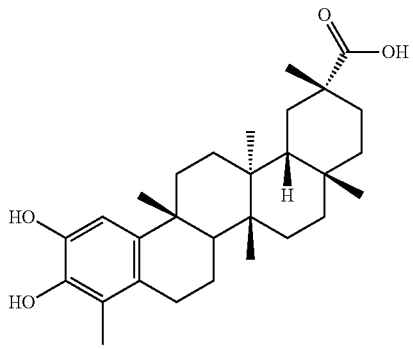

Compound YXY101 (50 mg, 0.11 mmol) was dissolved in dichloromethane (1 mL) with stirring. Palladium carbon (5 mg) was added, then dichloromethane (1 mL) was added, and hydrogen was continuously introduced, and reacted at room temperature for 24 hrs. The reaction was stopped. The reaction mixture was added with deionized water (15 mL), extracted with ethyl acetate three times. The ethyl acetate layers were combined, then washed three times with saturated NaCl, dried over anhydrous Na$_2$SO$_4$, concentrated by a rotary evaporator to give a crude product (colorless oily matter). The crude product was separated and purified by a rapid column chromatography (ethyl acetate:n-hexane) and dried in vacuo to afford compound XS-0335 (46 mg) as white solid.

$^1$H NMR (600 MHz, METHANOL-d$_4$) δ ppm 0.93-1.00 (m, 2H) 1.03 (s, 3H) 1.11 (s, 3H) 1.19 (t, J=3.48 Hz, 4H) 1.26 (s, 3H) 1.41-1.45 (m, 6H) 1.47-1.55 (m, 2H) 1.57 (d, J=8.25 Hz, 1H) 1.59-1.68 (m, 2H) 1.83-1.98 (m, 3H) 2.06-2.11 (m, 4H) 2.11-2.20 (m, 4H) 2.43 (d, J=15.77 Hz, 1H) 2.68 (d, J=14.67 Hz, 1H) 6.67 (s, 1H).

$^{13}$C NMR (151 MHz, METHANOL-d$_4$) δ ppm 11.94, 18.51, 20.54, 26.82, 28.66, 30.74, 31.15, 31.57, 31.61, 32.02, 32.09, 32.32, 33.63, 34.65, 37.09, 37.56, 38.53, 39.45, 39.85, 41.69, 58.12, 58.48, 112.24, 121.74, 129.36, 141.47, 142.39, 144.19, 182.95.

EXAMPLE 18. PREPARATION OF COMPOUNDS XS0366, XS0434-XS0438, XS0440, XS0441, XS0443, XS0463 AND XS0464

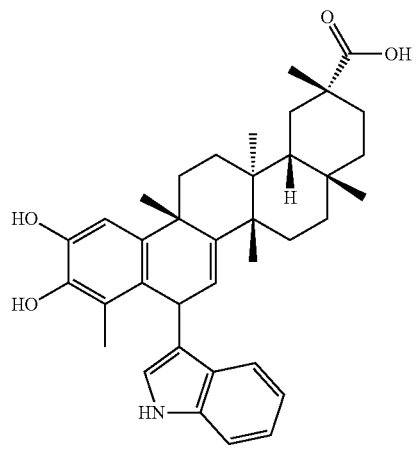

XS0366

Taking the preparation of XS0366 for example, compound YXY101 (100 mg, 0.22 mmol) was dissolved in dichloromethane (4 mL) under stirring. Indole (52 mg, 0.44 mmol) was added, followed by an addition of aluminum trichloride hexahydrate (5.3 mg, 0.022 mmol), and the reaction was conducted under stirring at room temperature for 5 hours. The reaction was stopped, and the reaction system was added with deionized water (15 mL), then extracted three times with ethyl acetate. The combined ethyl acetate layer was washed with saturated NaCl three times, dried over anhydrous $Na_2SO_4$, and concentrated by a rotary evaporator to obtain a crude product (brown oily matter). The crude product was separated and purified by rapid column chromatography (ethyl acetate:n-hexane), dried in vacuo to afford compound XS0366 (122.2 mg) as purple red solid.

$^1$H NMR (600 MHz, CHLOROFORM-d) δ ppm 0.73 (br. s., 3H) 0.87-0.90 (m, 1H) 0.95-1.00 (m, 3H) 1.01 (br. s., 3H) 1.14 (br. s., 3H) 1.19 (t, J=7.06 Hz, 1H) 1.25-1.27 (m, 1H) 1.34 (br. s., 3H) 1.42-1.57 (m, 4H) 1.57-1.76 (m, 4H) 1.90 (s, 3H) 1.99-2.07 (m, 2H) 2.10-2.17 (m, 1H) 2.40 (d, J=15.04 Hz, 1H) 4.90 (d, J=5.69 Hz, 1H) 6.21 (d, J=6.24 Hz, 1H) 6.23 (br. s., 1H) 6.79 (br. s., 1H) 7.11 (t, J=7.43 Hz, 1H) 7.16 (t, J=7.43 Hz, 1H) 7.28 (d, J=7.89 Hz, 1H) 7.75 (d, J=7.70 Hz, 1H) 7.88 (br. s., 1H).

$^{13}$C NMR (151 MHz, CHLOROFORM-d) δ ppm 11.53, 18.84, 21.93, 28.89, 29.63, 29.75, 30.40, 30.54, 30.72, 31.55, 32.84, 34.62, 35.50, 36.74, 36.94, 37.76, 40.35, 43.62, 44.28, 108.93, 111.30, 119.09, 119.28, 120.23, 121.55, 121.58, 121.67, 127.10, 127.84, 136.49, 139.92, 142.17, 142.83, 147.48, 184.30.

According to the above method, the following compounds were also synthesized in the present invention:

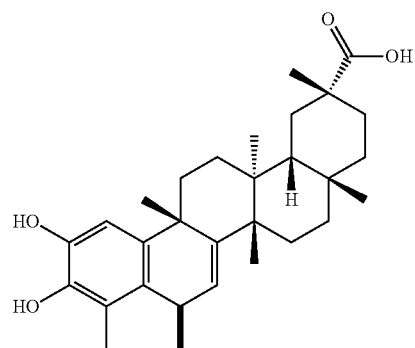

XS0434

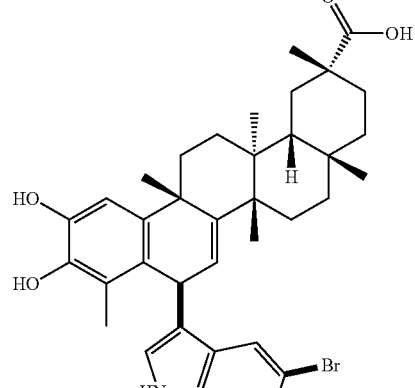

XS0435

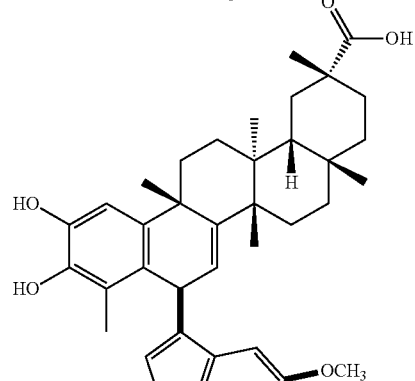

XS0436

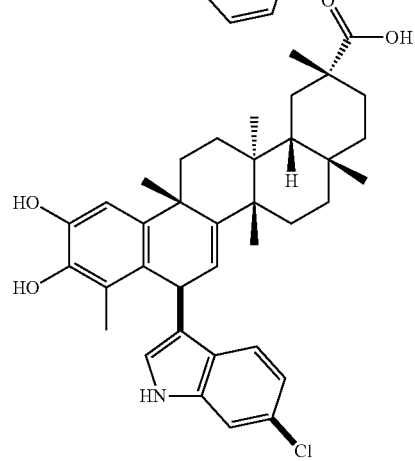

XS0437

71
-continued
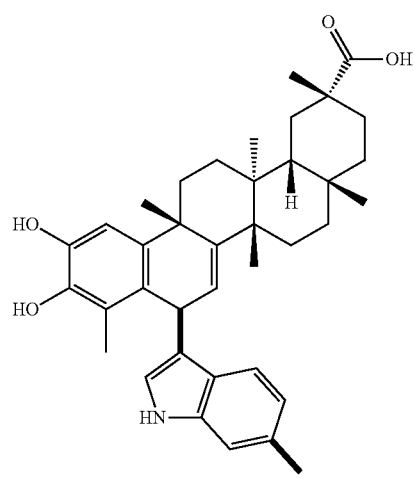
XS0438
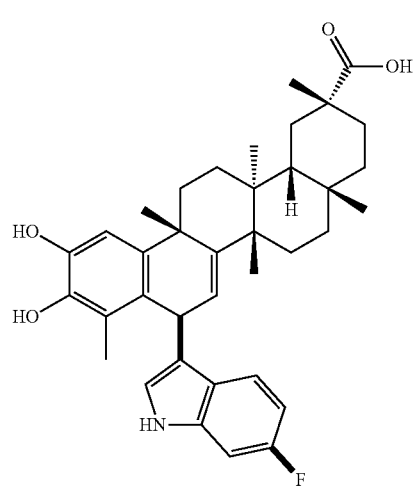
XS0440
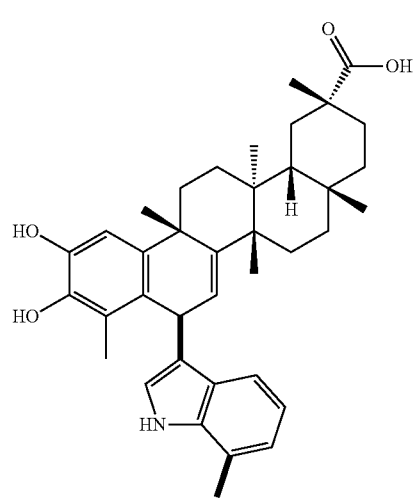
XS0441
72
-continued
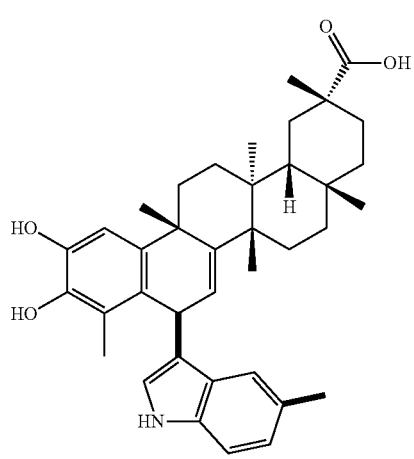
XS0443
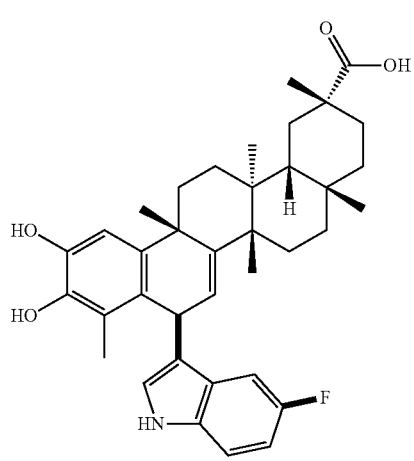
XS0463
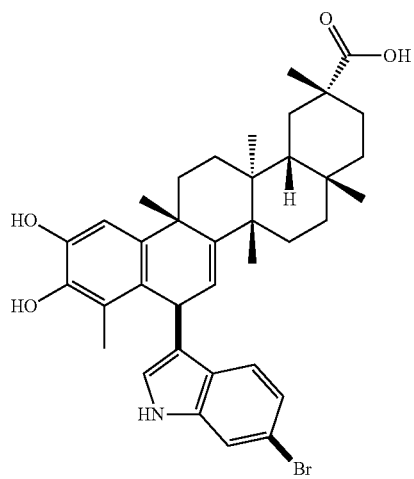
XS0464

EXAMPLE 19. PREPARATION OF COMPOUND XS0395

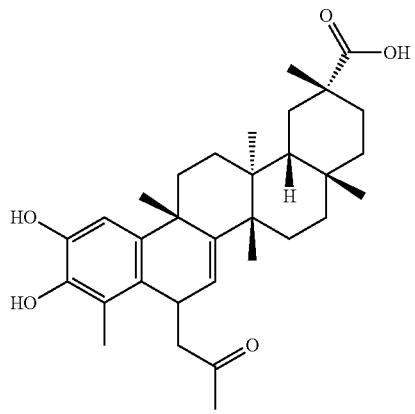

Compound YXY101 (50 mg, 0.11 mmol) was weighed in a 25 ml reaction flask, and 4 ml of acetone was added thereto and dissolved under stirring, and then a drop of concentrated hydrochloric acid was added as catalyst, and the reaction was carried out at room temperature for 12 hours. The reaction was stopped, and the reaction mixture was directly concentrated to remove solvent. The residue was purified by silica gel column chromatography with ethyl acetate:n-hexane=4:1, affording a white solid in a yield of 51%.

$^1$H NMR (600 MHz, DMSO-d6) δ ppm 0.62 (s, 3H), 0.82-1.86 (m, 1H), 1.04 (s, 3H), 1.09 (s, 3H), 1.15 (s, 3H), 1.25-1.38 (m, 4H), 1.39 (s, 3H), 1.42-1.50 (m, 2H), 1.55-1.71 (m, 4H), 1.77 (td, J=13.9, 6.1 Hz, 1H), 1.93-2.02 (m, 2H), 2.03 (s, 3H), 2.09 (s, 3H), 2.27-2.36 (m, 2H), 2.67 (dd, J=16.2, 2.7 Hz, 1H), 3.71-3.78 (m, 1H), 5.72 (d, J=6.4 Hz, 1H), 6.63 (s, 1H), 7.91 (s, 1H), 8.94 (s, 1H), 12.06 (br.s., 1H).

$^{13}$C NMR (151 MHz, DMSO-d6) δ ppm 11.64, 18.43, 22.63, 29.01, 29.90, 30.36, 30.47, 30.62, 30.77, 31.44, 31.87, 32.88, 32.92, 34.94, 35.60, 36.79, 36.85, 36.98, 37.74, 39.87, 43.74, 44.36, 51.72, 109.06, 120.00, 122.04, 126.53, 140.46, 141.62, 143.85, 149.91, 179.96.208.01.

EXAMPLE 20. PREPARATION OF COMPOUND XS0419

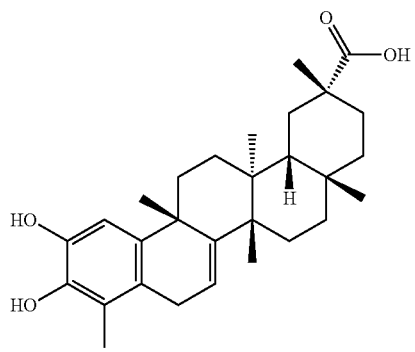

Compound YXY101 (50 mg, 0.11 mmol) was dissolved under stirring in 2 mL of deuterated methanol, then sodium borohydride (44 mg, 1.1 mmol) was added, the reaction was carried out at room temperature for 30 min. The reaction was quenched with 1 mol/L HCl (1 mL), and then 9 mL of pure water was added, and extracted with dichloromethane (5 mL each time) three times. The organic layers were combined, dried over anhydrous sodium sulfate, and then the organic solvent dichloromethane was rapidly removed by vacuum distillation to obtain compound XS0419 (50.1 mg) as a white solid.

$^1$H NMR (600 MHz, DMSO-d$_6$) ☐ ppm 0.66 (s, 3H) 0.85 (d, J=13.9 Hz, 1H) 1.05 (s, 3H) 1.11 (s, 3H) 1.17 (s, 3H) 1.22 (s, 3H) 1.29 (ddd, J=13.7, 4.4 Hz, 1H) 1.36-1.41 (m, 1H) 1.43-1.51 (m, 3H) 1.53-1.59 (m, 1H) 1.59-1.63 (m, 1H) 1.63-1.69 (m, 1H) 1.79 (ddd, J=13.8, 6.5 Hz, 1H) 1.86 (ddd, J=13.8, 5.0 Hz, 1H) 1.94-2.00 (m, 2H) 2.01 (s, 3H) 2.04 (d, J=13.6 Hz, 1H) 2.34 (d, J=15.6 Hz, 1H) 2.91 (dd, J=20.0, 1.5 Hz, 1H) 3.18 (dd, J=20.5, 6.2 Hz, 1H) 5.72 (dd, J=6.1, 1.8 Hz, 1H) 6.61 (s, 1H) 7.82 (s, 1H) 8.80 (s, 1H) 12.05 (br. s., 1H).

$^{13}$C NMR (151 MHz, DMSO-d$_6$) ppm 11.53, 18.10, 22.70, 27.30, 28.45, 29.46, 29.77, 30.08, 30.19, 31.39, 32.44, 34.06, 34.09, 34.40, 36.07, 36.56, 37.14, 39.44, 43.25, 43.83, 108.17, 117.67, 120.10, 123.10, 139.35, 140.56, 143.11, 149.22, 179.51.

EXAMPLE 21. PREPARATION OF COMPOUND XS0462

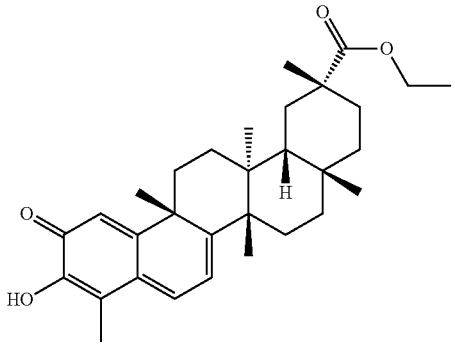

First, Celastrol (135.2 mg, 0.3 mmol) was dissolved in 2 mL of DMF under stirring, followed by an addition of sodium hydrogencarbonate (138.6 mg, 1.65 mmol) and ethyl bromide (234 μL, 0.15 mmol), the reaction was carried out under stirring at room temperature for 12 hours. The reaction was quenched with 1 mol/L HCl (1 mL), 9 mL of pure water was added. The resulting mixture was extracted three times with ethyl acetate (15 mL each time). The organic layers were combined, dried over anhydrous sodium sulfate, and then the organic solvent ethyl acetate was removed by vacuum evaporation to afford a crude product as orange-red mixture solid. The crude product was separated by column chromatography with n-hexane and ethyl acetate (hexane/ethyl acetate=10:1) as eluent, using 300-400 mesh silica gel packed column, affording an orange-red solid product.

$^1$H NMR (600 MHz, DMSO-d$_6$) δ ppm 0.47 (s, 3H), 0.91 (d, J=14.1 Hz, 1H), 1.07 (s, 3H), 1.11 (s, 3H), 1.12-1.15 (m, 3H), 1.21 (s, 3H), 1.31-1.36 (m, 1H), 1.38 (s, 3H), 1.41-1.46 (m, 1H), 1.52-1.58 (m, 3H), 1.61-1.71 (m, 4H), 1.78-1.87 (m, 1H), 1.90-1.99 (m, 1H), 2.03-2.08 (m, 1H), 2.09 (s, 3H), 2.21 (d, J=11.2 Hz, 1H), 2.34 (d, J=15.6 Hz, 1H), 3.91 (m, 2H), 6.35 (d, J=7.2 Hz, 1H), 6.39 (s, 1H), 7.05-7.10 (m, 1H), 8.73 (s, 1H).

$^{13}$C NMR (151 MHz, DMSO-d$_6$) δ ppm 10.53, 14.28, 18.50, 21.84, 28.55, 29.57, 29.75, 30.58, 31.76, 32.76, 33.32, 34.78, 36.43, 38.20, 39.27, 40.13, 40.44, 42.43, 44.04, 44.93, 60.33, 117.74, 118.51, 120.56, 127.29, 133.67, 146.86, 163.40, 168.31, 177.83, 178.41.

EXAMPLE 22. PREPARATION OF COMPOUND XS0474

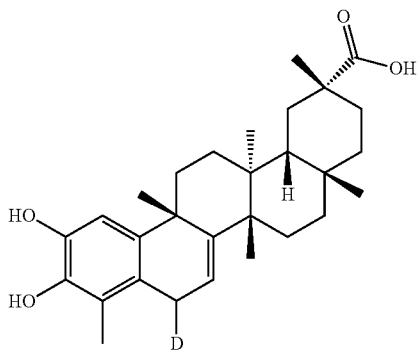

Compound YXY101 (50 mg, 0.11 mmol) was dissolved under stirring in 2 mL of deuterated methanol, then sodium borodeuteride (48.4 mg, 1.1 mmol) was added, the reaction was carried out at room temperature for 30 min. The reaction was quenched with 1 mol/L HCl (1 mL), and then 9 mL of pure water was added. The resulting mixture was extracted three times with dichloromethane (5 mL each time). The organic layers were combined, dried over anhydrous sodium sulfate, and then the organic solvent dichloromethane was rapidly removed by vacuum distillation to obtain compound XS0474 (50.2 mg) as a white solid.

$^1$H NMR (600 MHz, DMSO-d$_6$) □ ppm 0.66 (s, 3H) 0.85 (d, J=12.84 Hz, 1H) 1.04 (s, 3H) 1.10 (s, 3H) 1.17 (s, 3H) 1.22 (s, 3H) 1.29 (td, J=13.66, 4.40 Hz, 1H) 1.35-1.41 (m, 1H) 1.43-1.52 (m, 3H) 1.53-1.58 (m, 1H) 1.58-1.63 (m, 1H) 1.63-1.69 (m, 1H) 1.79 (td, J=13.66, 6.60 Hz, 1H) 1.86 (td, J=13.71, 5.04 Hz, 1H) 1.94-1.99 (m, 2H) 2.01 (s, 3H) 2.04 (d, J=12.10 Hz, 1H) 2.34 (d, J=15.59 Hz, 1H) 3.16 (d, J=6.05 Hz, 1H) 5.71 (d, J=6.24 Hz, 1H) 6.61 (s, 1H) 7.82 (s, 1H) 8.83 (s, 1H) 12.03 (br. s., 1H).

$^{13}$C NMR (151 MHz, DMSO-d$_6$) δ ppm 11.60, 18.15, 22.74, 26.98, 28.52, 29.51, 29.83, 30.14, 30.25, 31.45, 32.50, 34.15, 34.21, 34.46, 36.14, 36.62, 37.21, 39.49, 43.31, 43.89, 108.23, 117.68, 120.20, 123.11, 139.45, 140.60, 143.18, 149.32, 179.59.

EXAMPLE 23. PREPARATION OF COMPOUND XS0503

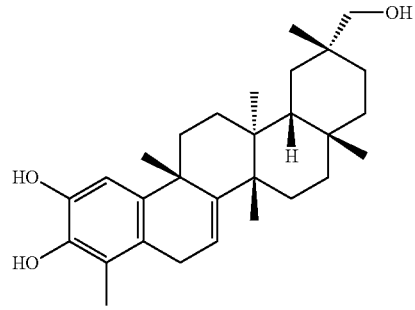

First, pristimerin (250 mg, 0.54 mmol) was dissolved in 20 mL of tetrahydrofuran, followed by an addition of LiAlH$_4$ (1.2 mL, 1.1 mmol), and the reaction was carried out under stirring at room temperature for 2 h. The reaction was quenched with 10 mL of deionized water, and then acidified with 1 mol/L HCl (5 mL). The resulting mixture was performed three times with ethyl acetate (15 mL each time). The organic layers were combined, dried over anhydrous sodium sulfate, and the organic solvent ethyl acetate was removed by vacuum distillation to afford a crude product as orange-yellow mixture solid. The crude product was separated by chromatography column with n-hexane and ethyl acetate (hexane/ethyl acetate=2:1) as eluent, using 300-400 mesh silica gel packed column, affording an orange-yellow solid product.

$^1$H NMR (600 MHz, DMSO-d$_6$) □ ppm 0.76 (s, 3H) 0.83-0.87 (m, 1H) 0.89 (s, 3H) 1.11 (s, 3H) 1.21 (s, 3H) 1.23-1.25 (m, 1H) 1.26 (s, 3H) 1.27-1.34 (m, 2H) 1.48 (dd, J=6.7, 3.9 Hz, 1H) 1.50-1.54 (m, 1H) 1.55-1.59 (m, 1H) 1.60 (d, J=5.0 Hz, 1H) 1.64 (dd, J=9.2, 4.6 Hz, 2H) 1.65-1.69 (m, 2H) 1.69-1.72 (m, 1H) 1.91 (d, J=5.3 Hz, 1H) 1.93-1.97 (m, 1H) 2.02 (s, 3H) 2.92 (d, J=19.4 Hz, 1H) 2.96 (dd, J=10.3, 4.8 Hz, 1H) 3.15-3.20 (m, 1H) 3.21 (t, J=6.0 Hz, 1H) 4.44 (t, J=5.0 Hz, 1H) 5.73 (dd, J=6.1, 1.7 Hz, 1H) 6.61 (s, 1H) 7.80 (s, 1H) 8.78 (s, 1H).

$^{13}$C NMR (151 MHz, CHLOROFORM-d) δ ppm 11.49, 19.35, 25.65, 27.80, 28.10, 28.75, 29.36, 30.31, 30.45, 30.57, 32.27, 32.89, 33.58, 34.24, 36.55, 36.82, 36.95, 37.68, 42.91, 43.15, 71.82, 108.42, 118.15, 120.42, 125.27, 139.96, 141.09, 141.87, 151.04.

EXAMPLE 24. PREPARATION OF COMPOUND XS0508

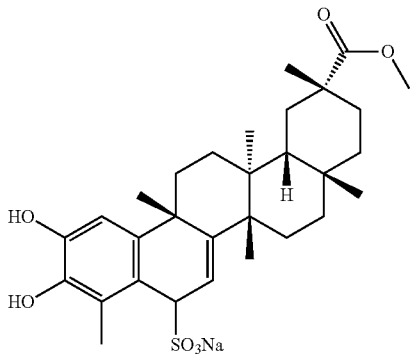

XS0077 (50 mg, 0.11 mmol) was weighed and placed in a 50 ml round bottom bottle and added with 3 ml of methanol for dissolution, the air was replaced with nitrogen for protection, then sodium bisulfite solution (28 mg NaHSO$_{3-1}$ ml H$_2$O, 0.26 mmol) was added, and the reaction was carried out at room temperature for 3 h under protection of nitrogen. The reaction was stopped, the solvent was removed via concentration by distillation under reduced pressure. The residual solid was added with pyridine for dissolution, then filtered and concentrated in vacuo to give a white solid in a yield of 90%.

$^1$H NMR (600 MHz, DMSO-d6) δ ppm 0.57 (s, 3H) 1.07 (s, 3H) 1.12-1.14 (m, 1H) 1.14-1.16 (m, 1H) 1.17 (s, 3H) 1.21 (s, 3H) 1.22-1.23 (m, 2H) 1.24-1.28 (m, 4H) 1.28-1.32 (m, 2H) 1.38 (s, 3H) 1.40-1.46 (m, 2H) 1.47-1.52 (m, 2H) 1.57 (d, J=6.79 Hz, 1H) 1.59-1.63 (m, 4H) 1.64-1.72 (m, 6H)

1.75-1.83 (m, 4H) 1.92-1.96 (m, 1H) 1.97-2.01 (m, 1H) 2.03-2.07 (m, 1H) 2.09 (s, 3H) 2.18 (d, J=10.82 Hz, 2H) 2.73 (d, J=15.04 Hz, 1H) 3.40-3.49 (m, 1H) 3.80-3.89 (m, 1H) 6.36 (d, J=7.34 Hz, 1H) 6.40 (d, J=0.92 Hz, 1H) 7.07 (dd, J=6.97, 0.92 Hz, 1H) 7.73 (d, J=8.07 Hz, 1H) 8.71 (s, 1H).

$^{13}$C NMR (151 MHz, DMSO-d6) δ ppm 10.08, 18.32, 21.83, 24.68, 24.75, 25.13, 25.29, 25.63, 25.67, 28.38, 28.59, 29.91, 30.13, 31.02, 31.08, 31.39, 31.82, 31.91, 31.93, 32.36, 33.10, 36.02, 36.13, 37.67, 38.99, 42.16, 42.81, 44.45, 44.49, 50.05, 54.77, 117.23, 117.93, 120.04, 126.75, 133.25, 146.43, 153.97, 163.09, 168.74, 175.44, 177.83.

EXAMPLE 25. PREPARATION OF COMPOUND XS0536

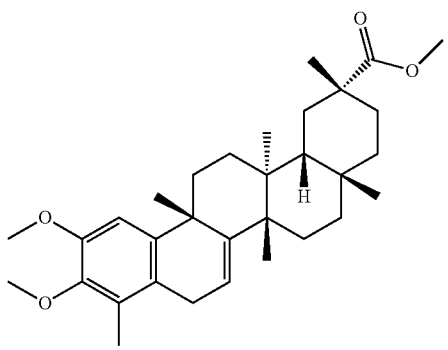

XS0077 (150 mg, 0.32 mmol) was weighed and placed in a heavy wall pressure vessel, added with potassium carbonate (220 mg, 1.6 mmol), and 4 ml of acetone with stirring to dissolve the sample at room temperature, then added with 100 μL of dimethyl sulfate solution; the reaction mixture was transferred to 70° C. oil bath and heated for 8 h. The reaction was quenched with 1 mol/L HCl, followed by an addition of water, then extracted with ethyl acetate three times, dried over anhydrous sodium sulfate, and the solvent was concentrated by a rotary evaporator. The residue was purified by silica gel column chromatography with ethyl acetate:n-hexane=1:20 to afford a pure product as white solid, yield 21%.

$^1$H NMR (600 MHz, CHLOROFORM-d) δ ppm 0.61 (s, 3H) 0.94 (d, J=13.75 Hz, 1H) 1.08 (s, 3H) 1.17 (s, 3H) 1.22 (s, 3H) 1.34 (s, 3H) 1.40 (dd, J=14.12, 4.22 Hz, 1H) 1.44 (dd, J=14.40, 2.84 Hz, 1H) 1.51-1.57 (m, 2H) 1.57-1.63 (m, 1H) 1.63-1.69 (m, 2H) 1.73 (d, J=11.37 Hz, 1H) 1.85 (td, J=13.71, 6.33 Hz, 1H) 2.01-2.07 (m, 1H) 2.07-2.13 (m, 2H) 2.17 (s, 3H) 2.18-2.23 (m, 1H) 2.44 (d, J=15.59 Hz, 1H) 3.02 (d, J=19.99 Hz, 1H) 3.28 (dd, J=20.00, 5.87 Hz, 1H) 3.54 (s, 3H) 3.77 (s, 3H) 3.87 (s, 3H) 5.77 (d, J=4.58 Hz, 1H) 6.78 (s, 1H).

$^{13}$C NMR (151 MHz, CHLOROFORM-d) δ ppm 11.77, 18.28, 22.73, 27.85, 28.85, 29.87, 30.29, 30.50, 30.85, 31.55, 32.88, 34.16, 34.51, 34.79, 36.83, 37.15, 37.52, 40.45, 43.69, 44.33, 51.47, 55.88, 60.30, 106.30, 117.63, 125.49, 127.80, 144.62, 144.80, 149.13, 150.89, 179.05.

EXAMPLE 26. PREPARATION OF COMPOUND XS0286

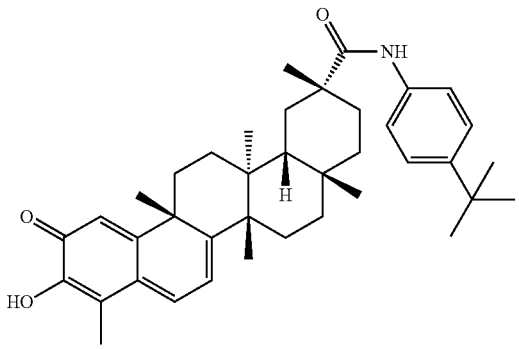

Compound YXY101 (50 mg, 0.11 mmol) was dissolved in N,N-dimethylformamide (2 mL) under stirring. Catalysts EDCl (85.4 mg, 0.55 mmol) and HOBT (74.3 mg, 0.55 mmol) were added and stirred for dissolution; p-tert-butylaniline (49.2 mg, 0.33 mmol) was added, and the reaction was carried out under stirring at room temperature for 36 hours. The reaction was stopped, and the reaction system was added with deionized water (15 mL) and extracted three times with ethyl acetate. The combined ethyl acetate layer was washed with saturated NaCl three times, dried over anhydrous Na$_2$SO$_4$, concentrated by a rotary evaporator to obtain a crude product (dark-red oily matter). The crude product was purified by rapid column chromatography (ethyl acetate:n-hexane), dried in vacuo to afford compound XS0286 (10 mg) as dark-red solid.

$^1$H NMR (600 MHz, CHLOROFORM-d) δ ppm 0.64 (s, 3H) 1.08 (d, J=13.20 Hz, 1H) 1.15 (s, 3H) 1.24-1.27 (m, 6H) 1.40-1.42 (m, 4H) 1.48-1.57 (m, 3H) 1.63 (m, 5H) 1.65-1.79 (m, 5H) 1.85 (d, J=11.92 Hz, 1H) 1.91 (d, J=6.24 Hz, 1H) 1.98-2.06 (m, 3H) 2.08 (d, J=12.10 Hz, 2H) 2.18 (d, J=1.65 Hz, 3H) 2.54 (d, J=15.77 Hz, 1H) 6.29 (d, J=6.79 Hz, 1H) 6.45 (s, 1H) 6.92-7.00 (m, 2H) 7.30-7.34 (m, 2H) 7.34-7.37 (m, 2H) 7.37-7.41 (m, 1H).

$^{13}$C NMR (151 MHz, CHLOROFORM-d) δ ppm 10.21, 18.49, 21.75, 28.58, 29.63, 29.69, 30.41, 30.83, 31.33, 33.24, 33.73, 34.35, 34.98, 36.32, 38.06, 39.38, 41.10, 42.96, 44.47, 45.11, 76.81, 77.02, 77.23, 116.99, 117.95, 119.53, 119.81, 125.89, 127.38, 133.95, 135.11, 146.01, 147.26, 164.68, 170.02, 175.83, 178.38.

EXAMPLE 27. PREPARATION OF COMPOUND XS0287

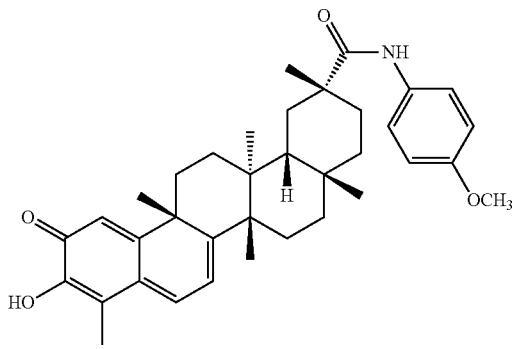

Compound YXY101 (50 mg, 0.11 mmol) was dissolved in N,N-dimethylformamide (2 mL) under stirring. Catalysts EDCl (85.4 mg, 0.55 mmol) and HOBT (74.3 mg, 0.55 mmol) were added and stirred for dissolution; p-methoxyaniline (40.6 mg, 0.33 mmol) was added, and the reaction was carried out under stirring at room temperature for 36 hours. The reaction was stopped. The reaction system was added with deionized water (15 mL) and extracted three times with ethyl acetate. The combined ethyl acetate layer was washed with saturated NaCl three times, dried over anhydrous $Na_2SO_4$, concentrated by a rotary evaporator to obtain a crude product (dark-red oily matter). The crude product was purified by rapid column chromatography (ethyl acetate:n-hexane), dried in vacuo to afford compound XS0287 (20 mg) as dark-red solid.

$^1$H NMR (600 MHz, CHLOROFORM-d) δ ppm 0.53 (s, 3H) 1.05 (d, J=13.94 Hz, 1H) 1.13 (s, 3H) 1.21 (s, 3H) 1.24 (s, 3H) 1.26 (s, 3H) 1.35 (s, 3H) 1.48-1.54 (m, 2H) 1.58 (d, J=7.34 Hz, 2H) 1.64-1.72 (m, 2H) 1.78-1.89 (m, 2H) 2.03-2.11 (m, 2H) 2.18 (s, 3H) 2.55 (d, J=15.77 Hz, 1H) 3.79 (s, 3H) 6.25 (d, J=7.15 Hz, 1H) 6.34 (s, 1H) 6.91 (m, J=8.99 Hz, 2H) 6.96 (d, J=7.15 Hz, 1H) 7.40 (m, J=8.80 Hz, 2H) 7.48 (s, 1H).

$^{13}$C NMR (151 MHz, CHLOROFORM-d) δ ppm 10.23, 18.30, 21.75, 28.46, 29.39, 29.70, 30.30, 30.79, 31.52, 32.86, 33.81, 34.89, 36.21, 37.99, 39.28, 40.96, 42.96, 44.43, 45.12, 55.48, 114.21, 117.18, 117.82, 119.38, 121.99, 127.34, 130.98, 134.06, 146.06, 156.41, 164.80, 170.23, 175.88, 178.42.

EXAMPLE 28. PREPARATION OF COMPOUND XS0394

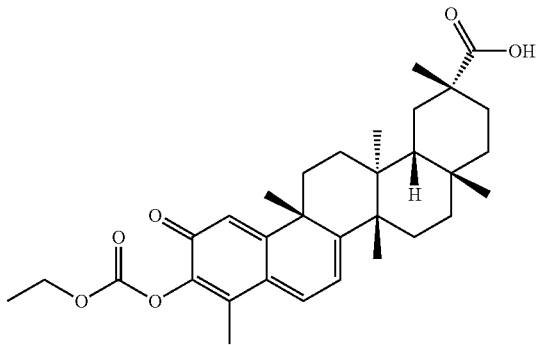

Compound YXY101 (50 mg, 0.11 mmol) and triethylamine (37 μL) were dissolved in re-distilled tetrahydrofuran (3.0 mL, 0.26 mmol) under stirring, then cooled to −30° C. Ethyl chloroformate (22 μL, 0.23 mmol) was added dropwise to the reaction liquor 10 minutes later. After being conducted at −30° C. for 12 hours under stirring, the reaction was stopped. The insoluble material was filtered off by a Buchner funnel with a fritted glass disc and washed with tetrahydrofuran to give a yellow filtrate. The yellow filtrate was added with 10 mL of pure water, and extracted with ethyl acetate three times (15 mL each time). The organic layer was combined, washed three times with saturated brine (30 mL each time), and dried over anhydrous sodium sulfate. The organic solvent was removed by distillation under reduced pressure to give a crude product as oily mixture. The product as yellow solid was obtained by column chromatography separation with n-hexane and ethyl acetate (hexane/ethyl acetate=10:1) as eluent, and using 300-400 mesh silica gel packed column.

$^1$H NMR (600 MHz, DMSO-d$_6$) δ ppm 1.05-1.07 (m, 1H) 1.08 (s, 3H) 1.09-1.12 (m, 1H) 1.18 (s, 3H) 1.23 (s, 3H) 1.27 (t, J=7.06 Hz, 3H) 1.28-1.31 (m, 1H) 1.41 (s, 3H) 1.43-1.50 (m, 4H) 1.53 (dd, J=12.10, 5.69 Hz, 1H) 1.59 (d, J=7.89 Hz, 1H) 1.65 (d, J=10.64 Hz, 2H) 1.70-1.78 (m, 2H) 1.79-1.85 (m, 1H) 1.90 (td, J=13.98, 3.39 Hz, 1 H) 1.95-2.01 (m, 1H) 2.01-2.06 (m, 1H) 2.15 (s, 3H) 2.26 (d, J=15.22 Hz, 1H) 4.21 (q, J=1.00 Hz, 2H) 6.30 (d, J=7.15 Hz, 1H) 6.40 (d, J=0.73 Hz, 1H) 7.29 (dd, J=7.52, 0.73 Hz, 1H) 12.07 (br. s, 1H).

$^{13}$C NMR (151 MHz, CHLOROFORM-d) □ ppm 11.17, 14.09, 19.00, 21.96, 28.60, 29.35, 29.36, 30.47, 30.67, 31.49, 32.67, 33.38, 34.53, 36.20, 38.24, 39.13, 40.16, 42.88, 44.05, 45.34, 65.05, 117.76, 117.78, 122.70, 126.08, 133.37, 142.54, 152.62, 163.30, 172.96, 183.86, 183.90.

EXAMPLE 29. PREPARATION OF COMPOUND XS0418

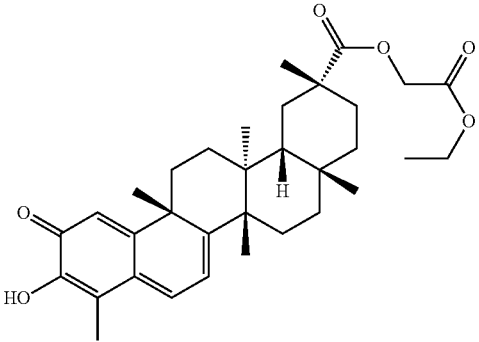

First, compound YXY101 (50 mg, 0.11 mmol) was stirred and dissolved in 2 mL of tetrahydrofuran, followed by an addition of potassium carbonate (15.2 mg, 0.11 mmol). Ethyl bromoacetate (18.37 mg, 0.11 mmol) was dissolved in 1 mL of tetrahydrofuran, and then added dropwise to the reaction solution. The reaction was carried out under stirring at room temperature for 4 hours, then quenched with 1 mol/L HCl (1 mL), 9 mL of pure water was added. The resulting mixture was extracted three times with ethyl acetate (15 mL each time). The collected organic layer was dried over anhydrous sodium sulfate, and the organic solvent ethyl acetate was removed by distillation in vacuo to afford a crude product as orange-red mixture solid. The product as orange-red solid was obtained by column chromatography separation with n-hexane and ethyl acetate (hexane/ethyl acetate=10:1) as eluent, using 300-400 mesh silica gel packed column.

$^1$H NMR (600 MHz, CHLOROFORM-d) □ ppm 0.53 (s, 3H) 0.99 (d, J=14.31 Hz, 1H) 1.11 (s, 3H) 1.25 (t, J=7.20 Hz, 3H) 1.27 (s, 3H) 1.28 (s, 3H) 1.39-1.44 (m, 1H) 1.45 (s, 3H) 1.51 (dd, J=14.95, 4.13 Hz, 1H) 1.54-1.58 (m, 1H) 1.60 (d, J=7.89 Hz, 1H) 1.63-1.67 (m, 1H) 1.67-1.71 (m, 1H) 1.75 (dd, J=15.96, 8.07 Hz, 1H) 1.80-1.82 (m, 1H) 1.83-1.85 (m, 1H) 1.85-1.92 (m, 1H) 2.06 (td, J=14.12, 3.85 Hz, 1H) 2.13-2.18 (m, 1H) 2.21 (s, 3H) 2.25 (d, J=14.31 Hz, 1H) 2.48 (d, J=15.96 Hz, 1H) 4.19 (q, J=7.15 Hz, 2H) 4.41 (d, J=15.77 Hz, 1H) 4.54 (d, J=15.96 Hz, 1H) 6.35 (d, J=7.15 Hz, 1H) 6.53 (d, J=1.10 Hz, 1H) 7.02 (dd, J=7.06, 1.19 Hz, 1H)

$^{13}$C NMR (151 MHz, CHLOROFORM-d) □ ppm 10.23, 14.04, 18.57, 21.61, 28.59, 29.57, 29.74, 30.47, 30.63, 31.55, 32.56, 33.50, 34.67, 36.31, 38.24, 39.39, 40.40, 42.91, 44.19, 45.01, 60.52, 61.28, 117.15, 118.13, 119.52, 127.37, 134.09, 145.98, 164.74, 167.70, 170.03, 177.53, 178.31

EXAMPLE 30. PREPARATION OF COMPOUNDS XS0421, XS0457, XS0473 AND XS0493

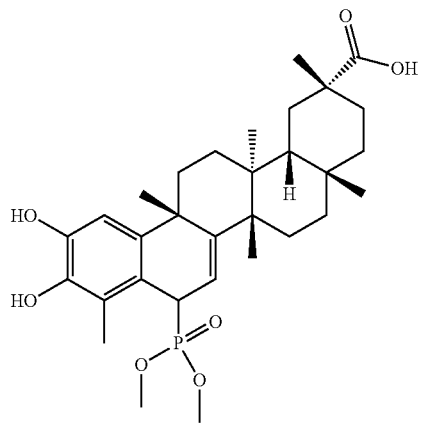

XS0421

Taking the synthesis of XS0421 as an example: Compound YXY101 (50 mg, 0.11 mmol) was weighed in a 50 ml sealed tube, then dimethyl phosphite (123 mg, 1.1 mmol) and 2.7 mg of aluminum chloride hexahydrate (0.1 eq) were added, and 2 mL of DCM was added for dissolution. The tube was sealed, and the reaction was performed at room temperature for 6 h. The reaction was stopped and quenched with saturated NaCl. The resulting mixture was extracted with ethyl acetate three times, the organic phases were combined and dried with anhydrous $Na_2SO_4$, and concentrated under reduced pressure to remove the solvent. The residue was purified by silica gel column chromatography with ethyl acetate:n-hexane=1:2 to gave a white solid, yield 55%.

$^1$H NMR (600 MHz, DMSO-$d_6$) □ ppm 0.61 (3H, s) 0.86 (1H, d, J=12.84 Hz) 1.06 (3H, s) 1.10 (3H, s) 1.19 (3H, s) 1.22-1.27 (1H, m) 1.27-1.32 (1H, m) 1.40 (1H, d, J=4.95 Hz) 1.43 (1H, d, J=5.32 Hz) 1.49 (1H, d, J=8.07 Hz) 1.51-1.55 (1H, m) 1.57 (3H, s) 1.59-1.60 (1H, m) 1.60-1.64 (1H, m) 1.76-1.85 (1H, m) 1.93-1.97 (1H, m) 1.99 (1H, d, J=2.20 Hz) 2.00-2.02 (1H, m) 2.02-2.06 (1H, m) 2.13 (3H, s) 2.32 (1H, d, J=15.59 Hz) 3.49 (3H, d, J=8.80 Hz) 3.51 (3H, d, J=8.99 Hz) 4.19 (1H, dd, J=23.66, 6.24 Hz) 5.64 (1H, dd, J=6.33, 3.21 Hz) 6.66 (1H, s) 7.97 (1H, s) 9.04 (1H, br. s.) 12.04 (1H, s).

$^{13}$C NMR (151 MHz, DMSO-$d_6$) □ ppm 12.60, 14.00 (1 C, s) 18.04, 21.58 (1 C, d, J=6.60 Hz) 22.11, 28.78, 29.48, 30.02 (1 C, d, J=13.20 Hz) 30.18, 31.00, 31.45, 32.42, 33.49, 33.57, 34.57, 36.42, 37.43, 37.89, 38.79, 43.88, 52.31 (1 C, d, J=6.60 Hz) 52.81 (1 C, d, J=6.60 Hz) 109.32, 114.64 (1 C, d, J=12.10 Hz) 117.90 (1 C, d, J=7.70 Hz) 121.35 (1 C, d, J=4.40 Hz) 140.50 (1 C, d, J=6.60 Hz) 141.05 (1 C, d, J=3.30 Hz) 144.08 (1 C, d, J=3.30 Hz) 150.62 (1 C, d, J=12.10 Hz) 179.51.

According to the above preparation method, the following compounds were also synthesized in the present invention:

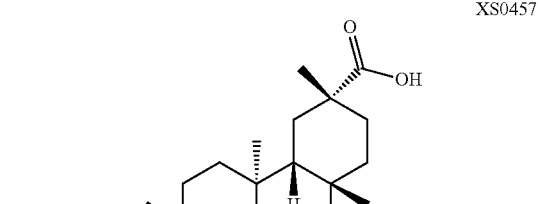

XS0457

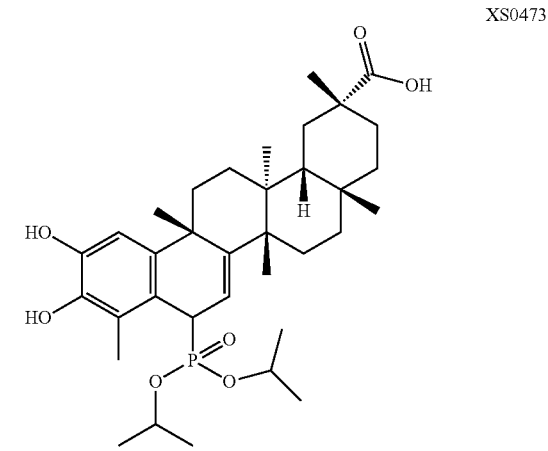

XS0473

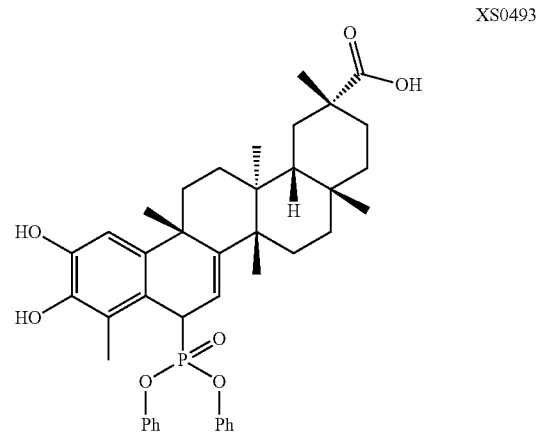

XS0493

EXAMPLE 31. PREPARATION OF COMPOUNDS XS0439, XS0442, XS0444-XS0449, XS0478-XS0480, XS0487 AND XS0490
XS0439
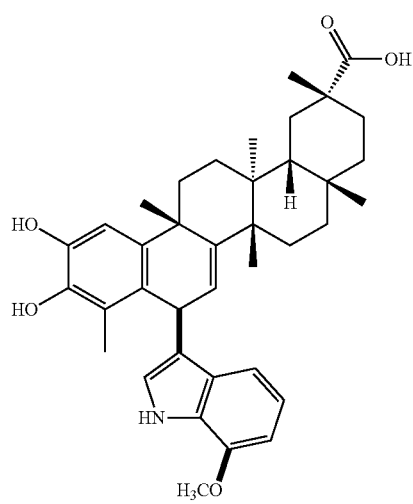
XS0442
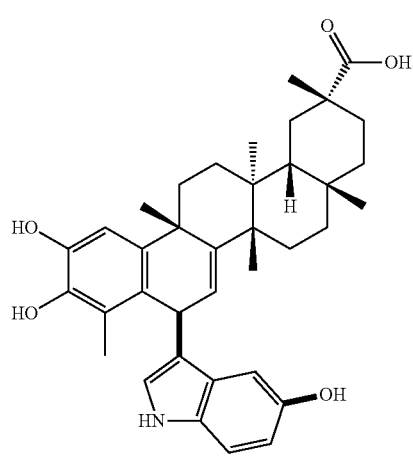
XS0444
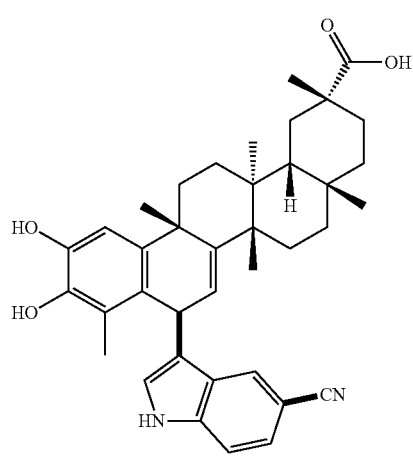
XS0445
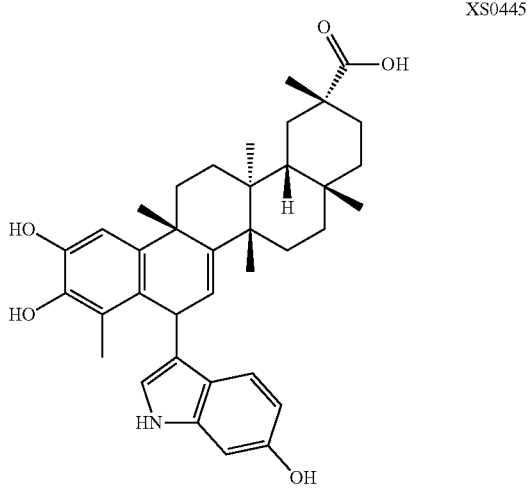
XS0446
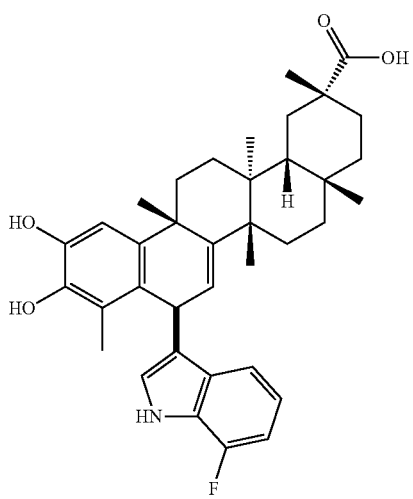
XS0447
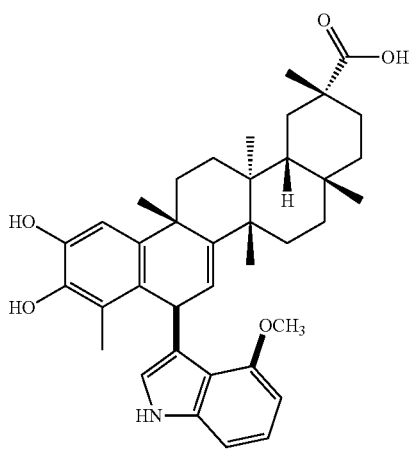

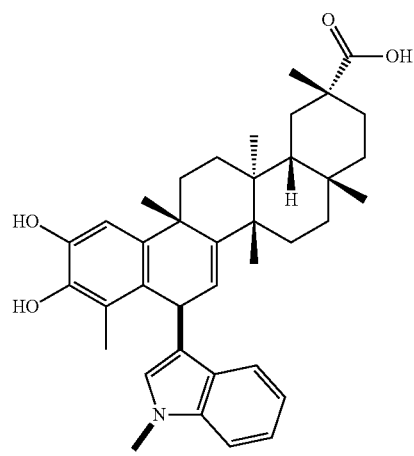
XS0448
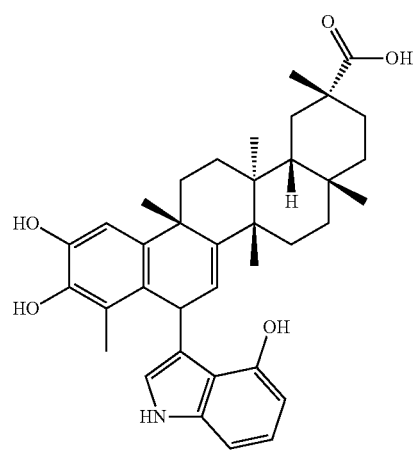
XS0479
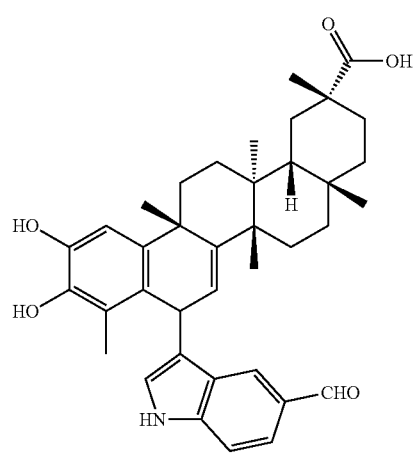
XS0449
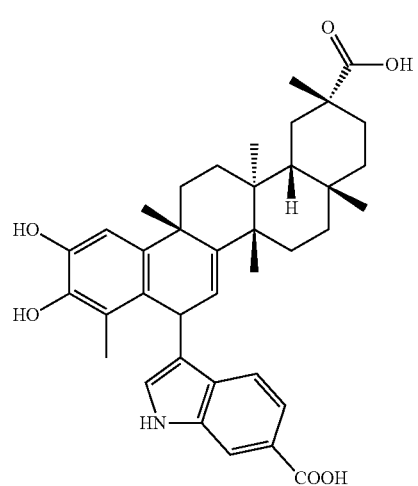
XS0480
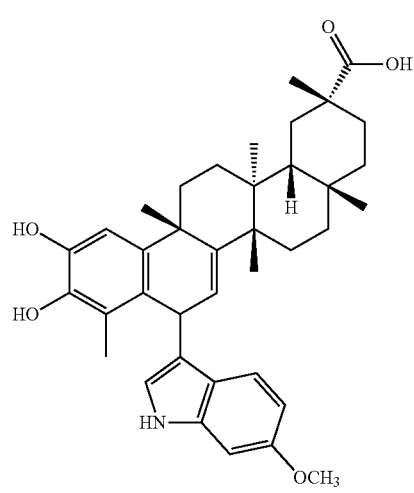
XS0478
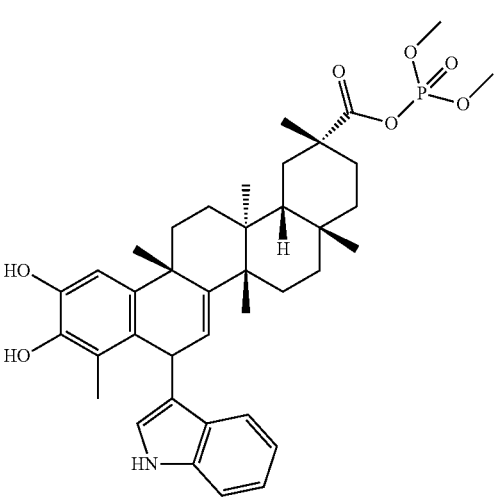
XS0487

XS0490

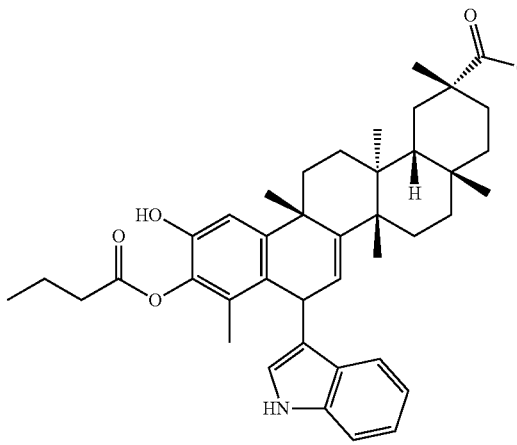

XS0491

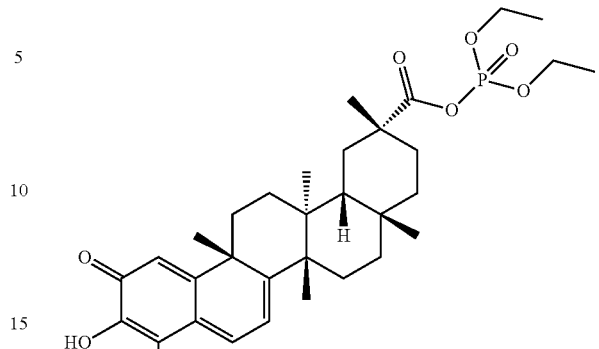

XS0492

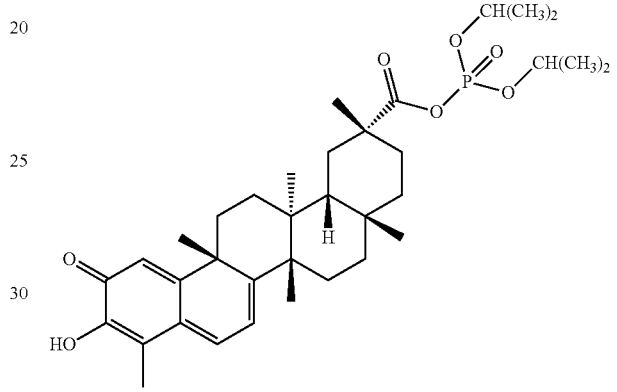

The preparation method is exemplified by XS0439: Compound YXY101 (100 mg, 0.22 mmol) was dissolved in dichloromethane (4 mL) under stirring. 7-Methoxy-substituted indole (65.3 mg, 0.44 mmol) was added, then aluminum trichloride hexahydrate (5.3 mg, 0.022 mmol). The reaction was carried out under stirring at room temperature for 5 hours. The reaction was stopped, the reaction mixture was added with deionized water (15 mL) and extracted three times with ethyl acetate. The ethyl acetate layers were combined, washed with saturated NaCL three times, dried over anhydrous $Na_2SO_4$, concentrated by a rotary evaporator to obtain a crude product (brown oily matter). The crude product was separated and purified by rapid column chromatography (ethyl acetate:n-hexane=1:4), dried in vacuo to afford a product as purple red solid.

$^1$H-NMR (DMSO-$d_6$) δ ppm 0.71 (s, 3H), 0.86 (d, J=9.9 Hz, 1H), 0.96 (s, 3H), 1.01 (s, 3H), 1.10 (s, 3H), 1.22-1.29 (m, 2H), 1.32 (s, 3H), 1.34-1.40 (m, 2H), 1.45 (d, J=8.1 Hz, 1H), 1.50-1.61 (m, 3H), 1.62-1.75 (m, 2H), 1.79 (s, 3H), 1.96-2.08 (m, 3H), 2.34 (d, J=15.4 Hz, 1H), 3.88 (s, 3H), 4.79 (d, J=5.9 Hz, 1H), 6.12 (d, J=6.2 Hz, 1H), 6.18 (s, 1H), 6.62 (d, J=7.7 Hz, 1H), 6.73 (s, 1H), 6.90 (t, J=7.9 Hz, 1H), 7.22 (d, J=7.9 Hz, 1H), 7.88 (br. s., 1H), 8.99 (br. s., 1H), 10.69 (s, 1H), 12.04 (br. s., 1H).

$^{13}$C-NMR (DMSO-$d_6$) δ ppm 11.9, 18.5, 22.3, 29.1, 29.9, 30.4, 30.5, 30.6, 31.8, 32.9, 34.9, 35.4, 35.5, 35.6, 36.8, 36.9, 37.8, 43.5, 44.3, 55.4, 101.8, 108.8, 112.2, 119.2, 119.8, 121.1, 121.6, 122.6, 126.3, 126.7, 128.5, 140.8, 141.4, 144.0, 146.6, 147.0, 180.0.

EXAMPLE 32. PREPARATION OF COMPOUNDS XS0486, XS0491 AND XS0492

XS0486

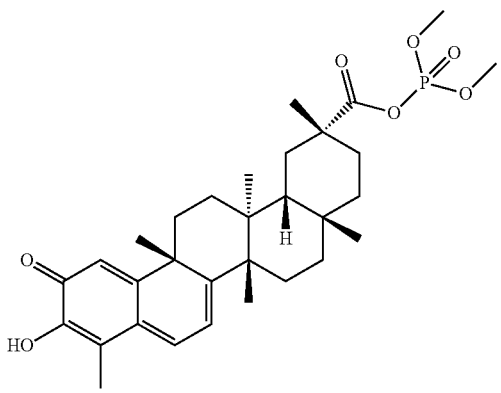

Taking the preparation of compound XS0486 as an example: First, Compound YXY101 (50 mg, 0.11 mmol) was dissolved in dioxane (600 μL), triethylamine (150 μL, 0.33 mmol) was added, and then dioxane (100 μL) was added to wash the residue on the wall of the reaction bottle, and the reaction solution was cooled to 0° C. Dimethyl phosphite (110 mg, 1.1 mmol) was dissolved in 50 μL of carbon tetrachloride, then the dissolved dimethyl phosphite was slowly added dropwise into the reaction solution dissolved with Celastrol, the reaction was carried out under stirring at 0° C. for 12 h, then 10 mL of ice-cold deionized water was added, and 10 mL of saturated ammonium chloride solution was added for quenching the reaction. The resulting mixture was extracted with ethyl acetate three times (15 mL each time), and the organic layer was collected and dried over anhydrous sodium sulfate. The organic solvent ethyl acetate was then removed by distillation under reduced pressure to give a crude product as red mixture solid. The crude product was separated by rapid column chromatography with 300-400 mesh silica gel packed column using n-hexane and ethyl acetate (hexane/ethyl acetate=1:1) as eluent to give a red solid product.

$^1$H NMR (600 MHz, DMSO-$d_6$) δ ppm 0.60 (s, 3H) 0.96 (d, J=13.57 Hz, 1H) 1.08 (s, 3H) 1.23 (s, 3H) 1.24 (s, 3H) 1.38 (s, 3H) 1.41-1.48 (m, 2H) 1.55-1.60 (m, 3H) 1.61-1.67 (m, 2H) 1.69-1.74 (m, 1H) 1.78 (dd, J=16.14, 7.89 Hz, 1H) 1.81-1.88 (m, 1H) 1.95 (td, J=14.12, 3.85 Hz, 1H) 2.02 (d, J=13.94 Hz, 1H) 2.09 (s, 3H) 2.21-2.24 (m, 1H) 2.27 (d, J=15.96 Hz, 1H) 3.74 (dd, J=11.55, 5.14 Hz, 6H) 6.36 (d, J=7.15 Hz, 1H) 6.39 (d, J=1.28 Hz, 1H) 7.08 (dd, J=6.97, 1.10 Hz, 1H) 8.75 (s, 1H).

$^{13}$C NMR (151 MHz, DMSO-d$_6$) δ ppm 10.07, 18.53, 21.43, 28.03, 29.09, 29.24, 29.71, 30.07, 31.21, 31.46, 32.76, 33.92, 35.85, 37.71, 38.78, 41.23 (d, J=5.50 Hz,) 41.97, 43.37, 44.45, 55.15 (dd, J=17.61, 5.50 Hz, 2 C) 117.24, 118.13, 120.12, 126.89, 133.12, 146.44, 162.82, 167.43, 172.21 (d, J=11.00 Hz) 177.98.

EXAMPLE 33. PREPARATION OF COMPOUND XS0488

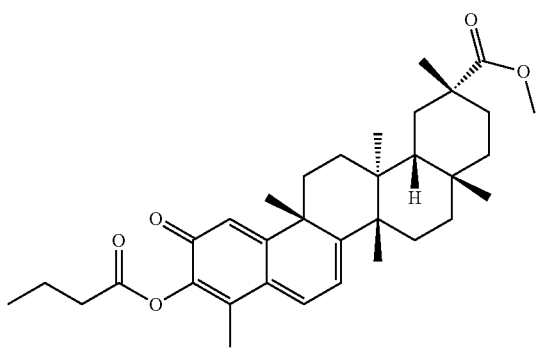

First, compound XS0077 (80 mg, 0.17 mmol) was dissolved in tetrahydrofuran (4 mL), triethylamine (370 μL, 2.5 mmol) was added, then 4-DMAP (24.7 mg, 0.22 mmol) was added, stirred evenly, and n-butyryl chloride (113 μL, 1.1 mmol) was added. The reaction was carried out under stirring at room temperature for 30 min, then quenched with 10 mL of saturated ammonium chloride solution. The resulting mixture was extracted with ethyl acetate three times (15 mL each time). The organic layer was collected and dried over anhydrous sodium sulfate, the organic solvent ethyl acetate was removed by distillation under reduced pressure to give a crude product as red mixture solid. Separation was performed by column chromatography with 300-400 mesh silica gel packed column, using n-hexane and ethyl acetate (hexane/ethyl acetate=4:1) as eluent to give a product as bright yellow solid.

$^1$H NMR (600 MHz, DMSO-d$_6$) ppm 0.46-0.51 (m, 3H) 0.91 (d, J=1.00 Hz, 1H) 0.95-1.01 (m, 3H) 1.08 (s, 3H) 1.12 (s, 3H) 1.23 (s, 3H) 1.36 (ddd, J=13.80, 4.20 Hz, 1H) 1.42 (s, 3H) 1.44-1.48 (m, 1H) 1.54-1.60 (m, 3H) 1.63 (s, 2H) 1.66-1.68 (m, 2H) 1.70 (d, J=9.17 Hz, 2H) 1.83 (dd, J=13.57, 7.70 Hz, 1H) 1.93-1.99 (m, 1H) 2.06 (d, J=13.94 Hz, 1H) 2.10 (s, 3H) 2.22 (d, J=7.34 Hz, 1H) 2.32 (d, J=15.59 Hz, 1H) 2.55 (t, J=7.15 Hz, 2H) 3.49 (s, 3H) 6.38 (s, 1H) 6.41 (d, J=7.15 Hz, 1H) 7.31 (d, J=6.97 Hz, 1H).

$^{13}$C NMR (151 MHz, DMSO-d$_6$) δ ppm 13.41, 18.05, 21.59, 28.06, 29.11, 29.42, 30.11, 30.16, 30.32, 31.32, 32.21, 32.31, 33.06, 34.36, 34.91, 36.00, 37.90, 38.77, 39.83, 42.22, 43.64, 44.85, 51.48, 117.99, 122.13, 125.21, 133.52, 136.69, 142.26, 162.81, 170.65, 171.21, 176.21, 177.91.

EXAMPLE 34. PREPARATION OF COMPOUND XS0506

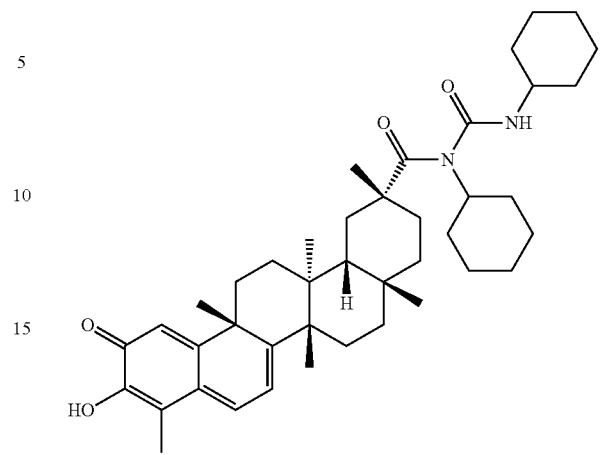

Compound YXY101 (50 mg, 0.11 mmol) was weighed in a 50 ml round bottom flask, dicyclohexylcarbodiimide (23 mg, 0.11 mmol) and glucose (24 mg, 0.11 mmol) were added, then 2 ml of DCM was added for dissolution. The reaction was carried out at room temperature for 12 h, quenched with a large amount of water, extracted with ethyl acetate three times. The organic phases were combined and dried over anhydrous Na$_2$SO$_4$, and concentrated under reduced pressure to remove solvent. Separation and purification were performed by silica gel column with ethyl acetate:n-hexane=1:4 to afford an orange-red solid, yield 42%.

$^1$H NMR (600 MHz, DMSO-d$_6$) δ ppm 0.57 (s, 3H) 1.07 (s, 3H) 1.12-1.14 (m, 1H) 1.14-1.16 (m, 1H) 1.17 (s, 3H) 1.21 (s, 3H) 1.22-1.23 (m, 2H) 1.24-1.28 (m, 4H) 1.28-1.32 (m, 2H) 1.38 (s, 3H) 1.40-1.46 (m, 2H) 1.47-1.52 (m, 2H) 1.57 (d, J=6.79 Hz, 1H) 1.59-1.63 (m, 4H) 1.64-1.72 (m, 6H) 1.75-1.83 (m, 4H) 1.92-1.96 (m, 1H) 1.97-2.01 (m, 1H) 2.03-2.07 (m, 1H) 2.09 (s, 3H) 2.18 (d, J=10.82 Hz, 2H) 2.73 (d, J=15.04 Hz, 1H) 3.40-3.49 (m, 1H) 3.80-3.89 (m, 1H) 6.36 (d, J=7.34 Hz, 1H) 6.40 (d, J=0.92 Hz, 1H) 7.07 (dd, J=6.97, 0.92 Hz, 1H) 7.73 (d, J=8.07 Hz, 1H) 8.71 (s, 1H).

$^{13}$C NMR (151 MHz, DMSO-d$_6$) δ ppm 10.08, 18.32, 21.83, 24.68, 24.75, 25.13, 25.29, 25.63, 25.67, 28.38, 28.59, 29.91, 30.13, 31.02, 31.08, 31.39, 31.82, 31.91, 31.93, 32.36, 33.10, 36.02, 36.13, 37.67, 38.99, 42.16, 42.81, 44.45, 44.49, 50.05, 54.77, 117.23, 117.93, 120.04, 126.75, 133.25, 146.43, 153.97, 163.09, 168.74, 175.44, 177.83.

EXAMPLE 35. PREPARATION OF COMPOUND XS0507

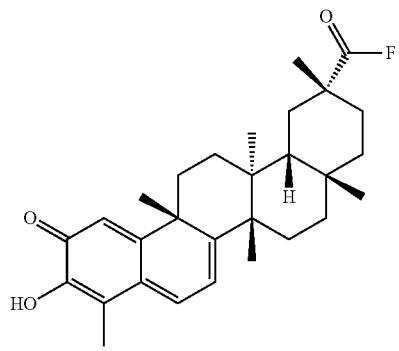

Compound YXY101 (50 mg, 0.11 mmol) was weighed in a 50 ml round bottom flask, added with 2 ml of DCM for dissolution, then transferred to −78° C. and stirred. DAST (150 ul, 10 eq) was added and reacted at −78° C. for 1 h. The reaction solution was directly poured into a large amount of ice to quench the reaction. The aqueous phase was extracted three times with DCM. The organic phases were combined and dried over anhydrous $Na_2SO_4$. The organic phase was concentrated under reduced pressure to remove solvent. Separation and purification were performed by column chromatography with ethyl acetate:n-hexane=1:4 system to gave an orange-red solid, yield 58%.

$^1$H NMR (600 MHz, DMSO-$d_6$) δ ppm 0.56 (s, 3H) 0.98 (d, J=11.92 Hz, 1H) 1.08 (s, 3H) 1.22 (s, 3H) 1.29 (s, 3H) 1.38 (s, 3H) 1.43-1.47 (m, 1H) 1.48-1.52 (m, 1H) 1.55-1.59 (m, 2H) 1.60-1.64 (m, 1H) 1.67 (d, J=4.03 Hz, 1H) 1.71 (d, J=3.85 Hz, 1H) 1.80 (dd, J=16.41, 8.16 Hz, 1H) 1.83-1.87 (m, 1H) 1.88-1.92 (m, 1H) 1.96 (d, J=17.61 Hz, 1H) 1.95-1.95 (m, 1H) 2.09 (s, 3H) 2.20 (d, J=1.83 Hz, 2H) 6.35 (d, J=7.34 Hz, 1H) 6.38 (d, J=1.28 Hz, 1H) 7.06 (dd, J=6.97, 1.28 Hz, 1H) 8.73 (s, 1H).

$^{13}$C NMR (151 MHz, DMSO-$d_6$) δ ppm 10.07, 18.85, 21.41, 27.89, 29.26, 29.33, 29.46, 29.94, 31.16, 32.71, 33.79, 35.78, 37.87, 38.74, 40.04, 40.22, 41.89, 43.26, 44.33, 117.21, 118.14, 120.15, 126.99, 132.88, 146.41, 162.78, 167.39 (d, J=418.15 Hz, 1 C), 166.71, 177.97.

EXAMPLE 36. PREPARATION OF COMPOUND XS0509

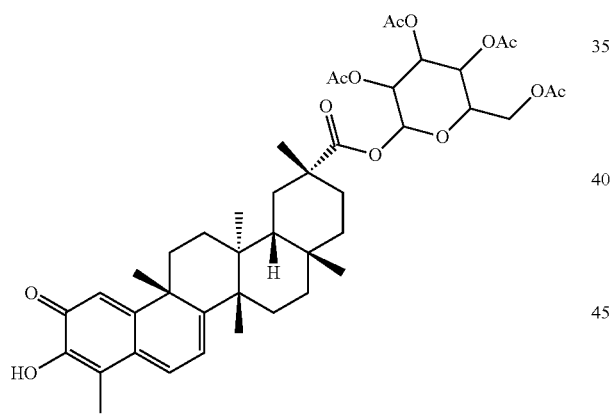

Compound YXY101 (50 mg, 0.11 mmol) was weighed in a 25 ml heavy wall pressure vessel, added with tetrabutylammonium bromide (TBAB, 17.5 mg, 0.05 mmol), and 2 ml of dichloromethane (DCM) was added for dissolution, and then 5% NaOH (180 μl) was add dropwise. The reaction was carried out at room temperature for 30 min, then transferred to 50° C. oil bath, and added dropwise with dichloromethane solution of 2,3,4,6-tetraacetoxy-α-D-glucopyranose bromide (57 mg-1 ml, 0.138 mmol), and reacted at 50° C. for 12 h. The reaction was stopped, and a large amount of water and saturated brine were added. The resulting mixture was extracted with DCM for 3 times. The organic phases were combined and dried over anhydrous $Na_2SO_4$. The organic phase was concentrated under reduced pressure, and purified by silica gel column chromatography with ethyl acetate:n-hexane=4:1 system to obtain a yellow solid, yield 25%.

$^1$H NMR (600 MHz, DMSO-$d_6$) δ ppm 0.51 (s, 3H) 0.95 (d, J=13.57 Hz, 1H) 1.08 (d, J=6.24 Hz, 6H) 1.22 (s, 3H) 1.23 (br. s., 1H) 1.38 (s, 3H) 1.41 (d, J=4.22 Hz, 1H) 1.46 (d, J=11.92 Hz, 1H) 1.56 (d, J=7.52 Hz, 2H) 1.58 (s, 3H) 1.60-1.63 (m, 1H) 1.64 (d, J=4.95 Hz, 2H) 1.66-1.69 (m, 1H) 1.81-1.87 (m, 1H) 1.91 (s, 3H) 1.94 (d, J=3.67 Hz, 1H) 1.97 (s, 3H) 2.00-2.04 (m, 1H) 2.08 (s, 3H) 2.12 (s, 3H) 2.19 (d, J=8.80 Hz, 1H) 2.31 (d, J=15.59 Hz, 1H) 3.85-3.90 (m, 1H) 3.92-3.96 (m, 1H) 4.30 (dd, J=8.16, 4.13 Hz, 1H) 5.05 (dd, J=10.09, 8.44 Hz, 1H) 5.23 (d, J=3.48 Hz, 1H) 5.29 (dd, J=10.45, 3.67 Hz, 1H) 5.83 (d, J=8.25 Hz, 1H) 6.36 (d, J=7.15 Hz, 1H) 6.37 (d, J=0.92 Hz, 1H) 7.06 (d, J=6.97 Hz, 1H) 8.71 (s, 1H).

$^{13}$C NMR (151 MHz, DMSO-$d_6$) δ ppm 10.06, 18.63, 19.97, 20.31, 20.42, 21.57, 28.11, 28.59, 29.22, 29.97, 30.07, 31.31, 32.62, 32.84, 34.57, 35.93, 37.76, 38.52, 40.05, 40.24, 41.97, 43.46, 44.54, 61.76, 67.35, 67.85, 69.78, 71.21, 91.64, 117.29, 118.08, 120.11, 126.93, 133.07, 146.36, 162.86, 167.78, 169.24, 169.41, 169.57, 169.97, 176.51, 177.93.

EXAMPLE 37. PREPARATION OF COMPOUND XS0514, XS0515

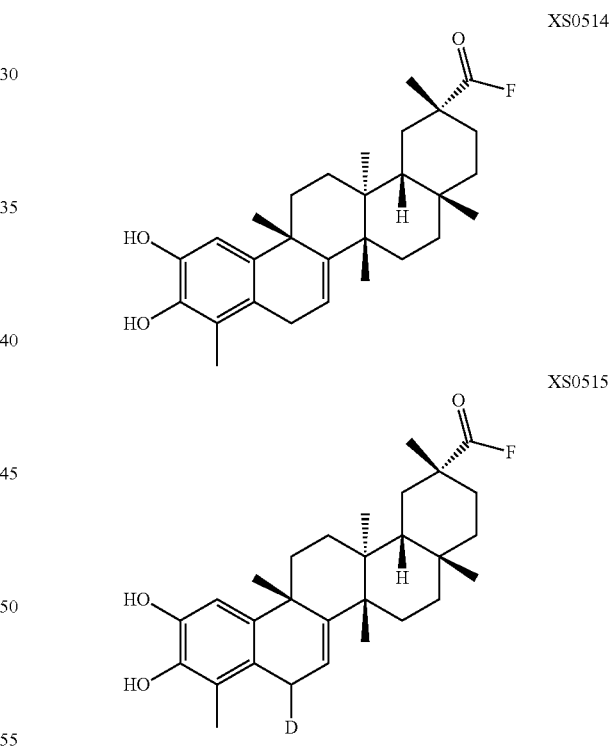

Taking the synthesis of XS0514 as an example: XS0419 (50 mg, 0.11 mmol) was weighed in a 50 ml round bottom flask, added with 2 ml DCM for dissolution, then transferred to −78° C. and stirred, followed by an addition of diethylaminosulfurtrifluoride (DAST, 150 ul, 10 eq), and reacted at −78° C. for 1 h. The reaction solution was poured into a large amount of ice to quench the reaction. The aqueous phase was extracted three times with DCM. The organic phase was combined, washed with saturated $NaHCO_3$, dried with anhydrous $Na_2SO_4$, and concentrated under reduced pressure. Separation and purification were performed by silica gel column chromatography with ethyl acetate:n-hexane=1:8 system to give an orange-red solid, yield 58%.

$^1$H NMR (600 MHz, DMSO-d$_6$) δ ppm 0.61 (s, 3H) 0.95 (d, J=14.49 Hz, 1H) 1.06 (s, 3H) 1.18 (s, 3H) 1.23 (s, 3H) 1.28 (s, 3H) 1.41 (d, J=14.86 Hz, 2H) 1.47 (dd, J=13.85, 4.31 Hz, 2H) 1.54 (d, J=7.70 Hz, 1H) 1.58-1.63 (m, 2H) 1.74-1.84 (m, 2H) 1.88 (d, J=6.05 Hz, 1H) 1.94 (d, J=10.64 Hz, 1H) 1.98 (d, J=10.09 Hz, 1H) 2.01 (s, 3H) 2.07 (d, J=17.97 Hz, 1H) 2.24 (d, J=15.96 Hz, 1H) 2.89-2.94 (m, 1H) 3.16-3.21 (m, 1H) 5.74 (d, J=4.77 Hz, 1H) 6.61 (s, 1H) 7.81 (br. s., 1H) 8.78 (br. s., 1H).

$^{13}$C NMR (151 MHz, DMSO-d$_6$) δ ppm 11.56, 18.66, 22.57, 27.30, 28.27, 29.21, 29.54, 29.98, 30.02, 30.08, 31.18, 33.69, 33.99, 34.13, 36.05, 36.27, 37.14, 40.25, 43.12, 43.42, 108.21, 118.07, 120.13, 123.02, 139.23, 140.61, 143.17, 148.76, 167.64 (d, J=380.73 Hz, 1 C).

EXAMPLE 38. PREPARATION OF COMPOUND XS0516

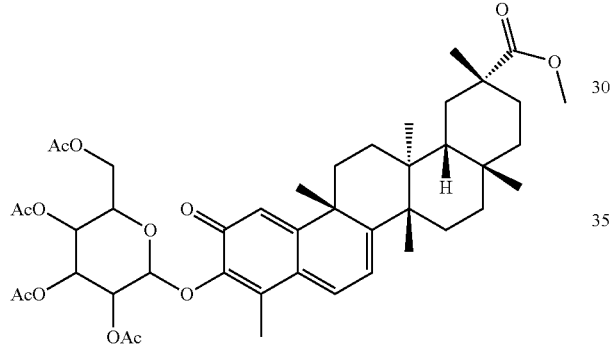

XS0077 (50 mg, 0.11 mmol) was weighed in a 25 ml heavy wall pressure vessel, added with tetrabutylammonium bromide (TBAB, 17.5 mg, 0.05 mmol), and 2 ml of dichloromethane (DCM) was added for dissolution, then 5% NaOH (180 μL) was added dropwise. The mixture were reacted at room temperature for 30 min, subsequently transferred to 50° C. oil bath, added dropwise with 2,3,4,6-tetraacetoxy-α-D-glucopyranose bromide-dichloromethane solution (57 mg-1 ml, 0.138 mmol) and reacted at 50° C. for 12 h. The reaction was stopped, a large amount of water and saturated brine were added, and the mixture was extracted with DCM for 3 times. The organic phases were combined, dried over anhydrous Na$_2$SO$_4$ concentrated under reduced pressure, and purified by silica gel column chromatography with ethyl acetate:n-hexane=4:1 to afford a yellow solid, yield 25%.

$^1$H NMR (600 MHz, CHLOROFORM-d) δ ppm 0.53 (s, 3H) 0.97 (d, J=14.31 Hz, 1H) 1.10 (s, 3H) 1.18 (s, 3H) 1.26 (s, 3H) 1.38 (td, J=14.03, 4.58 Hz, 1H) 1.47 (s, 3H) 1.50 (dd, J=15.59, 4.58 Hz, 1H) 1.53-1.56 (m, 1H) 1.58 (d, J=8.25 Hz, 1H) 1.62-1.65 (m, 2H) 1.66 (d, J=5.32 Hz, 1H) 1.67-1.72 (m, 2H) 1.76-1.80 (m, 1H) 1.82-1.87 (m, 1H) 1.87-1.91 (m, 1H) 1.98 (s, 3H) 2.01 (s, 3H) 2.10-2.14 (m, 1H) 2.15 (s, 3H) 2.18 (s, 3H) 2.23 (s, 3H) 2.42 (d, J=15.77 Hz, 1H) 3.55 (s, 3H) 3.86 (t, J=7.34 Hz, 1H) 4.06 (dd, J=11.10, 7.61 Hz, 1H) 4.16 (dd, J=11.10, 6.14 Hz, 1H) 5.11 (dd, J=10.36, 3.58 Hz, 1H) 5.31 (d, J=7.89 Hz, 1H) 5.38-5.43 (m, 2H) 6.31 (d, J=7.15 Hz, 1H) 6.39 (d, J=1.10 Hz, 1H) 7.02 (dd, J=7.06, 1.01 Hz, 1H).

$^{13}$C NMR (151 MHz, CHLOROFORM-d) δ ppm 11.54, 18.33, 20.61, 20.70, 21.02, 21.86, 28.57, 29.57, 29.85, 30.52, 30.82, 31.55, 32.65, 33.67, 34.70, 36.34, 38.20, 39.24, 40.37, 42.30, 44.27, 45.07, 51.54, 60.81, 66.90, 69.09, 70.49, 70.84, 100.37, 117.93, 123.33, 126.92, 134.32, 134.96, 145.71, 162.50, 170.07, 170.33, 170.35, 170.37, 170.61, 178.68, 179.14.

EXAMPLE 39. PREPARATION OF COMPOUND XS0534

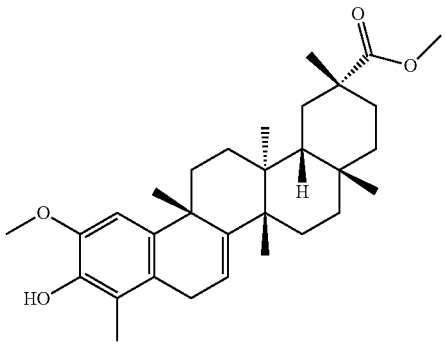

XS0077 (150 mg, 0.32 mmol) was weighed and dissolved in 4 mL of acetone with stirring, anhydrous potassium carbonate (180 mg, 1.3 mmol) and dimethyl sulfate (95 μL, 0.96 mmol) were added under stirring, the mixture was reacted under oil bath at 70° C. for 12 h. The reaction was quenched with 1 mol/L HCl, then adjusted to pH=7, and extracted with ethyl acetate three times. The organic phases were combined, dried over Na$_2$SO$_4$, concentrated to remove solvent under reduced pressure, and separated and purified by silica gel column chromatography with ethyl acetate:n-hexane=1:10 system to afford a white solid, yield 24.3%.

$^1$H NMR (600 MHz, DMSO-d$_6$) δ ppm 0.51 (s, 3H) 0.87-0.92 (m, 1H) 1.06 (s, 3H) 1.12 (s, 3H) 1.18 (s, 3H) 1.27 (s, 3H) 1.32-1.37 (m, 1H) 1.37-1.42 (m, 1H) 1.47-1.52 (m, 3H) 1.55-1.61 (m, 2H) 1.65 (dd, J=15.68, 8.16 Hz, 1H) 1.80 (td, J=13.43, 7.24 Hz, 1H) 1.84-1.90 (m, 1H) 1.97 (td, J=13.75, 4.03 Hz, 1H) 2.02 (s, 3H) 2.06 (d, J=13.57 Hz, 1H) 2.12-2.18 (m, 1H) 2.33 (d, J=15.77 Hz, 1H) 2.95 (dd, J=20.17, 1.40 Hz, 1H) 3.21 (dd, J=20.72, 6.24 Hz, 1H) 3.46-3.50 (m, 3H) 3.77 (s, 3H) 5.72 (dd, J=6.42, 1.28 Hz, 1H) 6.72 (s, 1H) 8.10 (s, 1H).

$^{13}$C NMR (151 MHz, DMSO-d$_6$) δ ppm 11.35, 17.69, 22.41, 27.31, 28.41, 29.42, 29.90, 30.13, 30.25, 31.36, 32.37, 34.01, 34.21, 34.36, 36.41, 36.49, 37.11, 39.85, 43.23, 43.80, 51.37, 55.82, 105.29, 117.48, 119.79, 124.58, 139.03, 141.52, 145.83, 148.73, 178.04.

EXAMPLE 41. PREPARATION OF COMPOUND XS0420

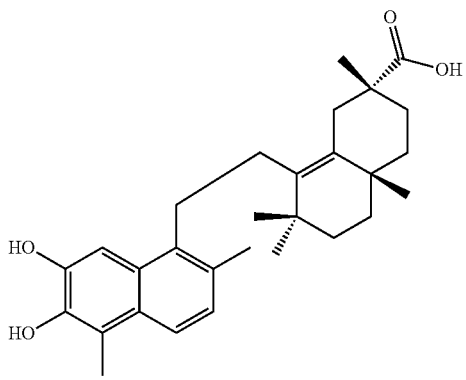

Compound YXY101 (50 mg, 0.11 mmol) was weighed in a 50 ml round bottom flask, PTSA (100 mg, excess) and 2 mL of toluene were added, and the mixture was stirred at room temperature for 6 h quenched by saturated NaHCO$_3$ solution, and extracted with ethyl acetate three times. The organic phases were combined, dried with anhydrous Na$_2$SO$_4$, concentrated under reduced pressure to remove solvent, and separated and purified by silica gel column chromatography with ethyl acetate:n-hexane=1:4 system to afford an off-white solid in 70% yield.

$^1$H NMR (600 MHz, DMSO-d$_6$) δ ppm 1.03 (s, 3H) 1.06 (s, 3H) 1.07-1.11 (m, 1H) 1.15 (s, 3H) 1.18 (s, 3H) 1.21-1.24 (m, 1H) 1.28-1.32 (m, 1H) 1.37 (td, J=13.75, 5.32 Hz, 1H) 1.46 (dd, J=8.62, 4.03 Hz, 2H) 1.48-1.50 (m, 2H) 1.51-1.55 (m, 1H) 1.58 (dd, J=12.93, 1.93 Hz, 1H) 1.83-1.90 (m, 3H) 2.33 (t, J=1.00 Hz, 1H) 2.36 (s, 3H) 2.38 (s, 3H) 2.80-2.92 (m, 2H) 2.80-2.92 (m, 2H) 7.06 (d, J=8.62 Hz, 1H) 7.18 (s, 1H) 7.49 (d, J=8.44 Hz, 1H) 8.48 (br. s., 1H) 9.92 (s, 1H).

$^{13}$C NMR (151 MHz, DMSO-d$_6$) δ ppm 10.96, 19.45, 21.73, 21.95, 23.51, 24.03, 25.45, 30.89, 30.96, 34.59, 35.08, 36.41, 37.98, 38.30, 40.71, 41.70, 43.50, 99.01, 102.91, 115.74, 120.73, 126.07, 127.17, 127.30, 129.03, 132.36, 143.60, 146.12, 175.68.

EXAMPLE 42. PREPARATION OF COMPOUND XS0502

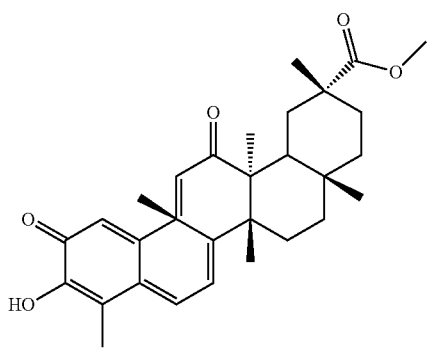

Compound XS0077 (50 mg, 0.11 mmol) was weighed in a 50 ml round bottom flask, SeO$_2$ (200 mg, excess) and 2 mL of dioxane were added, and the mixture was stirred at 55° C. for 12 hours. The reaction was quenched by the addition of deionized water, extracted with ethyl acetate for 3 times. The organic phases were dried over Na$_2$SO$_4$, concentrated to remove solvent under reduced pressure, and separated and purified by silica gel column chromatography with ethyl acetate:n-hexane=1:10 system to give an off-white solid, yield 16.8%.

$^1$H NMR (600 MHz, DMSO-d$_6$) δ ppm 0.75 (s, 3H) 0.93-0.97 (m, 1H) 1.10 (s, 3H) 1.21 (s, 3H) 1.22 (s, 3H) 1.40 (td, J=14.08, 4.13 Hz, 1H) 1.49 (dt, J=14.53, 4.65 Hz, 1H) 1.71-1.79 (m, 2H) 1.79-1.82 (m, 1H) 1.82-1.88 (m, 1H) 2.07-2.10 (m, 1H) 2.10-2.12 (m, 1H) 2.13 (s, 3H) 2.29 (d, J=14.31 Hz, 1H) 2.46 (t, J=4.77 Hz, 1H) 2.54 (s, 3H) 3.50 (s, 3H) 6.20 (d, J=9.54 Hz, 1H) 6.45 (d, J=9.54 Hz, 1H) 7.11 (s, 1H) 9.44 (s, 1H).

$^{13}$C NMR (151 MHz, DMSO-d$_6$) δ ppm 11.88, 17.45, 19.70, 21.88, 26.78, 29.04, 30.34, 30.42, 30.47, 31.02, 34.19, 36.47, 40.05, 40.43, 41.84, 46.15, 51.58, 122.97, 125.72, 125.78, 129.24, 136.20, 139.22, 142.11, 142.43, 144.61, 146.30, 176.92, 178.25, 181.38.

Although the embodiments of the present invention have been described in detail, according to the disclosed teaching, various modifications and alternations can be made to the details of the embodiments of the present invention, which are within the scope of the present invention. The scope of the invention is defined by the appended claims and any equivalents thereof.

What is claimed is:

1. A method for treating a triple negative breast cancer, comprising administering to a subject in need thereof an effective amount of a compound selected from (1)-(2), or a tautomer, a stereoisomer or a pharmaceutically acceptable salt or ester thereof:

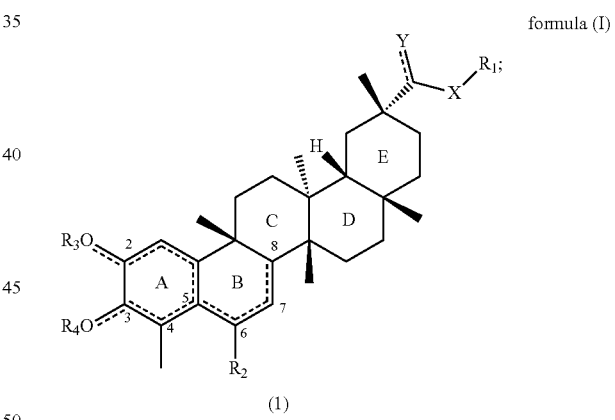

(1)

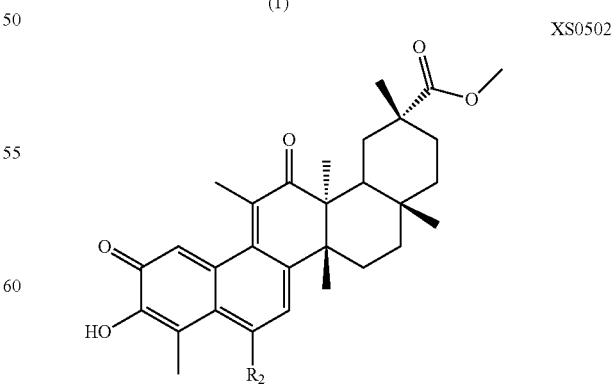

(2)

wherein, in formula (I),
X represents —NH—, —N(R)—, —O—, —CH$_2$— or halogen; wherein, when X is halogen, R$_1$ is absent;
when the bond between Y and the carbon atom attached thereto is a single bond, Y represents H, halogen, —OR, —SR or —NRR'; when the bond between Y and the carbon atom attached thereto is a double bond, Y represents O, S or NR;
R$_1$ is absent or represents H, —PO(OR)$_2$, C$_{1-6}$alkyl, glycosyl, C$_{1-6}$alkoxycarbonyl-C$_{1-6}$alkyl, 3- to 8-membered cycloalkyl-aminoacyl, aryl-C$_{1-6}$alkyl or aryl, wherein the C$_{1-6}$alkyl, glycosyl, C$_{1-6}$alkoxycarbonyl-C$_{1-6}$alkyl, 3- to 8-membered cycloalkyl-aminoacyl, aryl-C$_{1-6}$alkyl and aryl are unsubstituted or substituted with one or more substituents selected from the group consisting of halogen, hydroxy, amino, C$_{1-6}$alkyl, C$_{1-6}$alkoxy, C$_{1-6}$alkylamino and C$_{1-6}$alkanoyl;
R$_2$ represents H, D, —PO(OR)$_2$, —CONH$_2$, —NH$_2$, —NHR, —NRR', —NHCOR, —NRCOR, —NHCOOR, —NHCONHR, —NHCONRR', —NRCONHR, —NRCONRR', —OH, —OR, —OCONHR, —OCONRR', —SH, —SR, —SOR, —SOOR, —SO$_2$NHR", nitro, halogen, glycosyl, cyano, trifluoromethyl, C$_{1-6}$alkyl, 3- to 8-membered cycloalkyl, 3- to 8-membered heterocycloalkyl, aryl, C$_{1-6}$alkyl-substituted aryl, 6- to 15-membered heteroaryl, alkenyl, alkynyl, sulfinyl, sulfonic acid group or sulfonate group; wherein the C$_{1-6}$alkyl, 3- to 8-membered cycloalkyl, 3- to 8-membered heterocycloalkyl, aryl, C$_{1-6}$alkyl-substituted aryl, 6- to 15-membered heteroaryl, alkenyl and alkynyl are unsubstituted or substituted with one or more substituents selected from the group consisting of amino, halogen, hydroxy, oxy, C$_{1-6}$alkyl, C$_{1-6}$alkoxy, C$_{1-6}$alkylthio, C$_{1-6}$alkanoyl, 3- to 8-membered cycloalkyl, 3- to 8-membered oxocycloalkyl, cyano, trifluoromethyl, C$_{1-6}$alkoxycarbonyl, C$_{1-6}$alkylamido, ureido group, carbamate, carboxyl and aryl;
R$_3$ and R$_4$ each independently is absent or represents H, C$_{1-6}$alkyl, C$_{1-6}$alkanoyl, C$_{1-6}$alkoxycarbonyl, glycosyl, aryl-C$_{1-6}$alkyl or aryl, wherein the C$_{1-6}$alkyl, C$_{1-6}$alkanoyl, C$_{1-6}$alkoxycarbonyl, glycosyl, aryl-C$_{1-6}$alkyl and aryl are unsubstituted or substituted with one or more substituents selected from the group consisting of halogen, hydroxy, amino, C$_{1-6}$alkyl, C$_{1-6}$alkoxy, C$_{1-6}$alkylamino and C$_{1-6}$alkanoyl;
R and R' each independently is selected from H, C$_{1-6}$alkyl, 3- to 8-membered cycloalkyl, aryl-C$_{1-6}$alkyl or aryl, wherein the C$_{1-6}$alkyl, 3- to 8-membered cycloalkyl, aryl-C$_{1-6}$alkyl and aryl are unsubstituted or substituted with one or more substituents selected from the group consisting of halogen, hydroxy, amino, C$_{1-6}$alkyl, C$_{1-6}$alkoxy, and C$_{1-6}$alkylamino;
R" represents C$_{1-6}$alkyl or aryl;
" ------ " in Formula (I) represents single bond or double bond.

2. The method according to claim 1, wherein, in formula (I), the bond between Y and the carbon atom attached thereto is a double bond, and Y represents O.

3. The method according to claim 1, wherein, in formula (I), X in the compound represents —NH—, —N(R)—, —O—, —CH$_2$— or halogen; R represents C$_{1-6}$alkyl or 3- to 8-membered cycloalkyl; wherein, when X is halogen, R$_1$ is absent.

4. The method according to claim 1, wherein, in formula (I), R$_1$ is absent or represents hydrogen, C$_{1-4}$alkyl, —PO(OR)$_2$, monoglycosyl, C$_{1-4}$alkoxycarbonyl-C$_1$-4alkyl, 3- to 6-membered cycloalkyl-aminoacyl, aryl-C$_{1-4}$alkyl or aryl; wherein the C$_{1-4}$alkyl, monoglycosyl, C$_{1-4}$alkoxycarbonyl-C$_{1-4}$alkyl, 3- to 6-membered cycloalkyl-aminoacyl, aryl-C$_{1-4}$alkyl and aryl are unsubstituted or substituted with one or more substituents selected from the group consisting of: halogen, hydroxy, amino, C$_{1-4}$alkyl, C$_{1-4}$alkoxy, C$_{1-4}$alkylamino and C$_{1-4}$alkanoyl;
R represents C$_{1-4}$alkyl.

5. The method according to claim 1, wherein, in formula (I), R$_2$ represents H, D, —OH, —PO(OR)$_2$, C$_{1-6}$alkyl, 9- to 15-membered fused heteroaryl or sulfonate; wherein the C$_{1-6}$alkyl or 6- to 15-membered heteroaryl is unsubstituted or substituted with one or more substituents selected from the group consisting of amino, halogen, hydroxy, oxy, C$_{1-6}$alkyl, C$_{1-6}$alkoxy, C$_{1-6}$alkanoyl, cyano, trifluoromethyl and carboxyl;
R represents H, C$_{1-6}$alkyl or aryl.

6. The method according to claim 1, wherein, in formula (I), the Carbon 7 and Carbon 8 of the compound are linked with a carbon-carbon double bond.

7. The method according to claim 1, wherein, in formula (I), the bond between Y and the carbon atom attached thereto in the compound is a double bond.

8. The method according to claim 1, wherein, in formula (I), the bond between Y and the carbon atom attached thereto in the compound is a single bond.

9. The method according to claim 1, wherein the compound has the following structure:

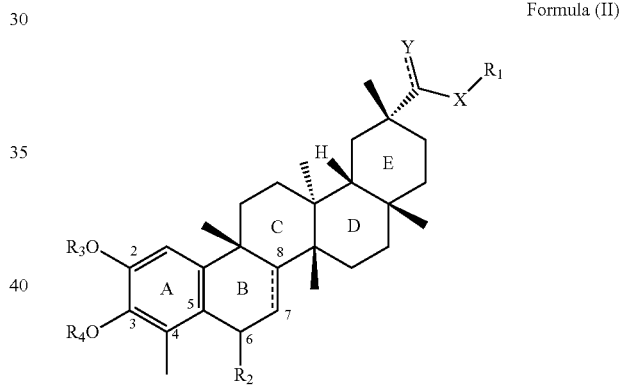

Formula (II)

wherein R$_3$ and R$_4$ each independently represents H, C$_{1-6}$alkyl or C$_{1-6}$alkanoyl.

10. The method according to claim 1, wherein the compound has the following structure:

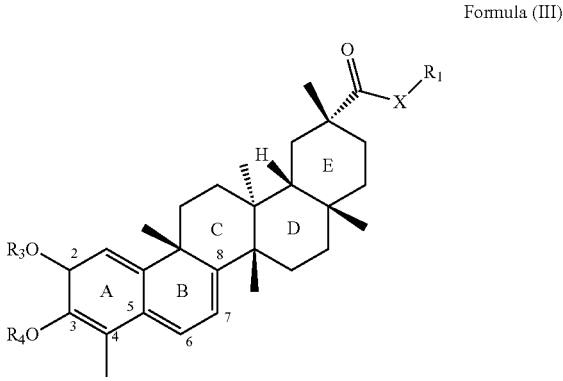

Formula (III)

wherein R$_4$ represents H, C$_{1-6}$alkanoyl, C$_{1-6}$alkoxycarbonyl or monoglycosyl substituted with one or more C$_{1-6}$alkanoyl groups.
11. The method according to claim 1, wherein the compound is selected from the following compounds:
XS0284
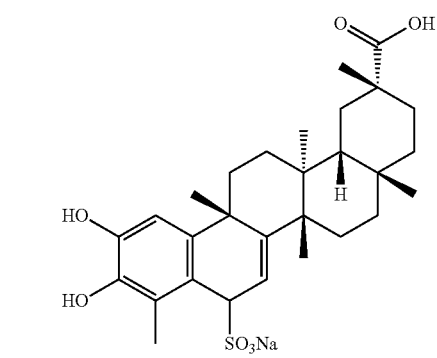
XS0285
XS0286
XS0287
-continued
XS0335
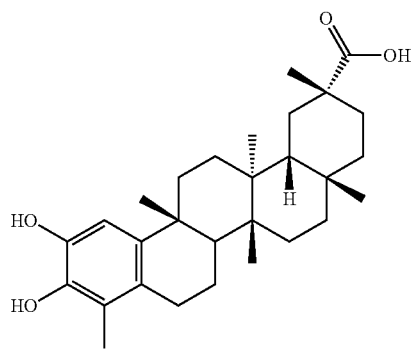
XS0366
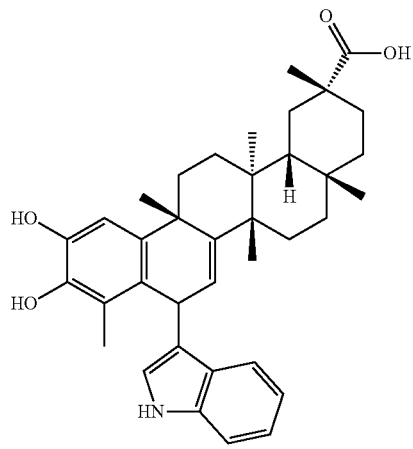
XS0394
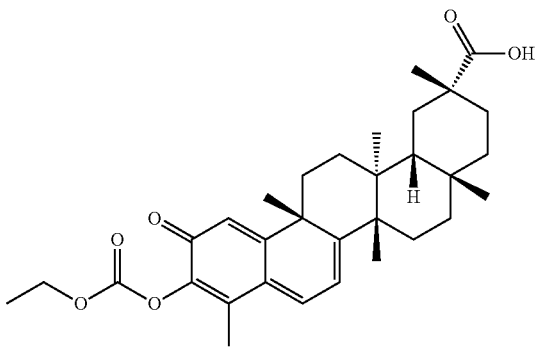
XS0395
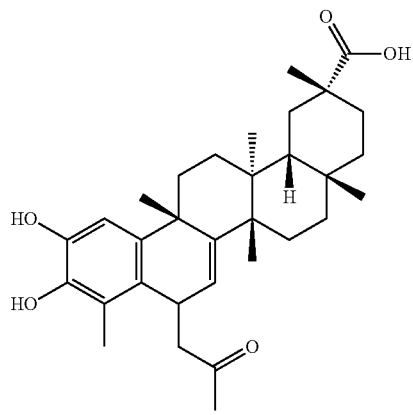

-continued
XS0418
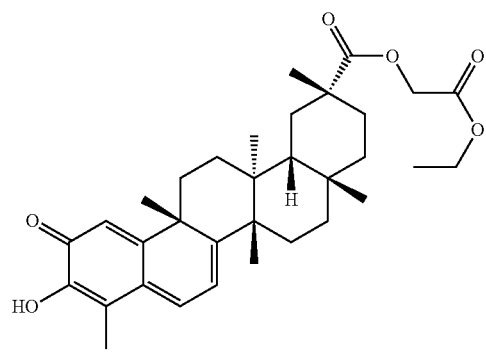
XS0419
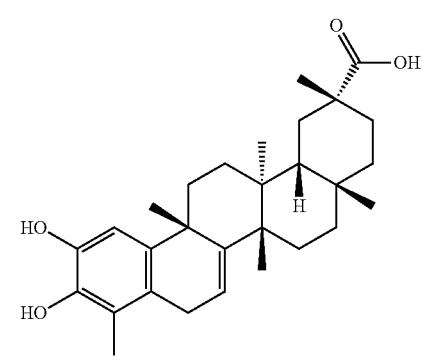
XS0421
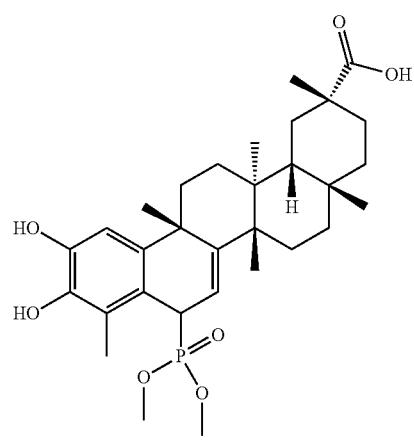
XS0434
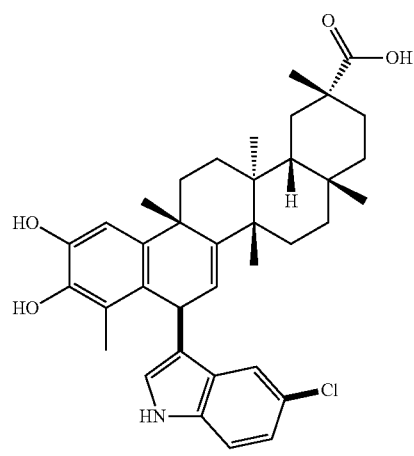
-continued
XS0435
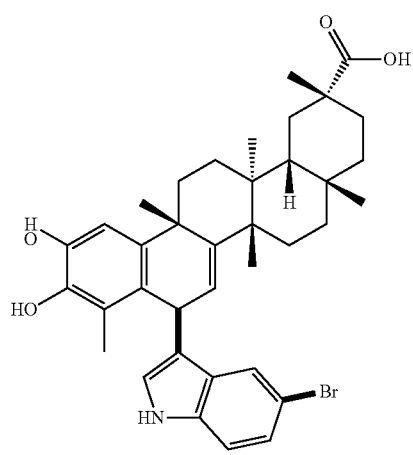
XS0436
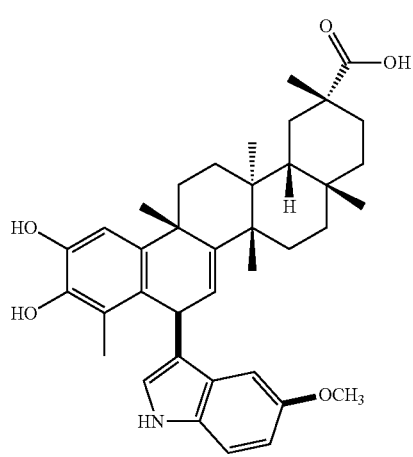
XS0437
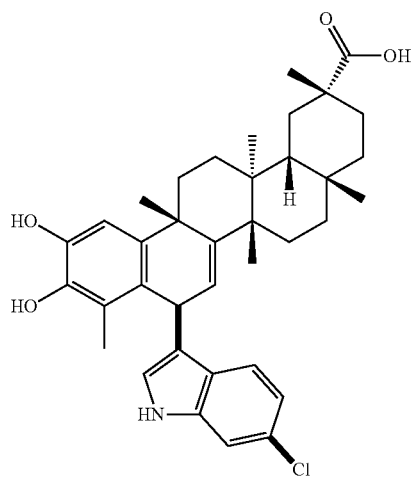

-continued
XS0438
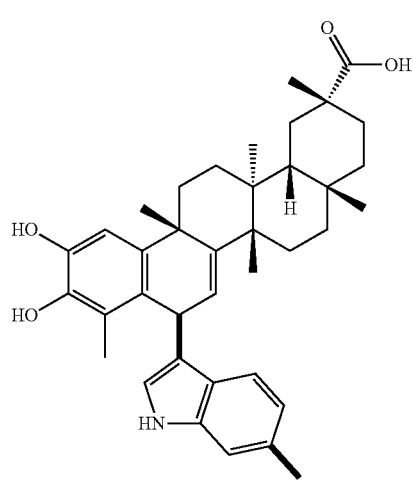
XS0439
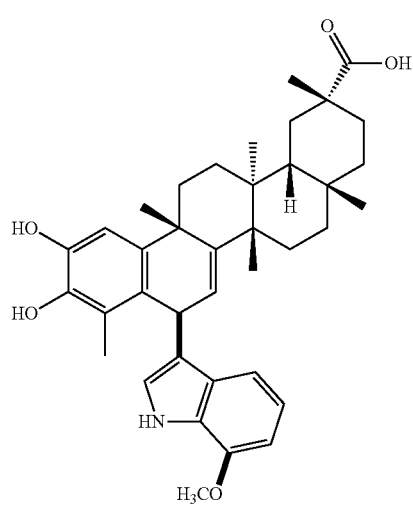
XS0440
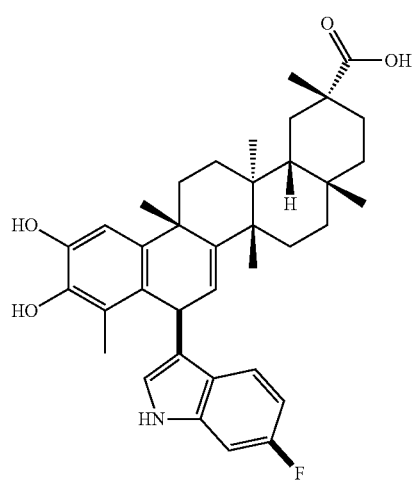
-continued
XS0441
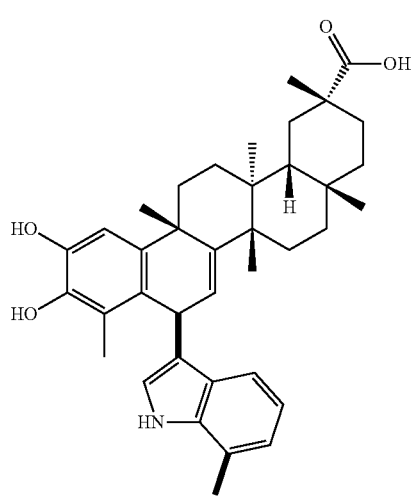
XS0442
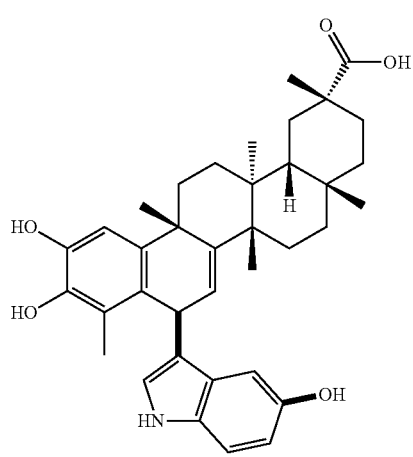
XS0443
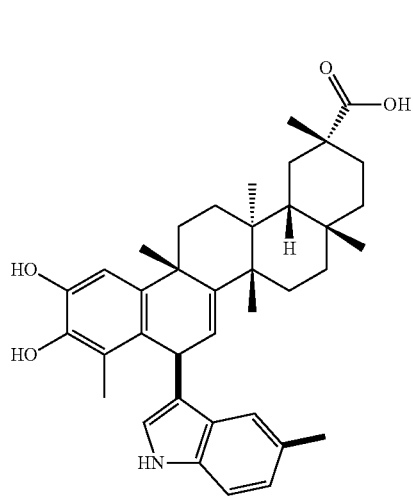

XS0444
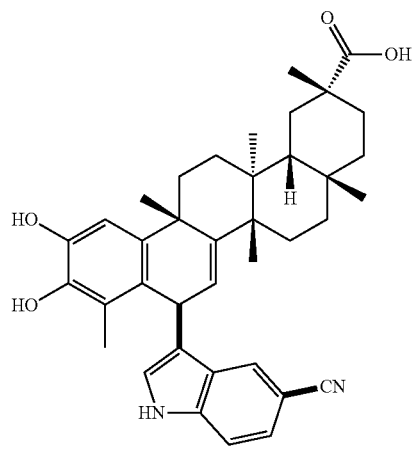
XS0445
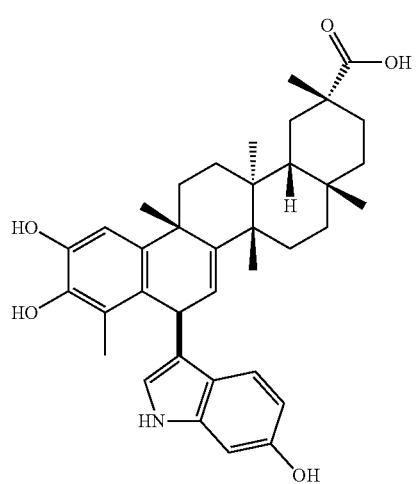
XS0446
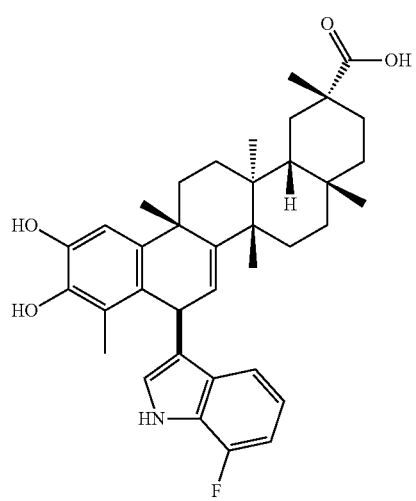
XS0447
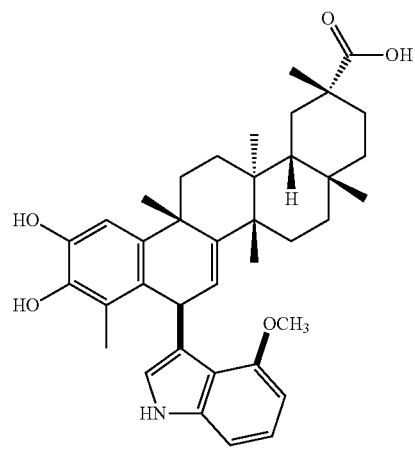
XS0448
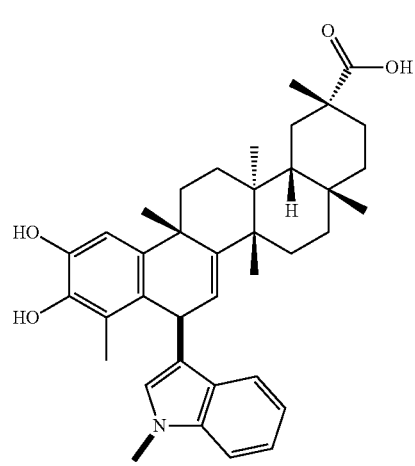
XS0449
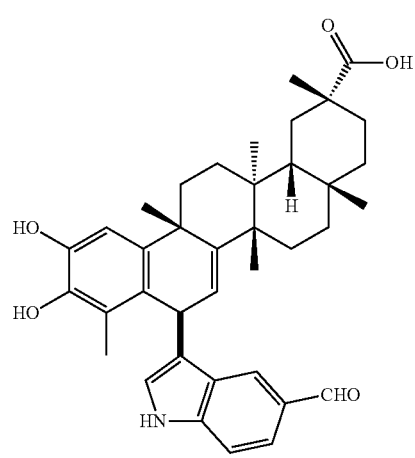

XS0457
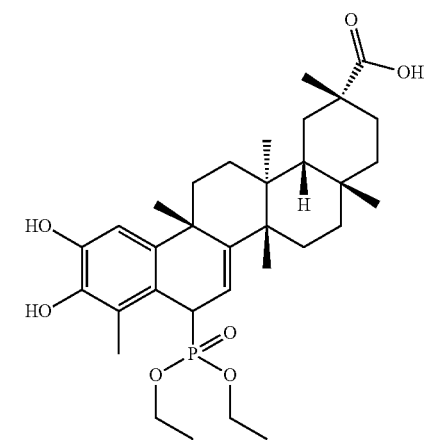
XS0462
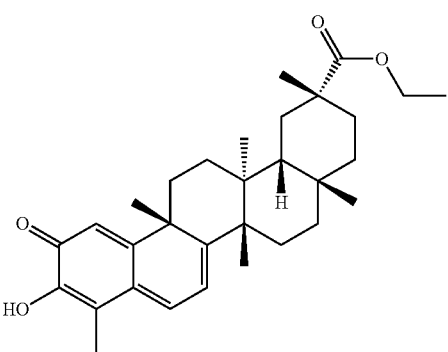
XS0463
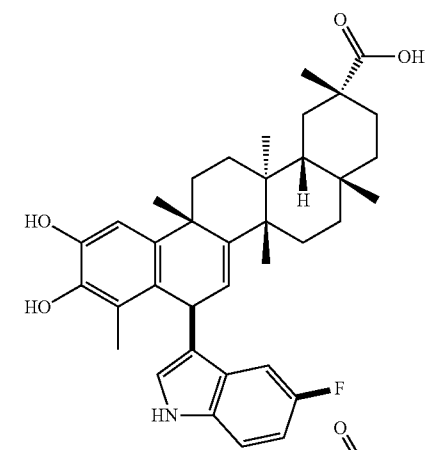
XS0464
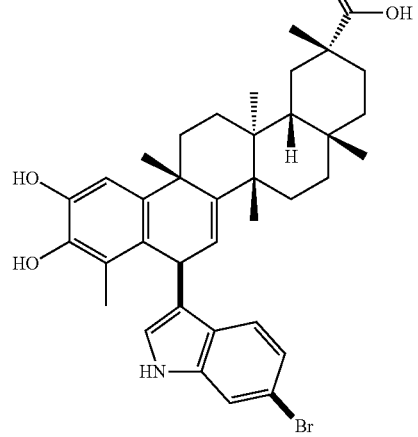
XS0473
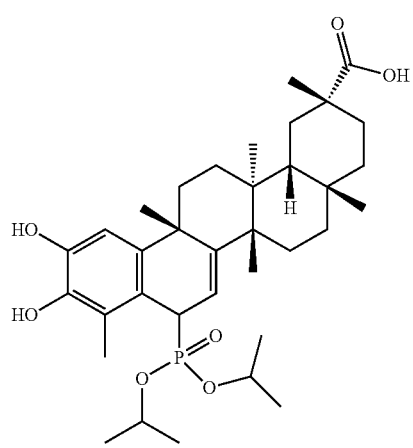
XS0474
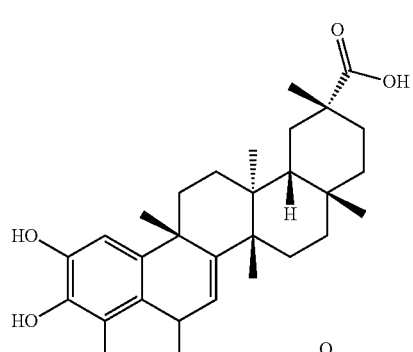
XS0478
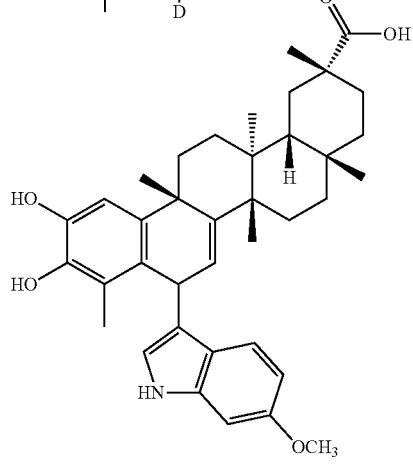
XS0479
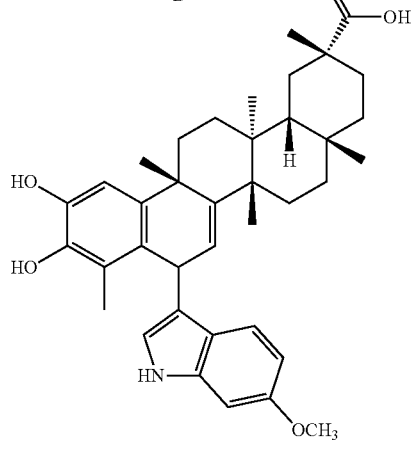

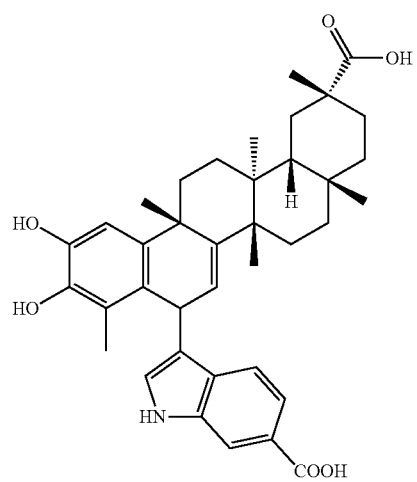
XS0480
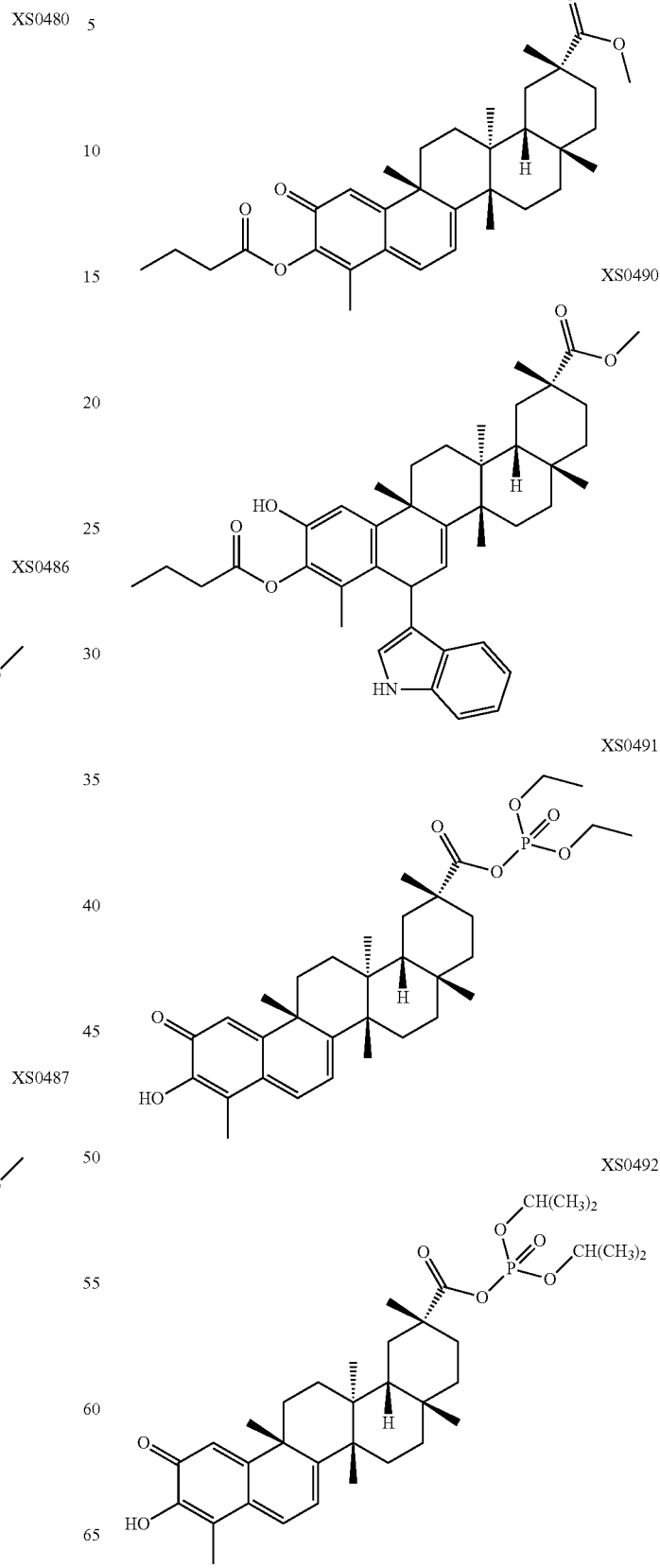
XS0486
XS0487
XS0488
XS0490
XS0491
XS0492

XS0493
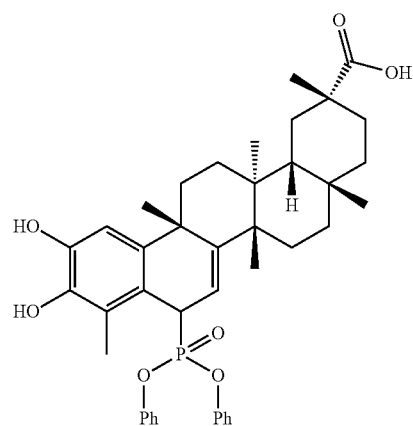
XS0508
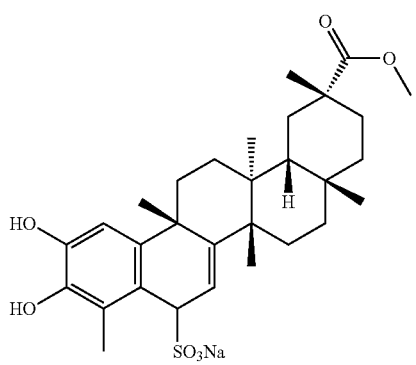
XS0503
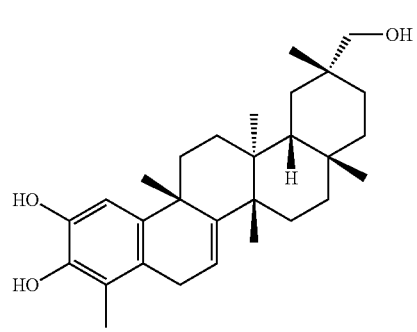
XS0509
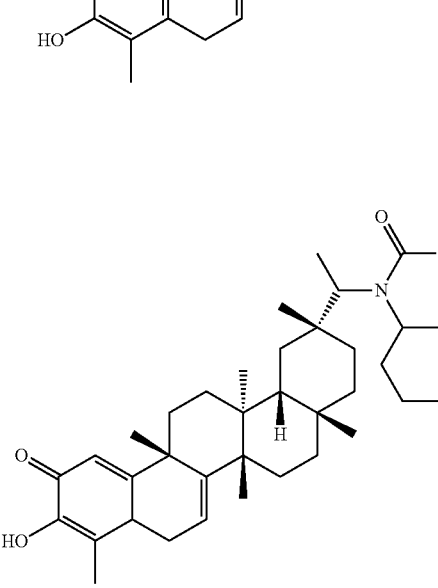
XS0506
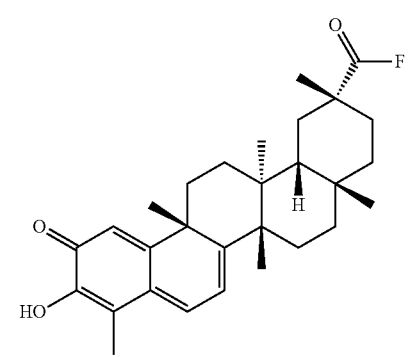
XS0507
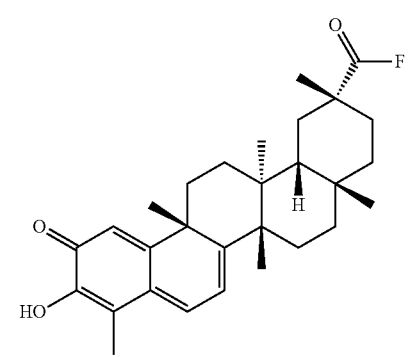
XS0514
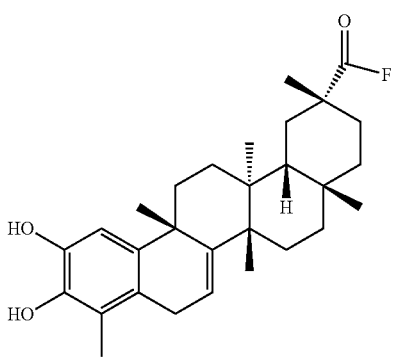

XS0515
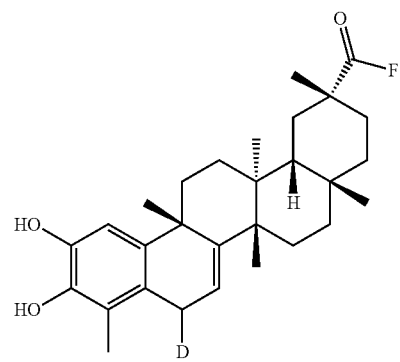
XS0534
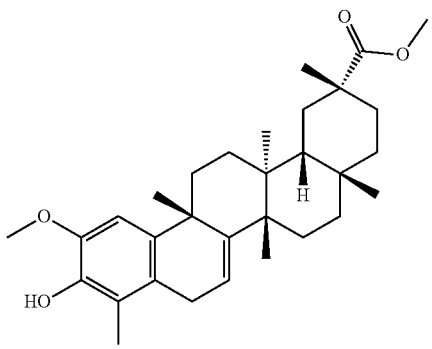
XS0516
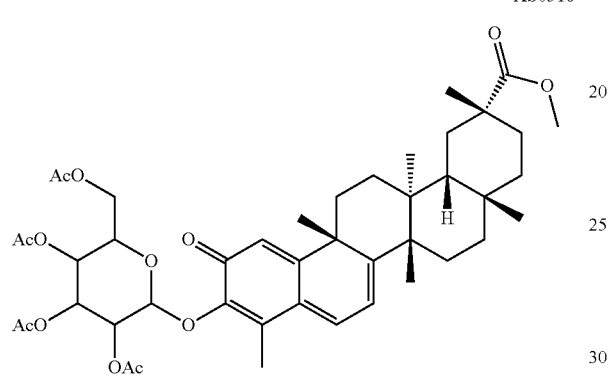
XS0536
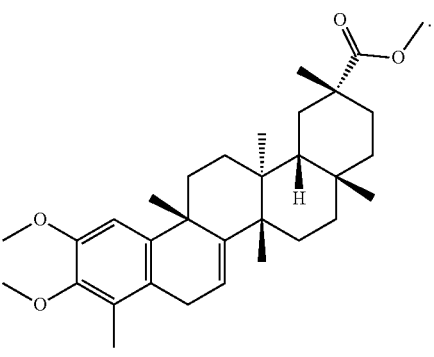
* * * * *

UNITED STATES PATENT AND TRADEMARK OFFICE
CERTIFICATE OF CORRECTION

PATENT NO. : 10,808,005 B2
APPLICATION NO. : 16/315099
DATED : October 20, 2020
INVENTOR(S) : Zhang et al.

Page 1 of 1

It is certified that error appears in the above-identified patent and that said Letters Patent is hereby corrected as shown below:

In the Claims

Column 97, Line 67: Claim 4, Delete "$C_{1-4}$alkoxycarbonyl-$C_{1-4}$alkyl," and insert
-- $C_{1-4}$alkoxycarbonyl-$C_{1-4}$alkyl, --

Signed and Sealed this
Eighth Day of December, 2020

Andrei Iancu
*Director of the United States Patent and Trademark Office*